(12) United States Patent
Chua et al.

(10) Patent No.: US 11,230,716 B2
(45) Date of Patent: *Jan. 25, 2022

(54) METHODS FOR STABILIZING PRODUCTION OF ACETYL-COENZYME A DERIVED COMPOUNDS

(71) Applicants: Amyris, Inc., Emeryville, CA (US); Total Marketing Services, Puteaux (FR)

(72) Inventors: Penelope R. Chua, Emeryville, CA (US); Adam Meadows, Emeryville, CA (US)

(73) Assignees: AMYRIS, INC., Emeryville, CA (US); TOTAL MARKETING SERVICES, Puteaux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/733,191

(22) Filed: Jan. 2, 2020

(65) Prior Publication Data
US 2020/0270643 A1 Aug. 27, 2020

Related U.S. Application Data

(62) Division of application No. 14/910,240, filed as application No. PCT/US2013/054028 on Aug. 7, 2013, now Pat. No. 10,563,229.

(51) Int. Cl.
*C12N 1/20* (2006.01)
*C12N 9/00* (2006.01)
(Continued)

(52) U.S. Cl.
CPC .............. *C12N 15/81* (2013.01); *C12N 1/16* (2013.01); *C12N 15/635* (2013.01); *C12P 5/007* (2013.01)

(58) Field of Classification Search
CPC ........... C12N 15/81; C12N 1/16; C12N 15/65
See application file for complete search history.

(56) References Cited

U.S. PATENT DOCUMENTS 10,808,015 B2 * 10/2020 Chua ................. C12P 5/02
2009/0137014 A1 5/2009 Tsuruta et al.

FOREIGN PATENT DOCUMENTS

| WO | WO 2007/026049 A2 | 3/2007 |
| WO | WO 2009/042070 A2 | 4/2009 |
| WO | WO 2012/106257 A1 | 8/2012 |

OTHER PUBLICATIONS

Extended European Search Report for EP Application No. 20151280.3 dated May 4, 2020; 12 pages.

(Continued)

*Primary Examiner* — Yong D Pak
(74) *Attorney, Agent, or Firm* — Squire Patton Boggs (US) LLP

(57) ABSTRACT

The present disclosure relates to the use of a switch for the production of heterologous non-catabolic compounds in microbial host cells. In one aspect, provided herein are genetically modified microorganisms that produce non-catabolic compounds more stably when serially cultured under aerobic conditions followed by microaerobic conditions, and methods of producing non-catabolic compounds by culturing the genetically modified microbes under such culture conditions. In another aspect, provided herein are genetically modified microorganisms that produce non-catabolic compounds more stably when serially cultured in the presence of maltose followed by the reduction or absence of maltose, and methods of producing non-catabolic compounds by culturing the genetically modified microbes under such culture conditions.

Figure 1:
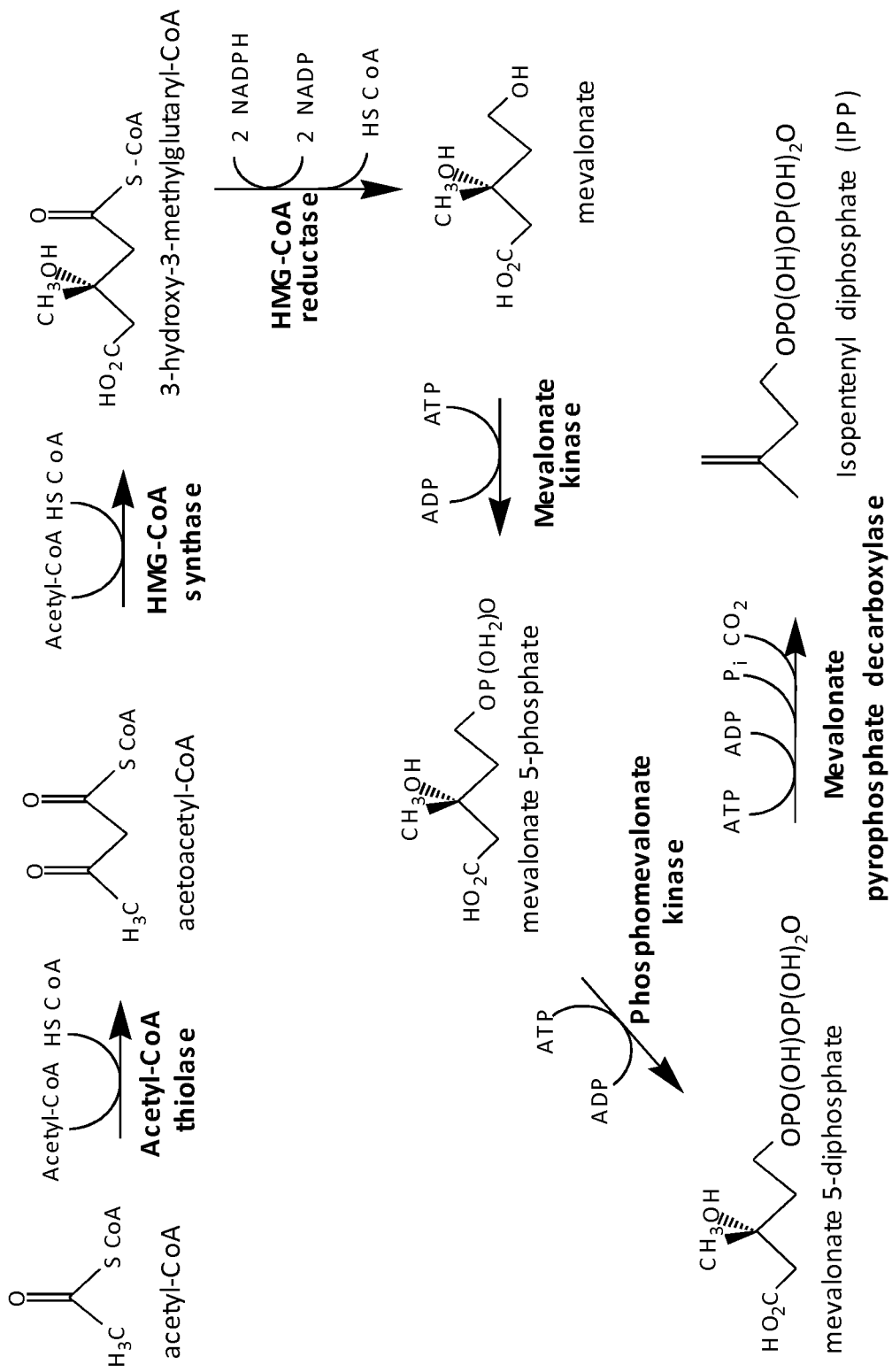

11 Claims, 14 Drawing Sheets
Specification includes a Sequence Listing.

GAL-regulon-based maltose switch

Pathway is repressed in the presence of maltose, derepressed in the absence of maltose

(51) Int. Cl.
*C12N 15/00* (2006.01)
*C12N 15/81* (2006.01)
*C12N 15/63* (2006.01)
*C12N 1/16* (2006.01)
*C12P 5/00* (2006.01)

(56) References Cited

OTHER PUBLICATIONS

Roland Prielhofer et al., "Induction without methanol: novel regulated promoters enable high-level expression in Pichia pastoris", Microbial Cell Factories, vol. 12, No. 1, Jan. 1, 2013, p. 5, XP055301811.
Virve Vidgren et al., "Identification of regulatory elements in the AGT1 promoter of ale and lager strains of brewer's yeast", Yeast, vol. 28, No. 8, Jul. 13, 2011, pp. 579-594, XP055411220.
International Preliminary Report on Patentability in PCT/US2013/054028 dated Feb. 18, 2016, 10 pages.
International Search Report and Written Opinion in PCT/US2013/054028 dated Jul. 9, 2014, 16 pages.
Abramova et al. "Reciprocal Regulation of Anaerobic and Aerobic Cell Wall Mannoprotein Gene Expression in *Saccharomyces cerevisiae*", *Journal Of Bacteriology*, May 2001, vol. 183, No. 9, pp. 2881-2887.
Baofu Ni et al. "Identification of the Upstream Activating Sequence of MAL and the Binding Sites for the MAL63 Activator of *Saccharomyces cerevisiae*", *Molecular And Cellular Biology*, Jul. 1990, vol. 10, No. 7, pp. 3797-3800.
Berkner et al. "Inducible and Constitutive Promoters for Genetic Systems in Sulfolobus Acidocaldarius", *Extremophiles*, 2010, vol. 14, pp. 249-259.
Boos et al. "Maltose/Maltodextrin System of *Escherichia coli*: Transport, Metabolism, and Regulation", *Microbiology And Molecular Biology Reviews*, Mar. 1998, vol. 62, No. 1, pp. 204-229.
Da Silva, "Introduction and expression of genes for metabolic engineering applications in *Saccharomyces cerevisiae*", FEMS Yeast Res. Mar. 2012;12(2):197-214. Epub Jan. 12, 2012. Review.
Finley Jr et al., "Regulated expression of proteins in yeast using the MAL61-62 promoter and a mating scheme to increase dynamic range", Gene, vol. 285, Issues 1-2, Feb. 20, 2002, pp. 49-57.

Guarente et al. "A GAL10-CYC1hybrid Yeast Promoter Identifies the GAL4 Regulatory region as an Upstream Site", *Proc. Natl. Acad. Sci. USA*, Dec. 1, 1982, vol. 79, pp. 7410-7414, XP001313404.
Hu et al. "Analysis of the Mechanism by which Glucose Inhibits Maltose Induction of MAL Gene Expression in *Saccharomyces*", *Genetics*, Jan. 1, 2000, vol. 154, No. 1, pp. 121-132, XP055112677.
Kwast et al. "Genomic Analyses of Anaerobically Induced Genes in *Saccharomyces cerevisiae*: Functional Roles of Rox1 and Other Factors in Mediating the Anoxic Response", *Journal Of Bacteriology*, Jan. 2002, vol. 184, No. 1, pp. 250-265.
Lai et al. "Dynamical Remodeling of the Transcriptome during Short-Term Anaerobiosis in *Saccharomyces cerevisiae*: Differential Response and Role of Msn2 and/or Msn4 and Other Factors in Galactose and Glucose Media", *Molecular And Cellular Biology*, May 2005, vol. 25, No. 10, pp. 4075-4091.
Linde et al. "Genome-Wide Transcriptional Analysis of Aerobic and Anaerobic Chemostat Cultures of *Saccharomyces cerevisiae*", *Journal Of Bacteriology*, Dec. 1999, vol. 181, No. 24, pp. 7409-7413.
Ostegard et al., "The impact of GAL6, GAL80, and MIG1 on glucose control of the GAL system in *Saccharomyces cerevisiae*", FEMS Yeast, Research 1 (2001), pp. 47-55.
Paddon et al. "High-Level Semi-Synthetic Production of the Potent Antimalarial Artemisinin", *Nature*, Apr. 25, 2013, vol. 496, No. 7446, pp. 528-532, XP055112673.
Piper et al. "Reproducibility of Oligonucleotide Microarray Transcriptome Analyses", *The Journal Of Biological Chemistry*, Oct. 4, 2002, vol. 277, No. 40, pp. 37001-37008.
Ran et al. "Hsp90 Cochaperone Aha1 Is a Negative Regulator of the *Saccharomyces* MAL Activator and Acts Early in the Chaperone Activation Pathway", *J Biol Chem.*, Apr. 30, 2010, vol. 285, No. 18, pp. 13850-13862.
Schleif, "Two Positively Regulated Systems, ara and mal", *Escherichia coli and Salmonella Cellular and Molecular Biology*, pp. 1300-1309.
Sertil et al. "The DAN1 Gene of S. Cerevisiae is Regulated in Parallel with the Hypoxic Genes, but by a different Mechanism", *Gene*, 1997, vol. 192, pp. 199-205.
Tai et al. "Two-dimensional Transcriptome Analysis in Chemostat Cultures", *The Journal Of Biological Chemistry*, Jan. 7, 2005, vol. 280, No. 1, pp. 437-447.

* cited by examiner

GAL-regulon-based maltose switch

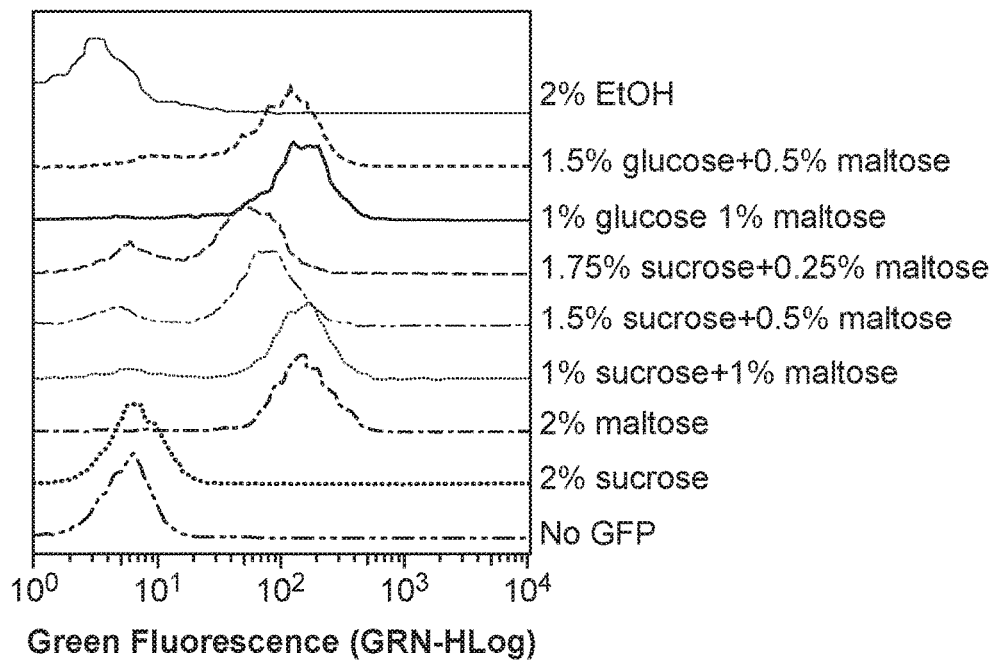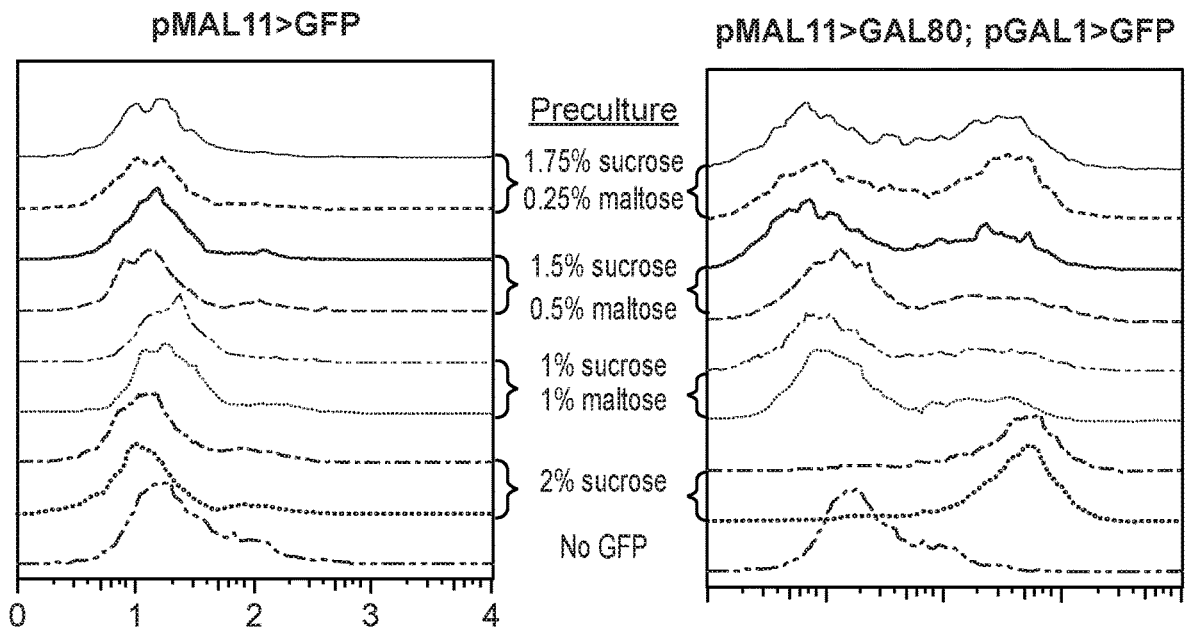
Figure 11

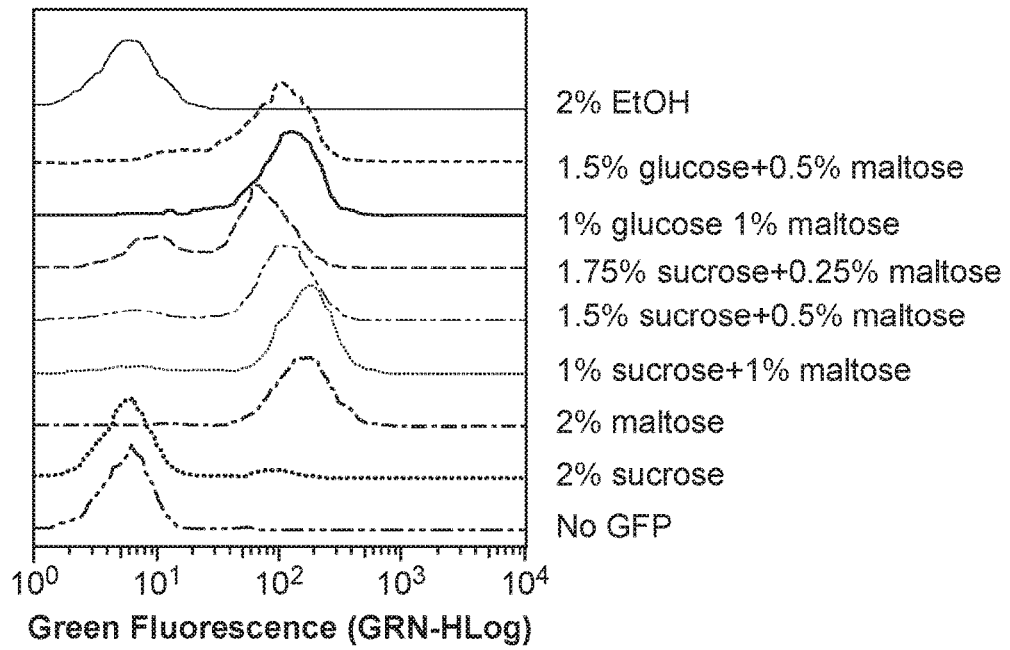
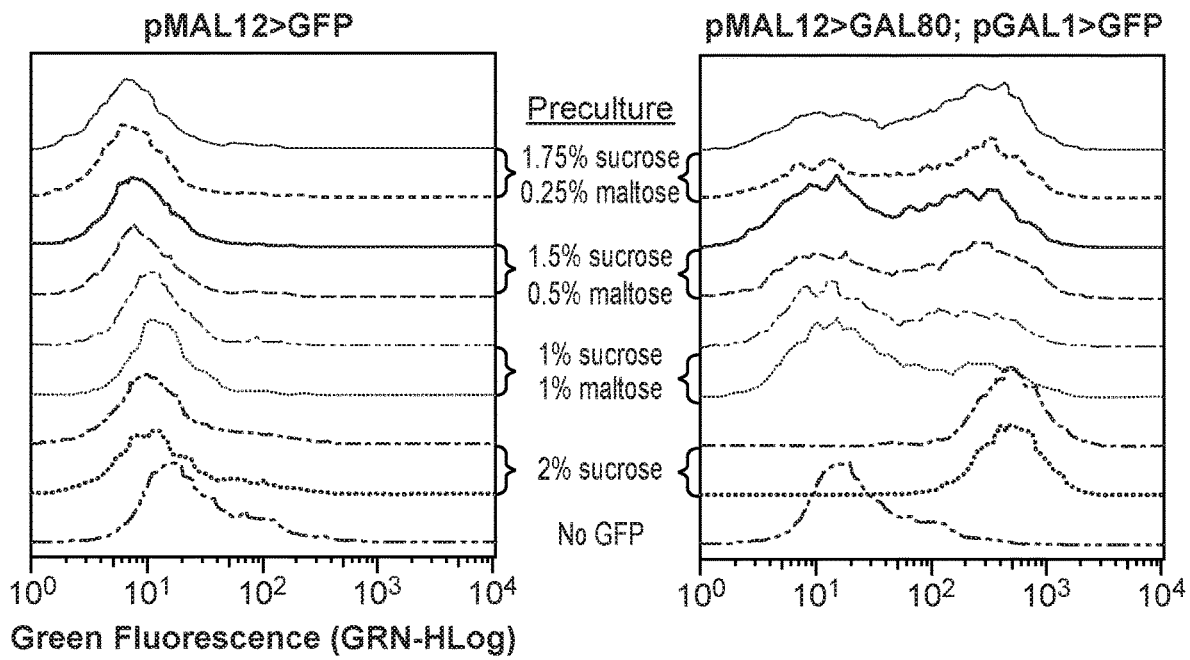
Figure 12

A.
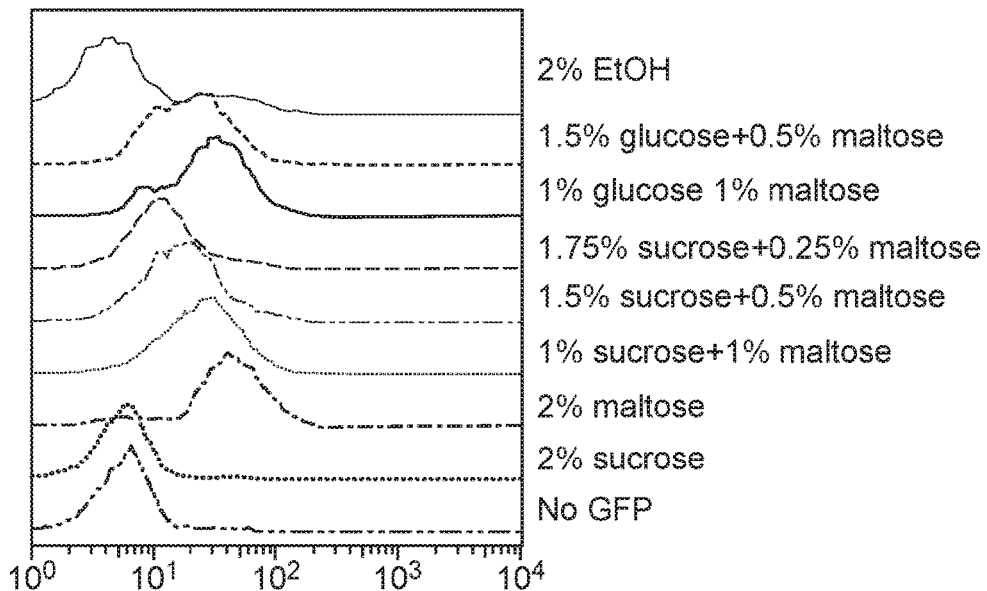
B.
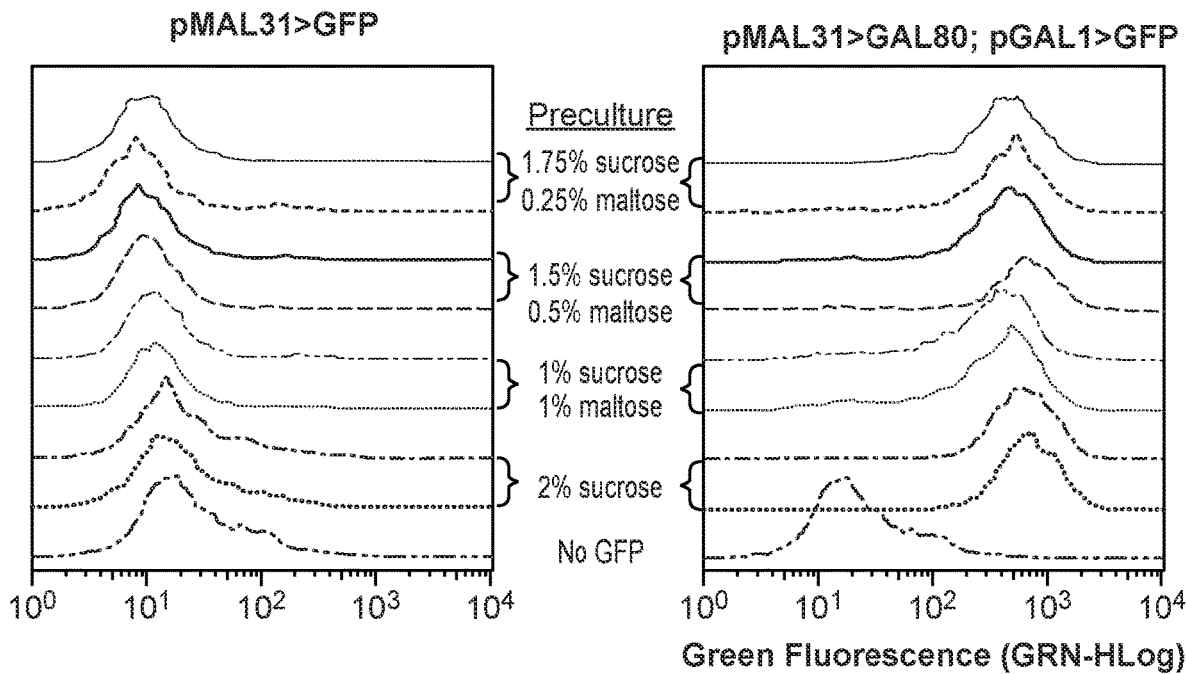
Figure 13

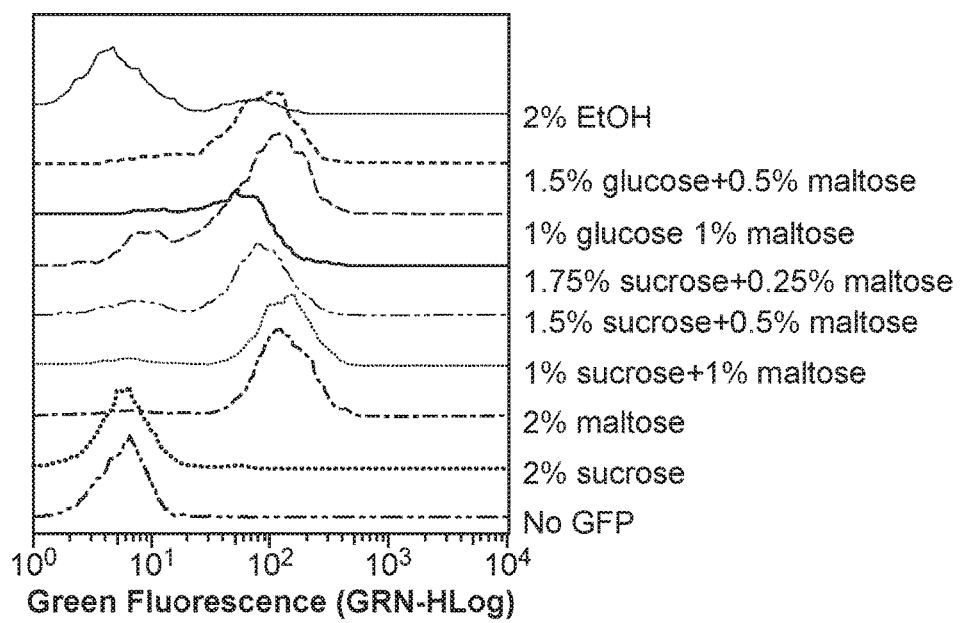
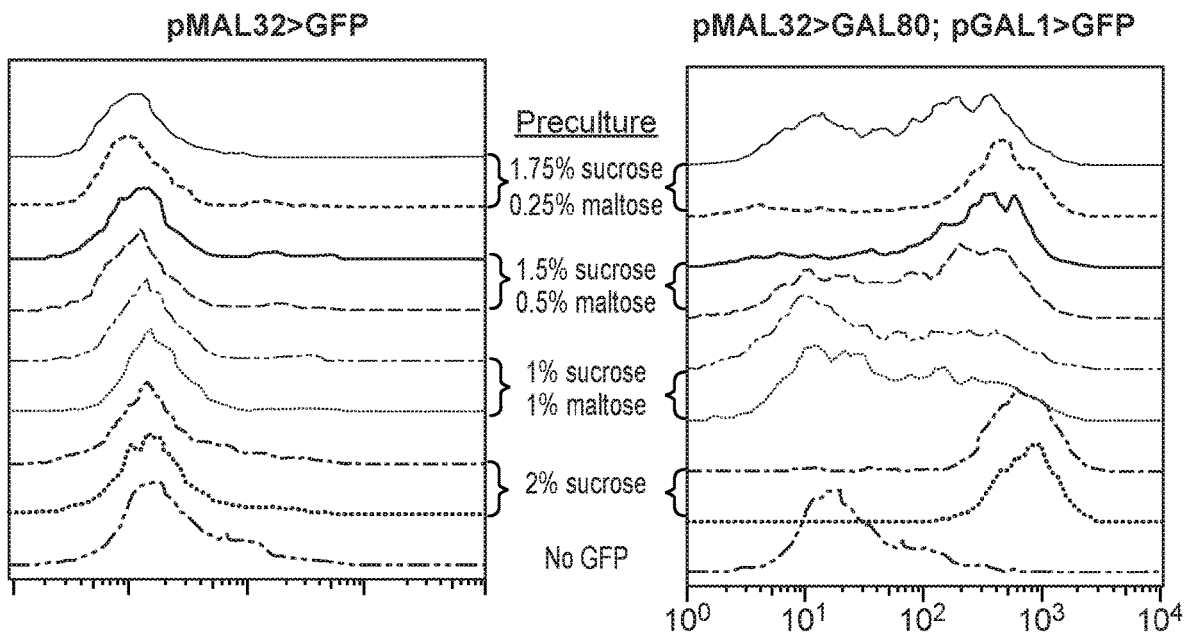
Figure 14

SEQUENCE LISTING

<160> NUMBER OF SEQ ID NOS: 17

<210> SEQ ID NO 1
<211> LENGTH: 551
<212> TYPE: DNA
<213> ORGANISM: Artificial Sequence
<220> FEATURE:
<223> OTHER INFORMATION: Synthetic DNA: Mutant DAN1 promoter #1

<400> SEQUENCE: 1

```
agctcaattc acgctggatt cggcgatccg ttttcttcaa tcctcacgtg ctttcttcgt    60
ttgagtgcaa aagttcatat gatgctatct cccgcttacc ttattagtcg aaaatgggga   120
gaatttccta ttttatctgt cgtttagcac atatggccag gaagatacat aaggtttcgc   180
cgaacgacgg ggtcaattcg tccttttttgt acacatcgtt taatttatga ggaaaaattg   240
atgaatgtat cctccgtaga cgctcctctg aaaagtttca tgttccctgc gcgttccttt   300
gataggcaat aaaacaatac aacgcgtgcc tttgaaaatg ccgagatcta tacgaggcct   360
ctaacaaaac atcgttcagg aacagagaat actagaaatg caaaagggtc cctgggtact   420
cattgaatag agatgattga aaatactgcg tataaaatag cacgactaag tgatactatt   480
tttatgtcga cacggtacta tttcttcttt ttcagataaa agtgtagcat actaaatata   540
taccccaagt a                                                         551
```

<210> SEQ ID NO 2
<211> LENGTH: 551
<212> TYPE: DNA
<213> ORGANISM: Artificial Sequence
<220> FEATURE:
<223> OTHER INFORMATION: Synthetic DNA: Mutant DAN1 promoter #2

<400> SEQUENCE: 2

```
agctcaattc acgctggatt aggcggtccg ttttcttcaa tcctcacgtg ctttcttcgt    60
ttgagtgcaa aagttcatat gatgctatct cccgcttatc ttattagtcg aaaatgggga   120
gaatttccta ttttatctgt cgtttagcac atatggccag gaaaatacat aaggtttcgc   180
cgaacggcgg ggtcaattcg tcctttctgt acacatcgtt taattcatga gggaaaattg   240
atgaatgtat cctccgtaga cgctcctctg aaaagtttca tgtttcctgc gcgttccttt   300
gataggcaat aaaacaatac gacgcgtgcc tttgaaaatg ccaggatcta tacgaggcct   360
ctaacaaaac atcgttcagg aacagagaat gctagaaatg caagagggtc cctgggtact   420
cattgaatag aaatgattga aaatgctgcg tataaaatag cacgactaaa tgatactatt   480
tttatgtcga cacggtacta tttcttcttt ttcagataaa agtgtagcat actaaatata   540
taccccaagt a                                                         551
```

<210> SEQ ID NO 3
<211> LENGTH: 551
<212> TYPE: DNA
<213> ORGANISM: Artificial Sequence
<220> FEATURE:
<223> OTHER INFORMATION: Synthetic DNA: Mutant DAN1 promoter #3

<400> SEQUENCE: 3

```
agctcaattc acgctggact cggcggtccg ttttcttcaa tcctcacgtg ctttcttcgt    60
ttgagtgcaa aagttcatat gatgctatct cccgcttatc ttattagtcg aaaatgggga   120
gaatttccta ttttatctgt cgtttagcac atatggccag gaaagtacat agggtttcgc   180
cgaacgacgg ggtcaattcg tccttttttgt acacatcgtt taatttacga ggaaaaattg   240
```

```
atgaatgtat cctccgtaga cgctcctctg aaaagtttca cgtttcctgc gcgttccttt    300
gataggcaat aagacaatac aacgcgtgcc cttgaaactg ccaagatcta tacgaggcct    360
ctaacaaaac atcgttcagg aacagagaat gctagaaatg caaaagggtc cctgggtact    420
cattgaatag aaatgattga aaatactgcg tataaaatag cacgactaaa tgatactatt    480
tttatgtcga cacggtacta tttcttcttt ttcagatcaa agtgtagcat actaaatata    540
taccccaagt a                                                          551
```

```
<210> SEQ ID NO 4
<211> LENGTH: 551
<212> TYPE: DNA
<213> ORGANISM: Artificial Sequence
<220> FEATURE:
<223> OTHER INFORMATION: Synthetic DNA: Mutant DAN1 promoter #4

<400> SEQUENCE: 4
agctcaattc acgctggatt cggcgattcg ttttcctcaa tcctcacgtg ctttcttcgt     60
ttgagtgcaa aagtccatat gatgccatct cccgcttatc ttattagtcg aaaatgggga    120
gaatttccta ttttacctgt cgtttagcac atatggccag gaagatacat aaggtttcgc    180
cgaacgacgg ggtcaattcg tcctttttgt acacatcgtt taatttatga gggaaacttg    240
atgaatgtat cctccgtaga cgctcctctg aaaagtttca tgtttcctgc gcgttccttt    300
gataggcgat aaaacaatac aacgcgtgcc tttgaagatg ccaaggtcta tacgaggcct    360
ctaacaagac atcgttcagg aacagagaac gctagaaatg caaaagggtc cctgggtact    420
cattgagtag aaatgattaa aaatactgcg tataaaatag cacgactaaa tgatactatc    480
tttatgtcga cacggtacta tttcttcttt ttcagataaa agtgtagcat actaaatata    540
taccccaagt a                                                          551
```

```
<210> SEQ ID NO 5
<211> LENGTH: 551
<212> TYPE: DNA
<213> ORGANISM: Artificial Sequence
<220> FEATURE:
<223> OTHER INFORMATION: Synthetic DNA: Mutant DAN1 promoter #5

<400> SEQUENCE: 5
agctcaattc acgctggatt cggcgatccg ttttcttcaa tcctcacgtg ctttcttcgt     60
ttaagcgcaa aagttcacat gatgctatct cccgcttatc ttattagtcg aaaatgggga    120
gaatttccta ttttatctgt cgtttagcac atatggccag gaaaatacat aaggtttcgc    180
cgaacgacgg ggtcaattcg tcctttttgt acacatcgtt taatttatga ggaaaaattg    240
atgaatgtat cctccgtaga cgctcctctg aaaagtttcg tgtttcctgc gcgttccttt    300
gataggtaac aaaacaatac aacgcgtgcc tttgaaaatg ccaagatcta tacgaggcct    360
ctaacaaaac atcgttcagg aacagggaat gctagagatg caaaagggtc cctgggtact    420
cgttgaatag aaatgattga aaatactgcg tataaaatag cacgactaaa tgatactatt    480
tttatgtcga cgcggtacta tttcttcttt ttcagataaa agtgtagcat actaaatata    540
taccccaagt a                                                          551
```

```
<210> SEQ ID NO 6
<211> LENGTH: 551
<212> TYPE: DNA
<213> ORGANISM: Artificial Sequence
<220> FEATURE:
```

<223> OTHER INFORMATION: Synthetic DNA: Mutant DAN1 promoter #6

<400> SEQUENCE: 6

```
agctcaattc acgctggatt cggcgatccg ttttcttcaa tcctcacgtg ctctcttcgt    60
ttgagtgcaa aagctcatat gatgctatct cccgcttatc ttattagtcg aaaatgggga   120
ggatttccta ttttgtctgt cgtttagcac atatggccag gaaaatacat aaggtttcgc   180
cgaacgacgg ggtcaatgcg tcctctctgt acacatcgtt taatttatga ggaaaaattg   240
atgaatgtat cctccgtagg cgctcctctg aaaagtttca tgtttcctgc gcgttccttt   300
gataggcaat aaaacaatac aacgcgtgcc tctgaaaatg ccaggatcta tacgaggcct   360
ctaacaaaac atcgttcagg aacagagaat gttagaaatg caaagggtc cctgggtact    420
cattgaatgg aaacgattga aaatactgcg tataaaatag cacgactaaa tgataccatt   480
tttatgtcga cacggtacta tttcttcttt ctcagataaa agtgtagcat actaaatata   540
taccccaagt a                                                        551
```

<210> SEQ ID NO 7
<211> LENGTH: 551
<212> TYPE: DNA
<213> ORGANISM: Artificial Sequence
<220> FEATURE:
<223> OTHER INFORMATION: Synthetic DNA: Mutant DAN1 promoter #7

<400> SEQUENCE: 7

```
agctcaattc acgctgggtt cggcgatccg ttttcttcaa tcctcacgtg ctttcttcgt    60
ttgagtgcaa aagttcatat gatgctatct cccgcttatc ttattagtcg aaaatgggga   120
gaatttccta ttttatctgt cgtttagcgc atatggccag gaaaatacat aaggtctcgc   180
cgaacgacgg ggtcaattcg tccttttgt acacatcgtt taatttatga ggagaaattg    240
gtgaatgtat cctccgtaga cgctcctctg aaaagtttca tgtttcctgc gcgttccttt   300
gataggcaat aaaacaatac aacgcgtgcc tttgaaaatg ccaagatcta tacgaggcct   360
ctaacaaaac attgttcagg aacagagaat gctaggaatg caaagggtc cctgggtact    420
cattgaatag aaatgattga aaatactgcg tataaaatag cacgaccaca tgatactatt   480
tttatgtcga cgcggtacta tttcttcctt ttcagataaa agtgtagcat actaaatata   540
taccccaagt a                                                        551
```

<210> SEQ ID NO 8
<211> LENGTH: 551
<212> TYPE: DNA
<213> ORGANISM: Artificial Sequence
<220> FEATURE:
<223> OTHER INFORMATION: Synthetic DNA: Mutant DAN1 promoter #8

<400> SEQUENCE: 8

```
agctcagttc acgctggatt cggcgatccg ttttcttcaa tcctcacgtg ctttcctcgc    60
ttgagtgcaa aagttcatat gatgctatct cccgcttatc ttattagtcg aaaatgggga   120
gaatttccta ttttatctgt cgtttagcac atatggccag ggaaatacat gaggtttcgc   180
cgaacgacgg ggtcagttcg tccttttgt gcacaccgtt taatttatga ggagaagttg    240
atgaatgtat cctccgtaga cgctcctccg aaaggtttca tgtttcctgc gcgtttcttt   300
gacaggcaat aaaacaatac agcgcgcgcc tttgaaaatg ccaagatcta tacgaggcct   360
ctaacgaaac atcgcccagg acgagagaat gctagaaatg cgaaagggtc cctgggtact   420
cattgaacag aaatgattga aaatactgcg tataaaatag cacgactaaa tgatactatt   480
```

```
tttatgtcgg cacggtacta tttcttcttt ttcagataaa agtgtagcat actaaatata    540
taccccaagt a                                                         551

<210> SEQ ID NO 9
<211> LENGTH: 551
<212> TYPE: DNA
<213> ORGANISM: Artificial Sequence
<220> FEATURE:
<223> OTHER INFORMATION: Synthetic DNA: Mutant DAN1 promoter #9

<400> SEQUENCE: 9
agctcaattc acgctggatt cggcgatccg ttttcttcaa tcctcacgtg ctttcttcgt    60
ttgagtgcaa aagttcatat gatgctatct cccgcttatc ttattagtcg aaaatgggga   120
gaatttccta ttttatctgt cgtttagcac atatggccag gaaaatacat aaggtttcgc   180
cgaacgacgg ggtcaattcg tccttttttgt acacatcgtt taatttatga ggaaaaattg   240
atgaatgtat cctccgtaga cgctcctctg aaaagtctca tgtttcctgc gcgttccttt   300
gataggcaat aagacaatac aacgcgtgcc tttgaaaatg ccaagatcta tacgaggcct   360
ctaacaaaac atcgttcagg aacagagaat gctagaaatg caaagggtc cctgggtact    420 cattgaatag agatgattga aaatactgcg tataaaatag cacgactaag tgatactatt   480
tttatgtcga cacggtacta tttcttcttt ttccgataaa agtgtagtat actaaatata   540
taccccaagt a                                                         551

<210> SEQ ID NO 10
<211> LENGTH: 551
<212> TYPE: DNA
<213> ORGANISM: Artificial Sequence
<220> FEATURE:
<223> OTHER INFORMATION: Synthetic DNA: Mutant DAN1 promoter #10

<400> SEQUENCE: 10
agcccaattc acgccggatt cagcgatccg ttttcttcag tcctcacgtg ctttcttcgt    60
ttgagtgcaa aagttcatat gatgctatct cccgcttatc ttattagtcg aaaatgggga   120
gaatttccta tcttatctgt cgtttagcac atgtggccag gaaaatacat aaggtttcgc   180
cgaacgacgg ggtcaattcg cccttttttgt acacatcgtt taatttatga ggaaaaattg   240
atgaatgtat cctccgtaga cgctcctctg aaaagtttca tgtttcctgc gcgttcctct   300
gataggcaat aaaacaatac aacgcgtgcc tttgaaaatg ccaagatcta tacgaggcct   360
ctaacaaaac atcgttcagg aacagagaat gctagaaatg caaagggtc cctgggtact    420 cattgaatag aaatgattga aaatactgcg tataaaatag cacgactaaa tgataccatt   480
tttatgtcga cacggtacta tttcttcttt ttcagataaa agtgtagcat actaaatata   540
taccccaagt a                                                         551

<210> SEQ ID NO 11
<211> LENGTH: 551
<212> TYPE: DNA
<213> ORGANISM: S. cerevisiae
<220> FEATURE:
<221> NAME/KEY: misc_feature
<222> LOCATION: (1)..(551)
<223> OTHER INFORMATION: Wild-type DAN1 promoter from S. cerevisiae

<400> SEQUENCE: 11
agctcaattc acgctggatt cggcgatccg ttttcttcaa tcctcacgtg ctttcttcgt    60
```

```
ttgagtgcaa aagttcatat gatgctatct cccgcttatc ttattagtcg aaaatgggga    120
gaatttccta ttttatctgt cgtttagcac atatggccag gaaaatacat aaggtttcgc    180
cgaacgacgg ggtcaattcg tccttttgt acacatcgtt taatttatga ggaaaaattg     240
atgaatgtat cctccgtaga cgctcctctg aaaagtttca tgtttcctgc gcgttccttt    300
gataggcaat aaaacaatac aacgcgtgcc tttgaaaatg ccaagatcta tacgaggcct    360
ctaacaaaac atcgttcagg aacagagaat gctagaaatg caaaagggtc cctgggtact    420
cattgaatag aaatgattga aaatactgcg tataaaatag cacgactaaa tgatactatt    480
tttatgtcga cacggtacta tttcttcttt ttcagataaa agtgtagcat actaaatata    540
taccccaagt a                                                         551
```

<210> SEQ ID NO 12
<211> LENGTH: 1253
<212> TYPE: DNA
<213> ORGANISM: Hansenula polymorpha
<220> FEATURE:
<221> NAME/KEY: misc_feature
<222> LOCATION: (1)..(1253)
<223> OTHER INFORMATION: MAL1 promoter

<400> SEQUENCE: 12

```
gatgatggac actagtgtgt cgagaatgta tcaactatat atagtcctaa tgccacacaa    60
atatgaagtg ggggaagccc attcttaatc cggctcaatt ttggtgcgtg atcgcggcct    120
atgtttgctt ccagaaaaag cttagaataa tatttctcac ctttgatgga atgctcgcga    180
gtgctcgttt tgattacccc atatgcattg ttgcagcatg caagcactat tgcaagccac    240
gcatggaaga aatttgcaaa cacctatagc cccgcgttgt tgaggaggtg gacttggtgt    300
aggaccataa agctgtgcac tactatggtg agctctgtcg tctggtgacc ttctatctca    360
ggcacatcct cgttttttgtg catgaggttc gagtcacgcc cacggcctat taatccgcga    420
aataaatgcg aaatctaaat tatgacgcaa ggctgagaga ttctgacacg ccgcatttgc    480
ggggcagtaa ttatcgggca gttttccggg gttcgggatg gggtttggag agaaagttca    540
acacagacca aaacagcttg ggaccacttg gatgcaggtc cccgcagaag agctctggcg    600
cgttggacaa acattgacaa tccacggcaa aattgtctac agttccgtgt atgcggatag    660
ggatatcttc gggagtatcg caataggata caggcactgt gcagattacg cgacatgata    720
gctttgtatg ttctacagac tctgccgtag cagtctagat ataatatcgg agttttgtag    780
cgtcgtaagg aaaacttggg ttacacaggt tccttgagag ccctttgacg ttgattgctc    840
tggcttccat ccaggccctc atgtggttca ggtgcctccg cagtggctgg caagcgtggg    900
ggtcaattac gtcacttcta ttcatgtacc ccagactcaa ttgttgacag caatttcagc    960
gagaattaaa ttccacaatc aattctcgct gaaataatta ggccgtgatt taattctcgc   1020
tgaaacagaa tcctgtctgg ggtacagata acaatcaagt aactattatg gacgtgcata   1080
ggaggtggag tccatgacgc aaagggaaat attcatttta tcctcgcgaa gttgggatgt   1140
gtcaaagcgt cgcgctcgct atagtgatga gaatgtcttt agtaagctta agccatataa   1200
agaccttccg cctccatatt ttttttttatc cctcttgaca atattaattc ctt          1253
```

<210> SEQ ID NO 13
<211> LENGTH: 1253
<212> TYPE: DNA
<213> ORGANISM: Hansenula polymorpha
<220> FEATURE:
<221> NAME/KEY: misc_feature
<222> LOCATION: (1)..(1253)
<223> OTHER INFORMATION: MAL2 promoter

<400> SEQUENCE: 13

```
aaggaattaa tattgtcaag agggataaaa aaaatatgg aggcggaagg tctttatatg    60
gcttaagctt actaaagaca ttctcatcac tatagcgagc gcgacgcttt gacacatccc   120
aacttcgcga ggataaaatg aatatttccc tttgcgtcat ggactccacc tcctatgcac   180
gtccataata gttacttgat tgttatctgt accccagaca ggattctgtt tcagcgagaa   240
ttaaatcacg gcctaattat ttcagcgaga attgattgtg gaatttaatt ctcgctgaaa   300
ttgctgtcaa caattgagtc tggggtacat gaatagaagt gacgtaattg accccacgc    360
ttgccagcca ctgcggaggc acctgaacca catgagggcc tggatggaag ccagagcaat   420
caacgtcaaa gggctctcaa gaaacctgtg taacccaagt tttccttacg acgctacaaa   480
actccgatat tatatctaga ctgctacggc agagtctgta gaacatacaa agctatcatg   540
tcgcgtaatc tgcacagtgc ctgtatccta ttgcgatact cccgaagata tccctatccg   600
catacacgga actgtagaca attttgccgt ggattgtcaa tgtttgtcca acgcgccaga   660
gctcttctgc ggggacctcc atccaagtgg tcccaagctg ttttggtctg tgttgaactt   720
tctctccaaa ccccatcccg aaccccggaa aactgcccga taattactgc cccgcaaatg   780
cggcgtgtca gaatctctca gccttgcgtc ataatttaga tttcgcattt atttcgcgga   840
ttaataggcc gtgggcgtga ctcgaacctc atgcacaaaa acgaggatgt gcctgagata   900
gaaggtcacc agacgacaga gctcaccata gtagtgcaca gctttatggt cctacaccaa   960
gtccacctcc tcaacaacgc ggggctatag gtgtttgcaa atttcttcca tgcgtggctt  1020
gcaatagtgc ttgcatgctg caacaatgca tgggggtaa tcaaaacgag cactcgcgag   1080
cattccatca aggtgagaa atattattct aagcttttc tggaagcaaa cataggccgc   1140
gatcacgcac caaaattgag ccggattaag aatgggcttc ccccacttca tatttgtgtg  1200
gcattaggac tatatatagt tgatacattc tcgacacact agtgtccatc atc          1253
```

<210> SEQ ID NO 14
<211> LENGTH: 785
<212> TYPE: DNA
<213> ORGANISM: S. cerevisiae
<220> FEATURE:
<221> NAME/KEY: misc_feature
<222> LOCATION: (1)..(785)
<223> OTHER INFORMATION: MAL11 promoter

<400> SEQUENCE: 14

```
ttatgtaatt tagttacgct tgactgatgt acatttgaga ttatcaaaaa aactgcttaa    60
gagatggatg atttaatttt ttagagacgt attaatggaa cttttttatac cttgcccaga   120
gcgcctcaag aaaatgatgc tgcaagaaga attgaggaag gaactattca tcttacgttg   180
tttgtatcat cccacgatcc aaatcatgtt acctacgtta ggtacgctag gaactaaaaa   240
aagaaaagaa aagtatgcgt tatcactctt cgagccaatt cttaattgtg tggggtccgc   300
gaaaatttcc ggataaatcc tgtaaacttt aacttaaacc ccgtgtttag cgaaattttc   360
aacgaagcgc gcaataagga gaaatattat ctaaaagcga gagtttaagc gagttgcaag   420
aatctctacg gtacagatgc aacttactat agccaaggtc tattcgtatt actatggcag   480
cgaaaggagc tttaaggttt taattacccc atagccatag attctactcg gtctatctat   540
catgtaacac tccgttgatg cgtactagaa aatgacaacg taccgggctt gagggacata   600
```

```
cagagacaat tacagtaatc aagagtgtac ccaactttaa cgaactcagt aaaaaataag    660
gaatgtcgac atcttaattt tttatataaa gcggtttggt attgattgtt tgaagaattt    720
tcgggttggt gtttctttct gatgctacat agaagaacat caaacaacta aaaaaatagt    780
ataat                                                                785

<210> SEQ ID NO 15
<211> LENGTH: 785
<212> TYPE: DNA
<213> ORGANISM: S. cerevisiae
<220> FEATURE:
<221> NAME/KEY: misc_feature
<222> LOCATION: (1)..(785)
<223> OTHER INFORMATION: MAL12 promoter

<400> SEQUENCE: 15
attatactat ttttttagtt gtttgatgtt cttctatgta gcatcagaaa gaaacaccaa     60
cccgaaaatt cttcaaacaa tcaataccaa accgctttat ataaaaaatt aagatgtcga    120
cattccttat tttttactga gttcgttaaa gtgggtaca ctcttgatta ctgtaattgt    180
ctctgtatgt ccctcaagcc cggtacgttg tcattttcta gtacgcatca acggagtgtt    240
acatgataga tagaccgagt agaatctatg gctatgggga aattaaaacc ttaaagctcc    300
tttcgctgcc atagtaatac gaatagacct tggctatagt aagttgcatc tgtaccgtag    360
agattcttgc aactcgctta aactctcgct tttagataat atttctcctt attgcgcgct    420
tcgttgaaaa tttcgctaaa cacggggttt aagttaaagt ttacaggatt tatccggaaa    480
ttttcgcgga ccccacacaa ttaagaattg gctcgaagag tgataacgca tacttttctt    540
ttcttttttt agttcctagc gtacctaacg taggtaacat gatttggatc gtgggatgat    600
acaaacaacg taagatgaat agttccttcc tcaattcttc ttgcagcatc attttcttga    660
ggcgctctgg gcaaggtata aaaagttcca ttaatacgtc tctaaaaaat taaatcatcc    720
atctcttaag cagttttttt gataatctca aatgtacatc agtcaagcgt aactaaatta    780
cataa                                                                785

<210> SEQ ID NO 16
<211> LENGTH: 875
<212> TYPE: DNA
<213> ORGANISM: S. cerevisiae
<220> FEATURE:
<221> NAME/KEY: misc_feature
<222> LOCATION: (1)..(875)
<223> OTHER INFORMATION: MAL31 promoter from S. cerevisiae

<400> SEQUENCE: 16
ttatgtattt tagttacgct tgactgatgt acatttgaga ttatcaaaaa aactgcttaa     60
gagatagatg gtttaatttt ttagagacgt attaatggaa cttttttatac cttgcccaga    120 gcgcctcaag aaaatgatgc tgaaagaaga attgaggaag gaactactca tcttacgttg    180
tttgtatcat cccacgatcc aaatcatgtt acctacgtta ggtacgctag gaactgaaaa    240
aagaaaagaa agtatgcgt tatcactctt cgagccaatt cttaattgtg tggggtccgc    300
gaaaacttcc ggataaatcc tgtaaactta aacttaaacc ccgtgtttag cgaaattttc    360
aacgaagcgc gcaataagga gaaatattat ataaaagcga gagtttaagc gaggttgcaa    420
gaatctctac ggtacagatg caacttacta tagccaaggt ctattcgtat tggtatccaa    480
gcagtgaagc tactcagggg aaaacatatt ttcagagatc aaagttatgt cagtctcttt    540
ttcatgtgta acttaacgtt tgtgcaggta tcataccggc ctccacataa tttttgtggg    600
```

```
gaagacgttg ttgtagcagt ctccttatac tctccaacag gtgtttaaag acttcttcag    660
gcctcatagt ctacatctgg agacaacatt agatagaagt ttccacagag gcagctttca    720 atatacttc ggctgtgtac atttcatcct gagtgagcgc atattgcata agtactcagt    780
atataaagag acacaatata ctccatactt gttgtgagtg gttttagcgt attcagtata    840
acaataagaa ttacatccaa gactattaat taact                              875

<210> SEQ ID NO 17
<211> LENGTH: 875
<212> TYPE: DNA
<213> ORGANISM: S. cerevisiae
<220> FEATURE:
<221> NAME/KEY: misc_feature
<222> LOCATION: (1)..(875)
<223> OTHER INFORMATION: MAL32 promoter from S. cerevisiae

<400> SEQUENCE: 17
agttaattaa tagtcttgga tgtaattctt attgttatac tgaatacgct aaaaccactc     60
acaacaagta tggagtatat tgtgtctctt tatatactga gtacttatgc aatatgcgct    120
cactcaggat gaaatgtaca cagccgaaag tatattgaaa gctgcctctg tggaaacttc    180
tatctaatgt tgtctccaga tgtagactat gaggcctgaa gaagtcttta aacacctgtt    240
ggagagtata aggagactgc tacaacaacg tcttccccac aaaaattatg tggaggccgg    300
tatgatacct gcacaaacgt taagttacac atgaaaaaga gactgacata actttgatct    360
ctgaaaatat gttttcccct gagtagcttc actgcttgga taccaatacg aatagacctt    420
ggctatagta agttgcatct gtaccgtaga gattcttgca acctcgctta aactctcgct    480
tttatataat atttctcctt attgcgcgct tcgttgaaaa tttcgctaaa cacggggttt    540
aagtttaagt ttacaggatt tatccggaag ttttcgcgga ccccacacaa ttaagaattg    600
gctcgaagag tgataacgca tacttttctt ttcttttttc agttcctagc gtacctaacg    660
taggtaacat gatttggatc gtgggatgat acaaacaacg taagatgagt agttccttcc    720
tcaattcttc tttcagcatc attttcttga ggcgctctgg gcaaggtata aaaagttcca    780
ttaatacgtc tctaaaaaat taaaccatct atctcttaag cagttttttt gataatctca    840
aatgtacatc agtcaagcgt aactaaaata cataa                              875
```

METHODS FOR STABILIZING PRODUCTION OF ACETYL-COENZYME A DERIVED COMPOUNDS

CROSS-REFERENCE TO RELATED APPLICATIONS

This application is a divisional of U.S. patent application Ser. No. 14/910,240, filed on Feb. 4, 2016, entitled "METHODS FOR STABILIZING PRODUCTION OF ACETYL-COENZYME A DERIVED COMPOUNDS," which is a U.S. National Stage of International Patent Application No. PCT/US2013/054028, filed on Aug. 7, 2013 and published as WO 2015/020649 A1 on Feb. 12, 2015, entitled "METHODS FOR STABILIZING PRODUCTION OF ACETYL-COENZYME A DERIVED COMPOUNDS," each of which is incorporated herein by reference in its entirety.

1. TECHNICAL FIELD

The present disclosure relates to the use of an oxygen responsive promoter as a genetic switch for modulating the production of heterologous non-catabolic compounds by a genetically modified host cell.

2. BACKGROUND OF THE INVENTION

The advent of synthetic biology has brought about the promise of fermentative microbial production of biofuels, chemicals and biomaterials from renewable sources at industrial scale and quality. For example, functional non-native biological pathways have been successfully constructed in microbial hosts for the production of precursors to the antimalarial drug artemisinin (see, e.g., Martin et al., *Nat Biotechnol* 21:796-802 (2003); fatty acid derived fuels and chemicals (e.g., fatty esters, fatty alcohols and waxes; see, e.g., Steen et al., *Nature* 463:559-562 (2010); polyketide synthases that make cholesterol lowering drugs (see, e.g., Ma et al., *Science* 326:589-592 (2009); and polyketides (see, e.g., Kodumal, *Proc Natl Acad Sci USA* 101:15573-15578 (2004). However, the commercial success of synthetic biology will depend largely on whether the production cost of renewable products can be made to compete with, or outcompete, the production costs of their respective non-renewable counterparts.

Strain stability can be a major driver of the cost of industrial fermentations, as it affects the length of time that a continuous fermentation can be run productively. Strain stability generally refers to the ability of a microbe to maintain favorable production characteristics (i.e., high yield (grams of compound per gram of substrate) and productivity (grams per liter of fermentation broth per hour)) of a non-catabolic fermentation product over extended cultivation times. In particular, genetic stability, which is the propensity of the producing microbial population to have little to no alteration of the intended allelic frequency of genes relevant to the production of product over time, plays a major role in the sustained output of product.

For non-catabolic fermentation of products other than biomass (which products, by definition, consume metabolic energy and carbon that could otherwise be used in the production of more cells), the basis of instability is two-fold: evolutionary mutation and selection. First, loss-of-production mutations arise spontaneously and randomly. Second, a growth rate or "fitness" advantage of cells with reduced product yields leads to an eventual population sweep by low producers, and thereby decreases the overall culture performance. This phenomenon can be referred to as "strain degeneration."

Brazilian fuel ethanol fermentations achieve extremely high yields of ethanol from sugar for long periods of time, i.e., about 90% of maximum theoretical yield. This is in part because the production of ethanol is catabolic: it generates 2 ATP per molecule of sugar produced and is redox balanced without the involvement of oxygen. A cell that mutates to not produce ethanol is less fit under the low oxygen conditions of the fermentor and will not sweep the population. This allows industrial ethanol fermentations to recycle the majority of yeast biomass throughout the season, thereby minimizing conversion of sugar into yeast cell biomass and directing nearly all of the sugar to ethanol production. This extended propagation and re-use of biomass increases the efficiencies of ethanol production: operational expenditures are reduced because less sugar goes to biomass during each cycle (i.e., the yield increases); and capital expenditures are reduced because fewer and smaller fermentors are needed to build biomass for inoculations.

By contrast, the production of many acetyl-CoA derived hydrocarbons (e.g., isoprenoids, fatty acids, and polyketides) are generally non-catabolic in nature; they usually require a net input of ATP, NADPH, and carbon, often with large amounts of oxygen supplied to help balance the redox of the system. Such an environment makes evolution towards lower product, higher biomass yielding genotypes more favorable, and leads to a higher rate of strain degeneration.

One way to decrease the negative selective pressure of producing non-catabolic products is to switch off the formation of product during periods where the product is not desired, such as during phases of the fermentation where biomass must be generated in order to maximize fermentor productivity. Thus, there is a need in the art for switches that can control the timing of production of acetyl-CoA derived compounds during fermentation.

3. SUMMARY OF THE INVENTION

Provided herein are fermentation processes for producing a heterologous non-catabolic compound from a genetically modified host cell. In some embodiments, the processes comprise two phases: a build stage during which non-catabolic compound production is substantially reduced (the "off" stage) while cell biomass is accumulated; and a production phase, during which non-catabolic compound production is turned on. Thus, the negative selective pressure associated with non-catabolic compound production is alleviated during a stage of fermentation in which production is not needed. The reduction or elimination of the non-catabolic compound production during the build stage results in (i) an improved growth rate of the cells during the build stage; and (ii) improved production stability of the strain during the production stage. This results in longer sustained non-catabolic compound production, thereby increasing the overall yield and/or productivity of the strain. Advantageously, the "off" and "on" states of non-catabolic compound production in the fermentation methods provided herein are controlled through easily obtained, affordable, and industrially relevant conditions.

In one aspect, the "off" and "on" states of non-catabolic compound production in the fermentation culture are controlled by the oxygen levels during fermentation, e.g., the amount of dissolved oxygen in the culture medium, in conjunction with the use of oxygen-sensitive promoters which drive gene expression of pathway enzymes that effect heterologous non-catabolic compound production. These methods take advantage of the observation that oxygen can be provided in limited amounts when culturing cells engineered to produce heterologous non-catabolic compounds. These cells can maintain growth and viability under microaerobic conditions, thereby saving costs associated with running a fully aerobic fermentation process. In some embodiments, microaerobic conditions can be achieved once the host cell population reaches a density sufficient to consume oxygen as fast as oxygen is being supplied. Advantageously, by coupling pathway gene expression to oxygen sensitive promoters, compound production is turned on only when oxygen consumption by the host cell population is high enough to achieve microaerobic conditions in the fermentor, which effectively occurs at the end of the build stage, that is, when optimal cell densities have been achieved for efficient compound production. Thus, pathway gene expression is tightly coupled to achieving a population density that is ideal for the start of the production phase. Accordingly, the methods provided herein utilize oxygen levels and a genetic switch to effect the "off" and "on" stages of an improved fermentation process for production of heterologous non-catabolic compounds.

Thus, provided herein is a method for producing a heterologous non-catabolic compound in a genetically modified host cell, the method comprising:
(a) culturing a population of genetically modified host cells in a culture medium comprising a carbon source under aerobic conditions, wherein the host cell comprises one or more heterologous nucleic acids encoding one or more enzymes of an enzymatic pathway for making the heterologous non-catabolic compound, wherein expression of the one or more enzymes is positively regulated by the activity of a microaerobic-responsive promoter, wherein the aerobic conditions limit the amount of heterologous non-catabolic compound produced by the host cells; and
(b) culturing said population or a subpopulation thereof in a culture medium comprising a carbon source under microaerobic conditions, wherein said microaerobic conditions increases the production of the non-catabolic compound by said population or subpopulation thereof.

In some embodiments, the microaerobic-responsive promoter is a mutated DAN1 promoter. In some embodiments, the mutated DAN1 promoter comprises a sequence selected from the group consisting of SEQ ID NOs: 1, 2, 3, 4, 5, 6, 7, 8, 9 and 10. In some embodiments, the mutated DAN1 promoter sequence comprises SEQ ID NO: 1. In some embodiments, the mutated DAN1 promoter sequence comprises SEQ ID NO:2.

In some embodiments, the microaerobic-responsive promoter is operably linked to the one or more heterologous nucleic acids encoding the one or more enzymes of the enzymatic pathway, and said microaerobic conditions increase the expression of the one or more enzymes of the enzymatic pathway. In some embodiments, the microaerobic-responsive promoter is operably linked to a heterologous nucleic acid encoding a transcriptional regulator that positively regulates the expression of the one or more heterologous nucleic acids encoding one or more enzymes of the enzymatic pathway, and said microaerobic conditions increase the expression of the transcriptional regulator. In some embodiments, the transcriptional regulator is Gal4p, and the one or more heterologous nucleic acids encoding the one or more enzymes of the enzymatic pathway are each operably linked to a Gal4p-responsive promoter selected from the group consisting of pGAL1, pGAL7 and pGAL10.

In some embodiments, the host cell further comprises a functional disruption of Gal80p.

In some embodiments, the microaerobic conditions comprise a dissolved oxygen concentration in the culture medium of less than about 20%, less than about 15%, less than about 10%, or less than about 5%. In some embodiments, the microaerobic conditions comprise a dissolved oxygen concentration in the culture medium of about 0%. In some embodiments, the microaerobic conditions result in an oxygen uptake rate of the host cells of less than about 50 mmoles, less than about 40 mmoles, less than about 30 mmoles, less than about 20 mmoles per liter of medium, or less than about 10 mmoles per liter of medium. In some embodiments, the microaerobic conditions result in a specific oxygen uptake rate of the host cells of less than about 30 mmoles, less than about 25 mmoles, less than about 20 mmoles, less than about 15 mmoles, less than about 10 mmoles, or less than about 5 mmoles per gram of dry cell weight per hour.

In some embodiments, heterologous non-catabolic compound production by the population of genetically modified host cell over the duration of culturing of step (b) is improved compared to that achieved in an aerobic fermentation process wherein expression of the one or more enzymes of the enzymatic pathway is not limited by the activity of the microaerobic-responsive promoter.

Also provided herein is a method for producing a heterologous isoprenoid in a genetically modified host cell, the method comprising:
(a) culturing a population of genetically modified host cells in a culture medium comprising a carbon source under aerobic conditions, wherein the host cell comprises:
(i) one or more heterologous nucleic acids encoding one or more enzymes of the mevalonate (MEV) pathway, each operably linked to a Gal4p-responsive promoter selected from the group consisting of pGAL1, pGAL7 and pGAL10; and
(ii) a nucleic acid encoding Gal4p, operably linked to a microaerobic-responsive promoter; wherein the aerobic conditions limit the amount of heterologous isoprenoid produced by the host cells; and
(b) culturing said population or a subpopulation thereof in a culture medium comprising a carbon source under microaerobic conditions, wherein said microaerobic conditions increases the production of heterologous isoprenoid by said population or subpopulation thereof.

In another aspect, the "off" and "on" states of non-catabolic compound production in the fermentation culture are controlled by the amount of the sugar maltose in the culture medium, in conjunction with the use of maltose-responsive promoters which regulate gene expression of pathway enzymes that effect heterologous non-catabolic compound production.

Advantageously, by coupling pathway gene expression to maltose-sensitive promoters, compound production can be turned on or off by controlling the amount of maltose in the feedstock. For example, a maltose-responsive promoter can be wired as an "on" switch to induce production of the heterologous non-catabolic compound in the presence of maltose. Alternatively a maltose-responsive promoter can be wired as an "off" switch to induce expression of a negative regulator of the enzymatic pathway for compound production in the presence of maltose. Accordingly, the methods provided herein utilize maltose levels in the culture medium and a genetic switch to effect the "off" and "on" stages of an improved fermentation process for production of heterologous non-catabolic compounds.

Thus, provided herein is a method for producing a heterologous non-catabolic compound in a genetically modified host cell, the method comprising:
- (a) culturing a population of genetically modified host cells in a culture medium comprising a carbon source comprising maltose, wherein the host cell comprises one or more heterologous nucleic acids encoding one or more enzymes of an enzymatic pathway for making the heterologous non-catabolic compound, wherein expression of the one or more enzymes is negatively regulated by the activity of a maltose-responsive promoter, wherein the presence of maltose in the culture medium limits the amount of heterologous non-catabolic compound produced by the host cells; and
- (b) culturing said population or a subpopulation thereof in a culture medium comprising a carbon source wherein maltose is absent or in sufficiently low amounts such that the maltose-responsive promoter is no longer active, and production of the heterologous non-catabolic compound by the host cells is increased.

In some embodiments, the maltose-responsive promoter is operably linked to a heterologous nucleic acid encoding a transcriptional regulator that negatively regulates the expression of the one or more heterologous nucleic acids encoding the one or more enzymes of the enzymatic pathway, and the maltose in step (a) increases the expression of the transcriptional regulator. In some embodiments, the transcriptional regulator is Gal80p, the host cell further comprises Gal4p, and the one or more heterologous nucleic acids encoding the one or more enzymes of the enzymatic pathway are each operably linked to a Gal4p-responsive promoter selected from the group consisting of pGAL1, pGAL7 and pGAL10. In some embodiments, the maltose-responsive promoter comprises a sequence selected from the group consisting of pMAL1 (SEQ ID NO:12), pMAL2 (SEQ ID NO:13), pMAL11 (SEQ ID NO:14), pMAL12 (SEQ ID NO:15), pMAL31 (SEQ ID NO: 16) and pMAL32 (SEQ ID NO: 17). In some embodiments, the maltose-responsive promoter sequence comprises pMAL32 (SEQ ID NO:17).

In some embodiments, the culture medium of step (a) comprises at least 0.1% (w/v) maltose. In some embodiments, the culture medium of step (a) comprises 0.25% to 3% (w/v) maltose. In some embodiments, the culture medium of step (b) comprises no more than 0.08% (w/v) maltose. In some embodiments, heterologous non-catabolic compound production by the population of genetically modified host cell over the duration of culturing of step (b) is improved compared to that achieved in a fermentation process wherein expression of the one or more enzymes of the enzymatic pathway is not limited by the activity of the maltose-responsive promoter.

Also provided herein is a method for producing a heterologous isoprenoid in a genetically modified host cell, the method comprising:
- (a) culturing a population of genetically modified host cells in a culture medium comprising a carbon source comprising maltose, wherein the host cell comprises:
  - (i) one or more heterologous nucleic acids encoding one or more enzymes of the mevalonate (MEV) pathway, each operably linked to a Gal4p-responsive promoter selected from the group consisting of pGAL1, pGAL7 and pGAL10;
  - (ii) a nucleic acid encoding Gal4p; and
  - (iii) a nucleic acid encoding Gal80p, operably linked to a maltose-responsive promoter; wherein the maltose in the culture medium limits the amount of heterologous isoprenoid produced by the host cells; and
- (b) culturing said population or a subpopulation thereof in a culture medium comprising a carbon source wherein maltose is absent or in sufficiently low amounts such that the maltose-responsive promoter is no longer active, and production of the heterologous non-catabolic compound by the host cells is increased.

In some embodiments, production of the non-catabolic compound during step (a) of the methods described herein is less than 50, 40, 30, 20 or 10% of the production of the non-catabolic compound during step (b). In some embodiments, the culturing of step (a) is for a period of at least 12, 24, 36, 48, 60, 72, 84, 96 or more than 96 hours. In some embodiments, the culturing of step (a) is for a period of time sufficient for said population to reach a cell density ($OD_{600}$) of between 0.01 and 400. In some embodiments, the culturing of step (b) is for a period of 3 to 20 days. In some embodiments, production of the non-catabolic compound is measured in terms of yield (gram of non-catabolic compound produced per gram of carbon substrate) or productivity (grams of non-catabolic compound produced per liter of culture medium per hour). In some embodiments, the method further comprises recovering the non-catabolic compound.

In another aspect, provided herein are fermentation compositions produced by the fermentation methods described herein. In some embodiments, the fermentation composition comprises a population of genetically modified host cells in a culture medium comprising a carbon source, wherein the host cell comprises one or more heterologous nucleic acids encoding one or more enzymes of an enzymatic pathway for making the heterologous non-catabolic compound, wherein expression of the one or more enzymes is positively regulated by the activity of a microaerobic-responsive promoter. In some embodiments, the microaerobic-responsive promoter is operably linked to the one or more heterologous nucleic acids encoding the one or more enzymes of the enzymatic pathway, wherein expression of the one or more enzymes of an enzymatic pathway is increased under microaerobic fermentation conditions. In some embodiments, the microaerobic-responsive promoter is operably linked to a heterologous nucleic acid encoding a transcriptional regulator that positively regulates the expression of the one or more heterologous nucleic acids encoding one or more enzymes of the enzymatic pathway, wherein expression of the transcriptional regulator is increased under microaerobic fermentation conditions. In some embodiments, the transcriptional regulator is Gal4p, and the one or more heterologous nucleic acids encoding the one or more enzymes of the enzymatic pathway are each operably linked to a Gal4p-responsive promoter selected from the group consisting of pGAL1, pGAL7 and pGAL10.

In some embodiments, the fermentation composition comprises a population of genetically modified host cells in a culture medium comprising a carbon source, wherein the host cell comprises: (a) one or more heterologous nucleic acids encoding one or more enzymes of the mevalonate (MEV) pathway, each operably linked to a Gal4p-responsive promoter; and (b) a nucleic acid encoding Gal4p, operably linked to a microaerobic-responsive promoter. In some embodiments, the host cell further comprises a functional disruption of Gal80p. In some embodiments, the microaerobic-responsive promoter is a mutated DAN1 promoter. In some embodiments, the mutated DAN1 promoter comprises a sequence selected from the group consisting of SEQ ID NOs: 1, 2, 3, 4, 5, 6, 7, 8, 9 and 10. In some embodiments, the mutated DAN1 promoter sequence comprises SEQ ID NO: 1. In some embodiments, the mutated DAN1 promoter sequence comprises SEQ ID NO:2. In some embodiments, the culture medium comprises a dissolved oxygen concentration of 100%. In some embodiments, the culture medium comprises a dissolved oxygen concentration of less than about 20%, less than about 15%, less than about 10%, or less than about 5%. In some embodiments, the culture medium comprises a dissolved oxygen concentration of about 0%.

In some embodiments, the fermentation composition comprises a population of genetically modified host cells in a culture medium comprising a carbon source, wherein the host cell comprises one or more heterologous nucleic acids encoding one or more enzymes of an enzymatic pathway for making the heterologous non-catabolic compound, wherein expression of the one or more enzymes is positively regulated by the activity of a maltose-responsive promoter. In some embodiments, the maltose-responsive promoter is operably linked to the one or more heterologous nucleic acids encoding the one or more enzymes of the enzymatic pathway, wherein expression of the one or more enzymes of an enzymatic pathway is decreased in the presence of maltose. In some embodiments, the maltose-responsive promoter is operably linked to a heterologous nucleic acid encoding a transcriptional regulator that negatively regulates the expression of the one or more heterologous nucleic acids encoding one or more enzymes of the enzymatic pathway, wherein expression of the transcriptional regulator is increased in the presence of maltose. In some embodiments, the transcriptional regulator is Gal80p, the host cell further comprises Gal4p, and the one or more heterologous nucleic acids encoding the one or more enzymes of the enzymatic pathway are each operably linked to a Gal4p-responsive promoter selected from the group consisting of pGAL1, pGAL7 and pGAL10.

In some embodiments, the fermentation composition comprises a population of genetically modified host cells in a culture medium comprising a carbon source, wherein the host cell comprises: (a) one or more heterologous nucleic acids encoding one or more enzymes of the mevalonate (MEV) pathway, each operably linked to a Gal4p-responsive promoter; (b) a nucleic acid encoding Gal4p; and (c) a nucleic acid encoding Gal80p, operably linked to a maltose-responsive promoter. In some embodiments, the maltose-responsive promoter comprises a sequence selected from the group consisting of pMAL1 (SEQ ID NO: 12), pMAL2 (SEQ ID NO:13), pMAL11 (SEQ ID NO:14), pMAL12 (SEQ ID NO:15), pMAL31 (SEQ ID NO:16) and pMAL32 (SEQ ID NO:17). In some embodiments, the maltose-responsive promoter sequence comprises pMAL32 (SEQ ID NO:17). In some embodiments, the culture medium comprises at least 0.1% (w/v) maltose. In some embodiments, the culture medium comprises 0.25% to 3% (w/v) maltose. In some embodiments, the culture medium comprises no more than 0.08% maltose.

In some embodiments, the host cell is selected from the group consisting of a fungal cell, a bacterial cell, a plant cell, and an animal cell. In some embodiments, the host cell is a yeast cell. In some embodiments, the non-catabolic compound is selected from the group consisting of an amino acid, a fatty acid, an isoprenoid, and a polyketide.

In some embodiments, the host cells are capable of producing an isoprenoid and comprises at least one heterologous nucleic acid encoding an isoprenoid pathway enzyme selected from the group consisting of: (a) an enzyme that condenses two molecules of acetyl-coenzyme A to form acetoacetyl-CoA; (b) an enzyme that condenses acetoacetyl-CoA with another molecule of acetyl-CoA to form 3-hydroxy-3-methylglutaryl-CoA (HMG-CoA); (c) an enzyme that converts HMG-CoA into mevalonate; (d) an enzyme that converts mevalonate into mevalonate 5-phosphate; (e) an enzyme that converts mevalonate 5-phosphate into mevalonate 5-pyrophosphate; (f) an enzyme that converts mevalonate 5-pyrophosphate into IPP; (g) an enzyme that converts IPP into DMAPP; (h) a polyprenyl synthase that can condense IPP and/or DMAPP molecules to form polyprenyl compounds containing more than five carbons; (i) an enzyme that condenses IPP with DMAPP to form GPP; (j) an enzyme that condenses two molecules of IPP with one molecule of DMAPP; (k) an enzyme that condenses IPP with GPP to form FPP; (l) an enzyme that condenses IPP and DMAPP to form GGPP; and (m) an enzyme that condenses IPP and FPP to form GGPP.

In some embodiments, the host cells further comprise a heterologous nucleic acid encoding an enzyme that modifies a polyprenyl, selected from the group consisting of a geraniol synthase, a linalool synthase, a limonene synthase, a myrcene synthase, an ocimene synthase, an α-pinene synthase, β-pinene synthase, a sabinene synthase, a γ-terpinene synthase, a terpinolene synthase, an amorphadiene synthase, an α-farnesene synthase, a β-farnesene synthase, a farnesol synthase, a nerolidol synthase, a patchouliol synthase, a nootkatone synthase, an abietadiene synthase.

In some embodiments, the host cells comprise a plurality of heterologous nucleic acids encoding all the enzymes of a mevalonate pathway. In some embodiments, the isoprenoid is selected from the group consisting of a hemiterpene, monoterpene, diterpene, triterpene, tetraterpene, and polyterpene. In some embodiments, the isoprenoid is a $C_5$-$C_{20}$ isoprenoid. In some embodiments, the isoprenoid is a sesquiterpene. In some embodiments, the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene and valencene.

In some embodiments, the host cells are capable of producing a polyketide and comprises at least one heterologous nucleic acid encoding a polyketide synthesis enzyme, wherein the polyketide synthesis enzyme is selected from the group consisting of: (a) an enzyme that condenses at least one of acetyl-CoA and malonyl-CoA with an acyl carrier protein; (b) an enzyme that condenses a first reactant selected from the group consisting of acetyl-CoA and malonyl-CoA with a second reactant selected from the group consisting of malonyl-CoA or methylmalonyl-CoA to form a polyketide product; (c) an enzyme that reduces a β-keto chemical group on a polyketide compound to a β-hydroxy group; (d) an enzyme that dehydrates an alkane chemical group in a polyketide compound to produce an α-β-unsaturated alkene; (e) an enzyme that reduces an α-β-double-bond in a polyketide compound to a saturated alkane; and (f) an enzyme that hydrolyzes a polyketide compound from an acyl carrier protein.

In some embodiments, the polyketide is a lipid having at least one of antibiotic, antifungal, and antitumor activity. In some embodiments, the polyketide is selected from the group consisting of a macrolid, an antibiotic, an antifungal, a cytostatic compound, an anticholesterolemic compound, an antiparasitic compound, a coccidiostatic compound, an animal growth promoter and an insecticide.

In some embodiments, the host cells are capable of producing a fatty acid and comprises at least one heterologous nucleic acid encoding a fatty acid synthesis enzyme, wherein the fatty acid synthesis enzyme is selected from the group consisting of: (a) an enzyme that covalently links at least one of acetyl-CoA and malonyl-CoA to an acyl carrier protein (ACP); (b) an enzyme that condenses acetyl-ACP and malonyl-ACP to form acetoacetyl-ACP; (c) reduce the double bond in acetoacetyl-ACP with NADPH to form a hydroxyl group in D-3-hydroxybutyryl hydroxylase-ACP; (d) an enzyme that dehydrates D-3-Hydroxybutyryl hydroxylase-ACP to create a double bond between the beta- and gamma-carbons forming crotonyl-ACP; (e) an enzyme that reduces crotonyl ACP with NADPH to form butyryl-ACP; and (f) an enzyme that hydrolyzes a C16 acyl compound from an acyl carrier protein to form palmitate. In some embodiments, the fatty acid is selected from the group consisting of palmitate, palmitoyl CoA, palmitoleic acid, sapienic acid, oleic acid, linoleic acid, α-linolenic acid, arachidonic acid, eicosapentaenoic acid, erucic acid, and docosahexaenoic acid.

4. BRIEF DESCRIPTION OF FIGURES

FIG. 1 provides a schematic representation of the mevalonate ("MEV") pathway for the production of isopentenyl diphosphate ("IPP").

Figure 2:
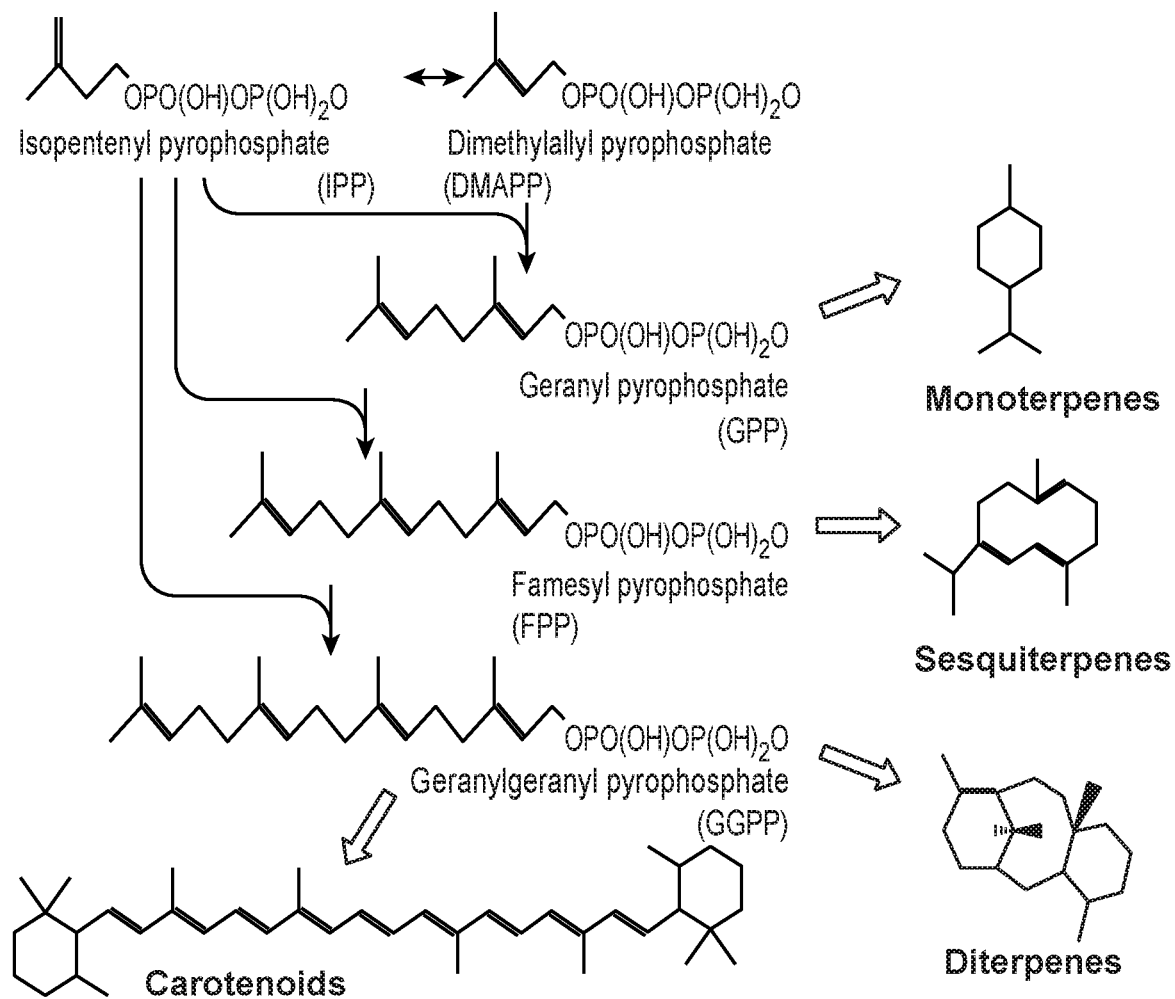

FIG. 2 provides a schematic representation of the conversion of IPP and dimethylallyl pyrophosphate ("DMAPP") to geranyl pyrophosphate ("GPP"), farnesyl pyrophosphate ("FPP"), and geranylgeranyl pyrophosphate ("GGPP").

Figure 3:
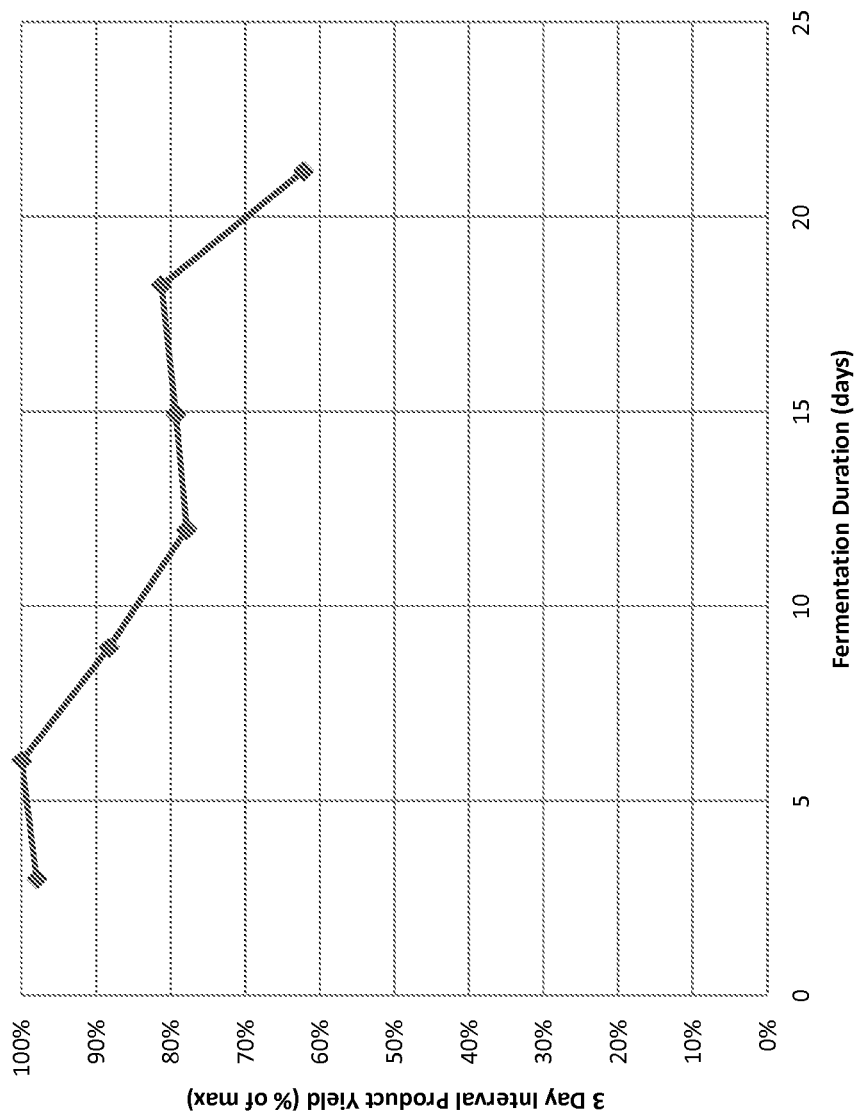

FIG. 3 shows strain degeneration (i.e., decline of non-catabolic compound production over time) of a population of yeast host cells capable of producing a non-catabolic compound, farnesene.

Figure 4:
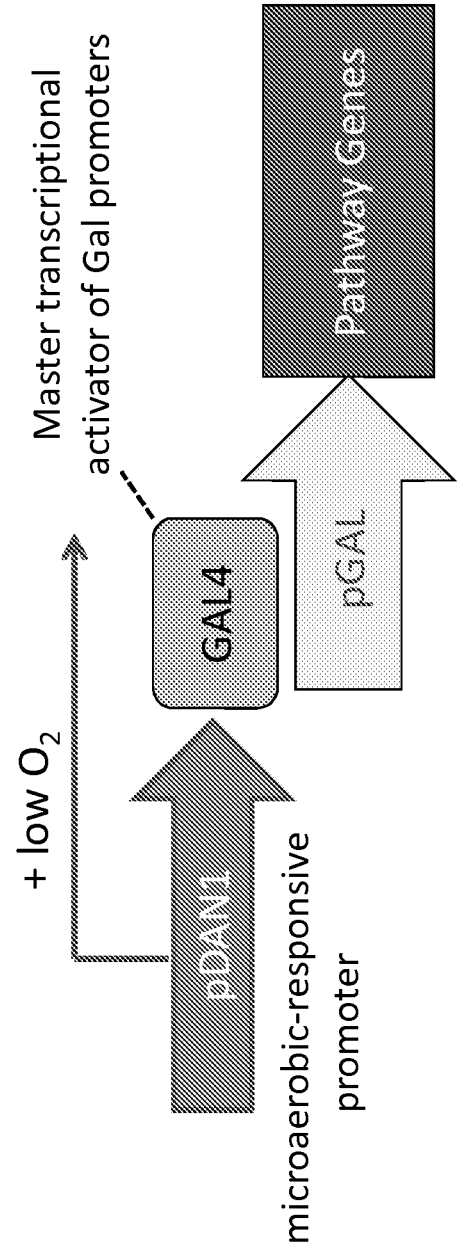

FIG. 4 provides a schematic representation of an exemplary GAL-regulon based low-oxygen switch for the control of heterologous non-catabolic compound production in a host cell.

Figure 5:
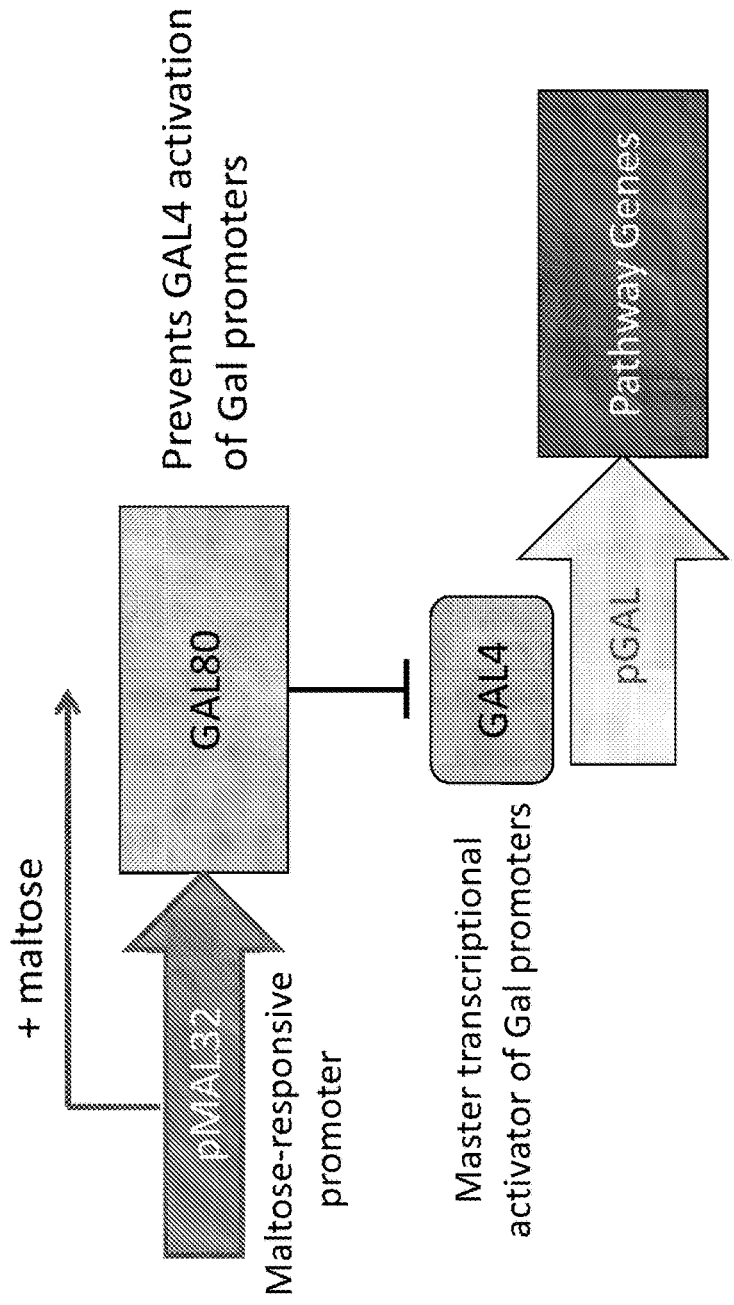

FIG. 5 provides a schematic representation of an exemplary GAL-regulon based maltose switch for the control of heterologous non-catabolic compound production in a host cell.

Figure 6:
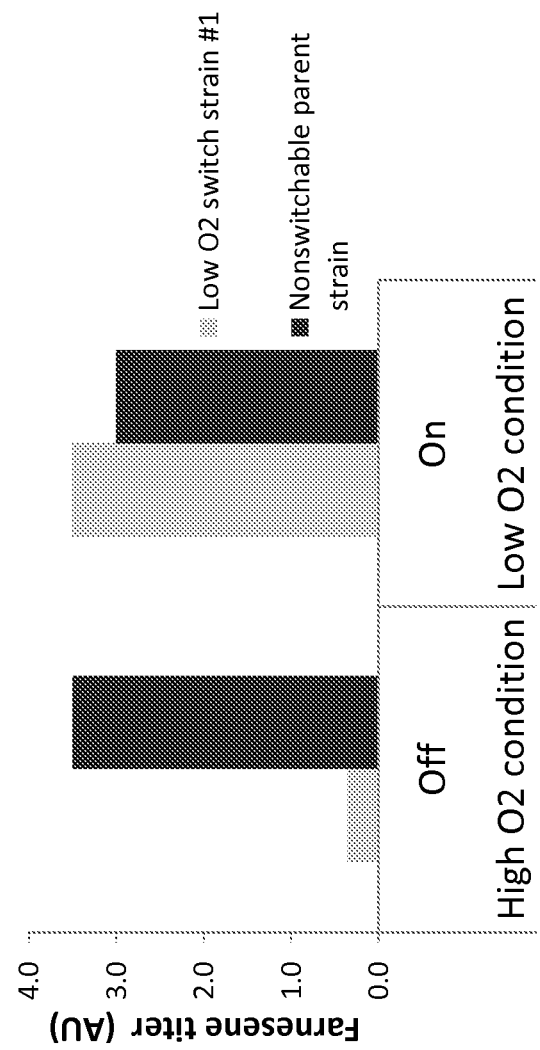

FIG. 6 provides results demonstrating that host cells capable of producing the isoprenoid farnesene, and comprising the MEV pathway under positive regulation by a microaerobic responsive promoter ("low $O_2$ switch"), produces very low amounts of farnesene in the high $O_2$ condition (shake plate), and in the low $O_2$ condition (shake flask with low RPM), production is substantially increased to levels matching the production of a nonswitchable parent strain in which the MEV pathway is constitutively expressed.

Figure 7:
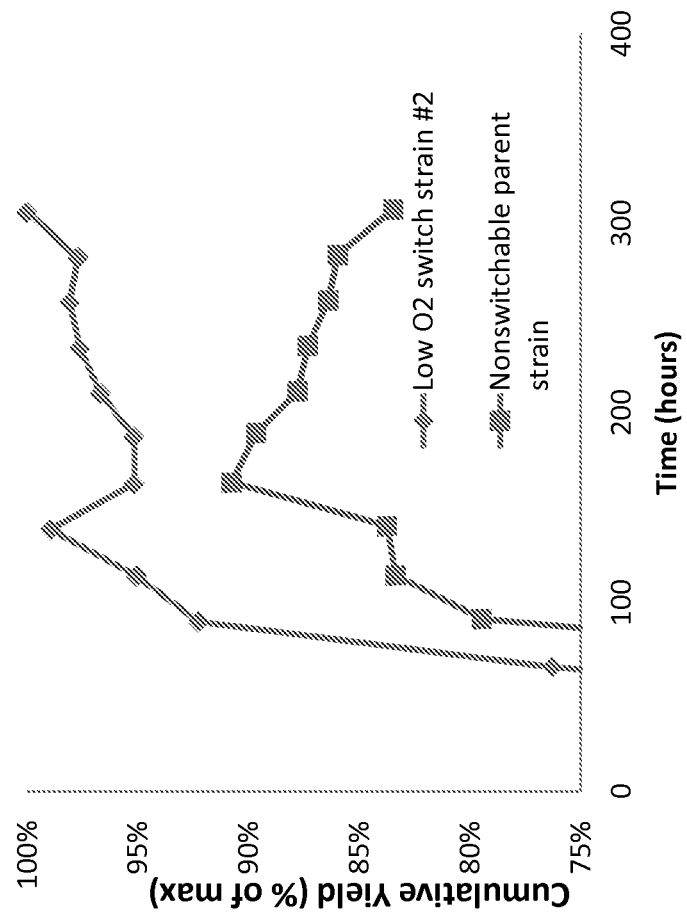

FIG. 7 provides results demonstrating that host cells capable of producing the isoprenoid farnesene, and comprising the MEV pathway under positive regulation by a low $O_2$ switch, display improved stability of production of farnesene in a long fermentation run when the build stage of the fermentation is performed under aerobic conditions (thereby effecting an "off" state) compared to production from a constitutively producing strain that produced farnesene throughout the build stage.

Figure 8:
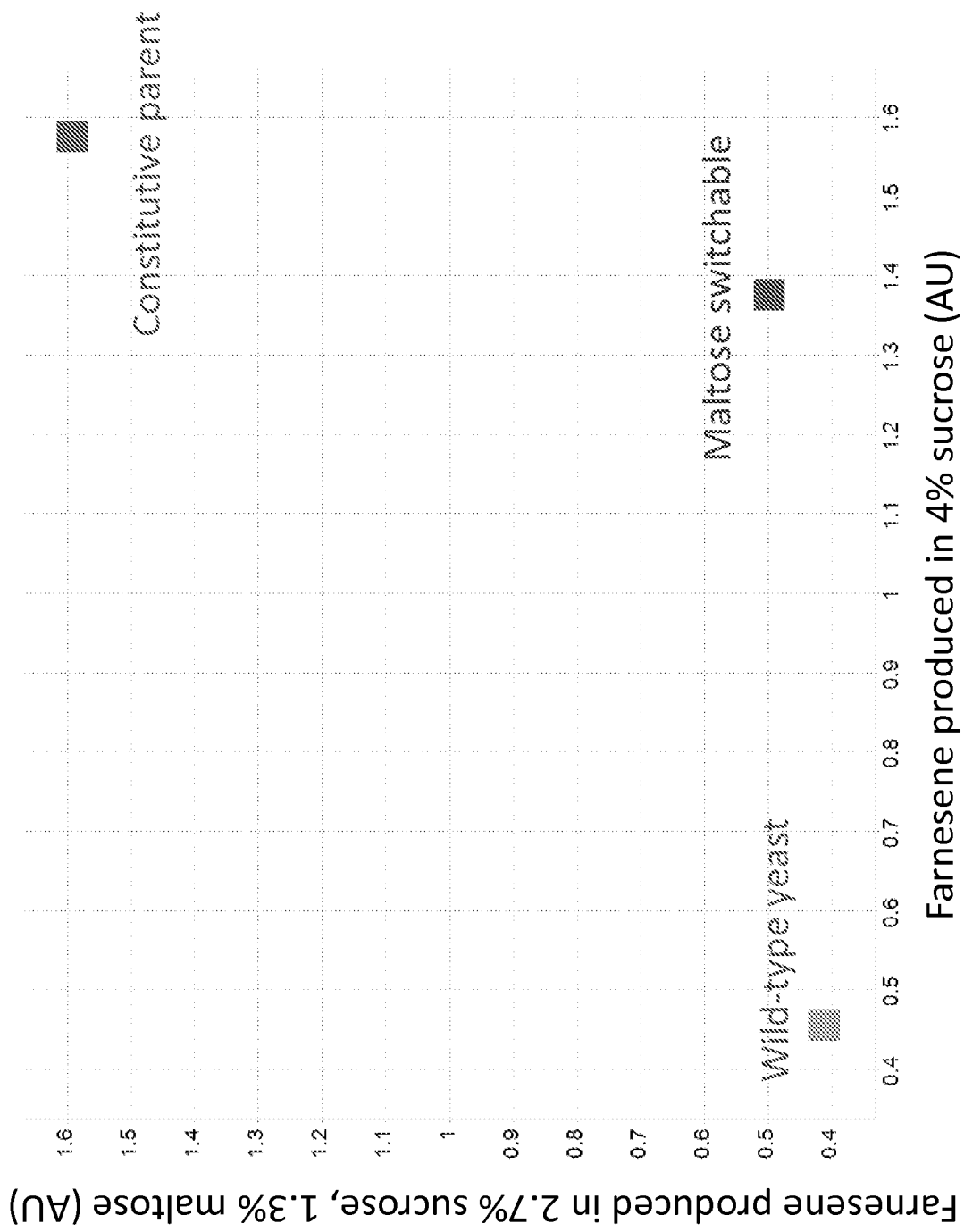

FIG. 8 provides results demonstrating that host cells capable of producing the isoprenoid farnesene, and comprising the MEV pathway under negative regulation by a maltose-responsive promoter ("maltose switch"), produce very low amounts of farnesene in the presence of maltose (1.3%), and in the absence of maltose, production is substantially increased to levels nearing the production of a non-switchable parent strain in which the MEV pathway is constitutively expressed.

Figure 9:
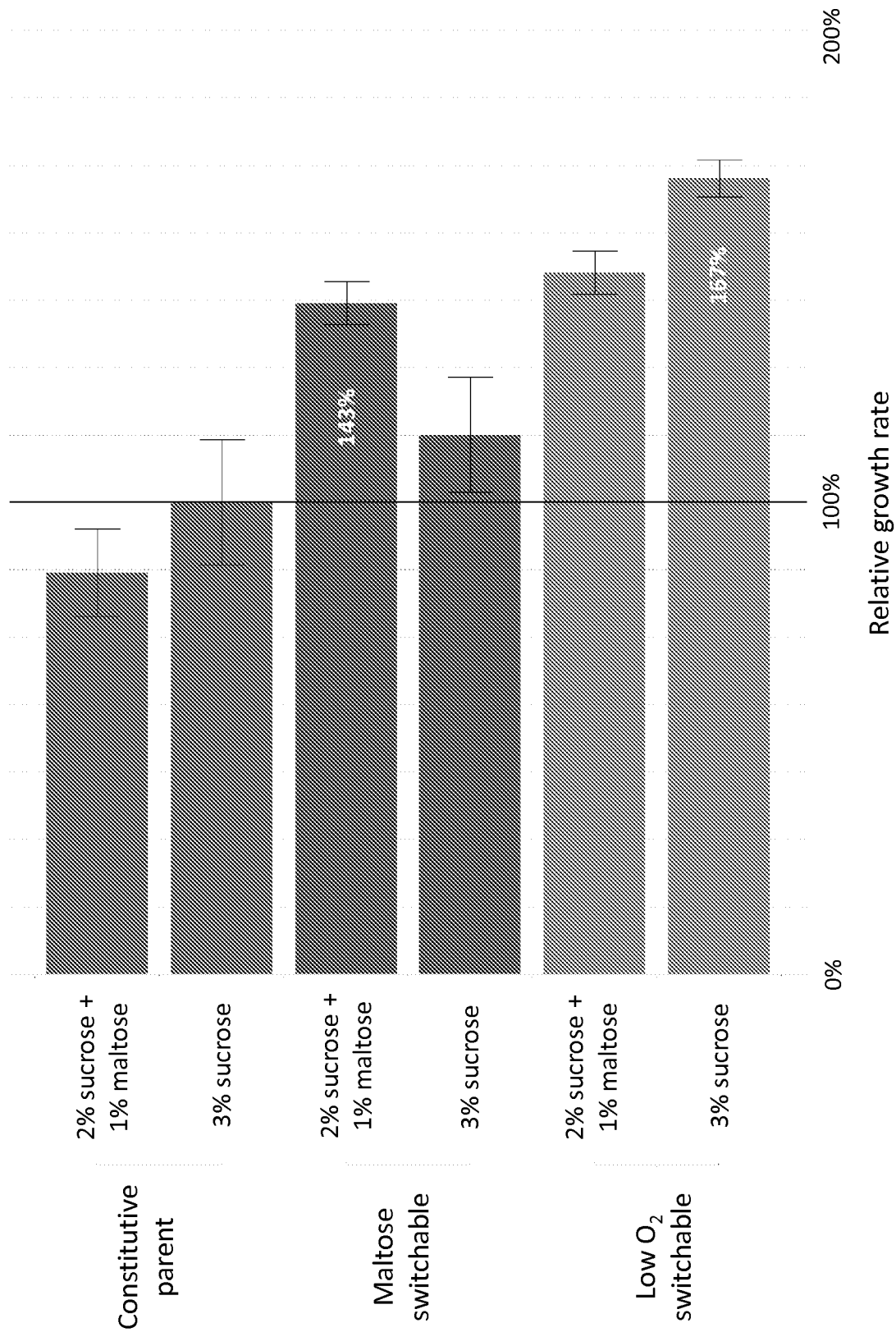

FIG. 9 provides results demonstrating that host cells capable of producing the isoprenoid farnesene, and comprising the MEV pathway either under (i) positive regulation by a microaerobic responsive promoter ("low $O_2$ switch"); or negative regulation by a maltose-responsive promoter ("maltose switch"), have improved growth rates during the "off" state of compound production compared to a parent strain constitutively producing farnesene.

Figure 10:
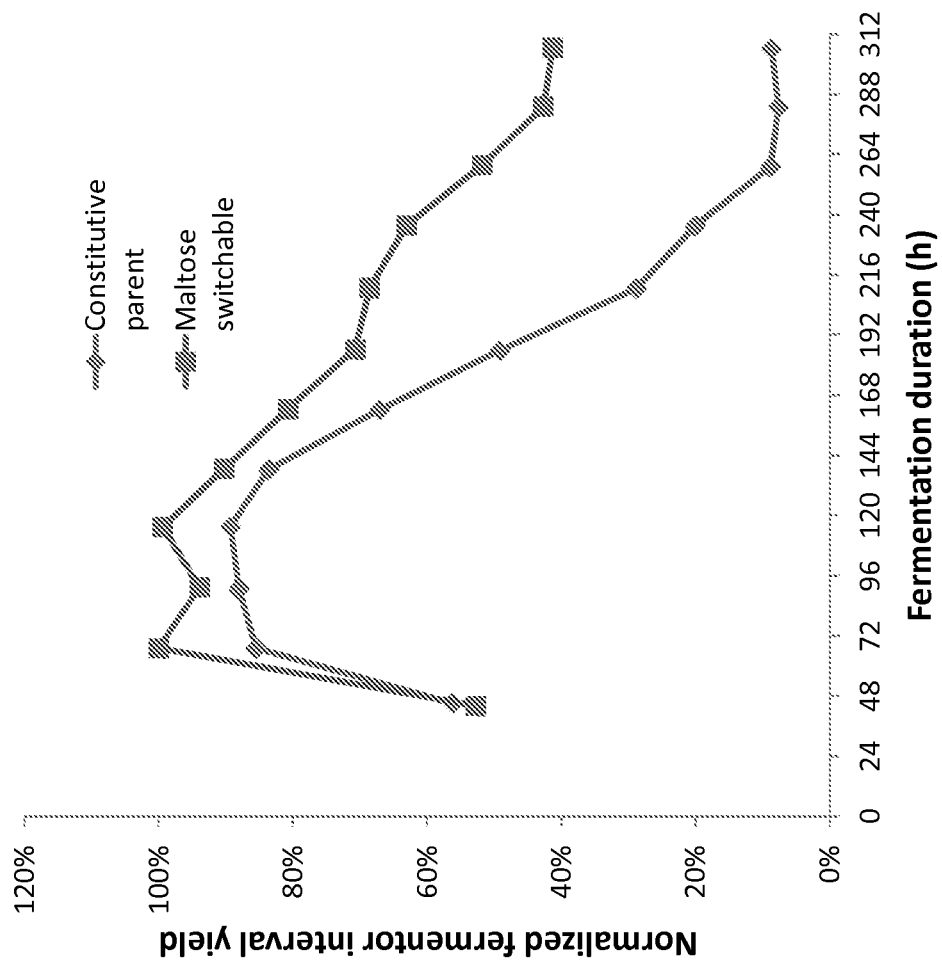

FIG. 10 provides results demonstrating that host cells capable of producing the isoprenoid farnesene, and comprising the MEV pathway under negative regulation by a maltose switch, display improved stability of production of farnesene in a long fermentation run when the build stage of the fermentation is performed in the presence of maltose (thereby effecting an "off" state), compared to production from a constitutively producing strain that produced farnesene throughout the build stage.

FIG. 11 provides results demonstrating, for the maltose-sensitive promoter pMAL11, (A) the sensitivity to varying amounts of maltose and to mixed feeds in the culture medium, and well as (B) to the switchability to the "on" state in the absence of maltose, following repression by maltose in the "off" state.

FIG. 12 provides results demonstrating, for the maltose-sensitive promoter pMAL12, (A) the sensitivity to varying amounts of maltose and to mixed feeds in the culture medium, and well as (B) to the switchability to the "on" state in the absence of maltose, following repression by maltose in the "off" state.

FIG. 13 provides results demonstrating, for the maltose-sensitive promoter pMAL31, (A) the sensitivity to varying amounts of maltose and to mixed feeds in the culture medium, and well as (B) to the switchability to the "on" state in the absence of maltose, following repression by maltose in the "off" state.

FIG. 14 provides results demonstrating, for the maltose-sensitive promoter pMAL32, (A) the sensitivity to varying amounts of maltose and to mixed feeds in the culture medium, and well as (B) to the switchability to the "on" state in the absence of maltose, following repression by maltose in the "off" state.

5. DESCRIPTION OF EMBODIMENTS

5.1 Definitions

As used herein, the term "endogenous" refers to a substance or process that can occur naturally in a host cell.

As used herein, the phrase to "functionally disrupt" or a "functional disruption" e.g., of a target gene means that the target gene is altered in such a way as to decrease in the host cell the activity of the protein encoded by the target gene. Similarly, to "functionally disrupt" or a "functional disruption" e.g., of a target protein means that the target protein is altered in such a way as to decrease in the host cell the activity of the protein. In some embodiments, the activity of the target protein encoded by the target gene is eliminated in the host cell. In other embodiments, the activity of the target protein encoded by the target gene is decreased in the host cell. Functional disruption of the target gene may be achieved by deleting all or a part of the gene so that gene expression is eliminated or reduced, or so that the activity of the gene product is eliminated or reduced. Functional disruption of the target gene may also be achieved by mutating a regulatory element of the gene, e.g., the promoter of the gene so that expression is eliminated or reduced, or by mutating the coding sequence of the gene so that the activity of the gene product is eliminated or reduced. In some embodiments, functional disruption of the target gene results in the removal of the complete open reading frame of the target gene.

As used herein, the term "genetically modified" denotes a host cell that comprises a heterologous nucleotide sequence.

As used herein, the term "heterologous" refers to what is not normally found in nature. The term "heterologous compound" refers to the production of a compound by a cell that does not normally produce the compound, or to the production of a compound at a level at which it is not normally produced by the cell.

As used herein, the phrase "heterologous enzyme" refers to an enzyme that is not normally found in a given cell in nature. The term encompasses an enzyme that is:
(a) exogenous to a given cell (i.e., encoded by a nucleotide sequence that is not naturally present in the host cell or not naturally present in a given context in the host cell); and
(b) naturally found in the host cell (e.g., the enzyme is encoded by a nucleotide sequence that is endogenous to the cell) but that is produced in an unnatural amount (e.g., greater or lesser than that naturally found) in the host cell.

As used herein, the phrase "operably linked" refers to a functional linkage between nucleic acid sequences such that the linked promoter and/or regulatory region functionally controls expression of the coding sequence.

As used herein, the term "production" generally refers to an amount of non-catabolic compound produced by a genetically modified host cell provided herein. In some embodiments, production is expressed as a yield of the non-catabolic compound by the host cell. In other embodiments, production is expressed as a productivity of the host cell in producing the non-catabolic compound.

As used herein, the term "productivity" refers to production of a non-catabolic compound by a host cell, expressed as the amount of non-catabolic compound produced (by weight) per amount of fermentation broth in which the host cell is cultured (by volume) over time (per hour).

As used herein, the term "promoter" refers to a synthetic or naturally-derived nucleic acid that is capable of conferring, activating or enhancing expression of a DNA coding sequence. A promoter may comprise one or more specific transcriptional regulatory sequences to further enhance expression and/or to alter the spatial expression and/or temporal expression of the coding sequence. A promoter may be positioned 5' (upstream) of the coding sequence under its control. The distance between the promoter and a coding sequence to be expressed may be approximately the same as the distance between that promoter and the native nucleic acid sequence it controls. As is known in the art, variation in this distance may be accommodated without loss of promoter function. The regulated promoter used herein generally allows transcription of the nucleic acid sequence encoding a transcriptional regulator (e.g., an activator such as pGal4, or a repressor such as pGal80) while in a permissive environment (e.g., microaerobic fermentation conditions, or the presence of maltose), but ceases transcription of the nucleic acid sequence encoding a transcriptional regulator while in a non-permissive environment (e.g., aerobic fermentation conditions, or in the absence of maltose).

The phrase "strain stability" generally refers to the stability of heterologous compound production over extended periods of fermentation by a genetically modified host cell described herein. In particular, stability refers the ability of a microbe to maintain favorable production characteristics (i.e., high yield (grams of compound per gram of substrate) and/or productivity (grams per liter of fermentation broth per hour)) of a non-catabolic fermentation product over extended cultivation times, e.g., 3 to 20 days. Genetic stability, which is the propensity of the producing microbial population to have little to no alteration of the intended allelic frequency of genes relevant to the production of product over time, plays a major role in the sustained output of product.

The term "yield" refers to production of a non-catabolic compound by a host cell, expressed as the amount of non-catabolic compound produced per amount of carbon source consumed by the host cell, by weight.

5.2 Use of an Oxygen-Sensitive Promoter in Combination with Microaerobic

Fermentation as a Switch for Production of Heterologous Compounds In some embodiments, the methods and compositions provided herein utilize oxygen-sensitive promoters to drive the expression of heterologous enzymes capable of effecting non-catabolic compound production in a genetically modified host cell under microaerobic fermentation conditions. When fermentation of the host cell is carried out under aerobic fermentation conditions, non-catabolic compound production is substantially reduced or turned off; when the fermentation conditions are microaerobic, non-catabolic compound production is turned on or increased. Thus, the genetically modified cells described herein enable the use of low oxygen conditions as a switch for the production of non-catabolic compounds. In particular, controlling the timing of non-catabolic compound production to occur only when production is desired redirects the carbon flux during the non-production phase into cell maintenance and biomass. This more efficient use of carbon greatly reduces the metabolic burden on the host cells, increases the stability of the heterologous genes, reduces strain degeneration, and contributes to better overall health and viability of the cells. Accordingly, the methods and genetically modified host cells provided herein utilize low oxygen fermentation conditions as a switch to effect the "off" and "on" stages of an improved fermentation process for production of heterologous non-catabolic compounds.

In the first step (i.e., the "build" stage, step (a)), the genetically modified host cells are grown in a growth or "build" medium under aerobic conditions, i.e., wherein oxygen is provided in non-limiting amounts. In the second step (i.e., the "production" stage, step (b)), the fermentation is carried out under microaerobic conditions, which serves as a non-genetic switch to substantially boost the production of the non-catabolic compound. The initial growth under fully aerobic conditions ensures that the energy requirements of the cells are met while the biomass of the cells quickly increases. Thereafter, switching to microaerobic conditions enables the synthesis of the non-catabolic product.

5.2.1 Oxygen Sensitive DAN1 Promoters

In some embodiments, an oxygen-sensitive promoter useful for regulating the expression of enzymes capable of effecting non-catabolic compounds in the methods provided herein is the DAN1 promoter, and homologues and variants thereof (SEQ ID NOS: 1-11). In some embodiments, the DAN1 promoter is from *S. cerevisiae*. The wild-type DAN1 promoter (SEQ ID NO: 1) is inactive under aerobic conditions but highly active under anaerobic ones. See, e.g., Kwast et al., *J Bacteriol.* 184(1):250-265 (2002); Piper et al., *J Biol Chem* 277(40):37001-37008 (2002); and ter Linde et al., *J Bacteriol.* 181(24):7409-7413 (1999).

The *Saccharomyces cerevisiae* DAN/TIR genes are among a large group of genes that are upregulated during adaptation to anaerobic growth (see, Lai et al., *Mol Cell Biol.* 25(10):4075-4091 (2005); Sertil et al., *Gene* 192(2):199-205 (1997); and Tai et al., *J Biol Chem.* 280(1):437-447 (2005). These genes code for cell wall mannoproteins, which play a significant role in cell wall permeability. The kinetics of expression of these genes ranges from 30 minutes to 3 hours following the onset of anaerobiosis (see Abramova et al., *J Bacteriol.* 183(9):2881-2887 (2001)).

It appears that a complex programmed cell wall remodeling occurs during adaptation to anaerobiosis, as shown by the fact that the major aerobic cell wall mannoproteins encoded by CWP1 and CWP2 are replaced by their anaerobic counterparts, encoded by the DAN/TIR genes, under those conditions.

Fastidious anaerobiosis, which is required for efficient induction of the wild-type DAN1 promoter has been achieved by bubbling cultures with nitrogen to deplete oxygen (see Cohen et al., *Nucleic Acids Res* 29(3):799-808 (2001)). However, Nevoigt et al. have developed a series of DAN1 promoter mutants (SEQ ID NOS: 1-10) which are inducible under conditions that involve simple elimination or reduction of aeration. See Nevoigt et al., *Biotechnology and Bioengineering* 96(3):550-558 (2007); and United States Patent Application No. 2007/0178505, the contents of which are incorporated by reference in their entirety.

Thus, in some embodiments, the DAN1 promoters useful in the methods provided herein are those described in United States Patent Application No. 2007/0178505, and include promoters comprising SEQ ID No: 1, 2, 3, 4, 5, 6, 7, 8, 9, or 10. In some embodiments, the DAN1 promoters useful in the methods provided herein comprise SEQ ID No: 1, 2, 3, 4, 5, or 6. In some embodiments, the DAN1 promoters useful in the methods provided herein comprise SEQ ID No: 1 or 2. In some embodiments, the DAN1 promoters useful in the methods provided herein comprise SEQ ID No: 1. In some embodiments, the DAN1 promoters useful in the methods provided herein comprise SEQ ID No: 2.

In another embodiment, the DAN1 promoter useful in the methods provided herein comprises a mutation in one or more of the following positions of SEQ ID No: 11: 1-56; 66-139; 148-232; 245-283; 290-293; 301-302; 310; 322-326; 334-347; 357-371; 380-450; or 458-551. According to this aspect and in one embodiment, the mutation is at position: 4, 7, 15, 18, 19, 21, 22, 26, 28, 36, 40, 53, 56, 60, 63, 66, 74, 75, 78, 86, 99, 122, 132, 135, 136, 149, 153, 162, 164, 165, 171, 172, 176, 187, 196, 198, 201, 205, 207, 211, 216, 226, 228, 233, 234, 237, 241, 260, 269, 274, 277, 280, 281, 285, 296, 299, 303, 307, 308, 310, 313, 322, 327, 331, 332, 337, 338, 343, 344, 346, 366, 368, 373, 375, 376, 381, 384, 386, 390, 391, 392, 396, 397, 402, 404, 422, 427, 428, 429, 432, 434, 439, 445, 467, 469, 470, 477, 480, 490, 492, 508, 511, 514, 518, 528, or a combination thereof. In one embodiment, mutations at these positions may be to any nucleotide other than the wild-type nucleotide, while in another embodiment, mutations at each position is to a specific nucleotide as described hereinbelow.

In another embodiment, the DAN1 promoter useful in the methods provided herein comprises a sequence comprising a replacement of: (a) a T with a C at nucleotide position 4, 15, 19, 36, 53, 56, 60, 66, 74, 75, 78, 86, 99, 132, 136, 176, 201, 205, 207, 216, 226, 228, 269, 277, 281, 285, 299, 303, 310, 327, 331, 332, 375, 376, 390, 428, 434, 467, 477, 480, 508, 511, or a combination thereof; (b) an A with a G at at nucleotide position 7, 18, 26, 40, 122, 135, 149, 153, 162, 164, 165, 171, 172, 187, 196, 211, 233, 234, 237, 241, 260, 274, 280, 308, 313, 322, 337, 343, 344, 346, 366, 368, 381, 384, 386, 396, 397, 402, 404, 422, 427, 429, 432, 445, 470, 490, 492, or a combination thereof; (c) a C with an A at nucleotide position 21; (d) an A with a C at nucleotide position 237, 338, 469, 514, 518; (e) a C with a T at nucleotide position 28, 296, 307, 373, 392, 528, or a combination thereof; (f) a G with an A at nucleotide position 22, 63, 391, 439 or a combination thereof; (g) a T with a G at nucleotide 198; or any combination thereof, of the sequence as set forth in SEQ ID NO: 11.

In another embodiment, the DAN1 promoter useful in the methods provided herein comprises mutations in a portion of a promoter that is structurally or functionally homologous to the portion of the DAN1 promoter mutated as described herein. In another embodiment, the promoter useful in the methods provided herein comprises mutations in a promoter that is homologous to the DAN1 promoter. In one embodiment, homologous promoters or portions thereof are derived from *S. cerevisiae* sequences, while in another embodiment, they are derived from other *Saccharomyces* species, while in another embodiment, they are derived from *Saccharomycetaceae*, while in another embodiment, they are derived from *Saccharomycetales*, while in another embodiment, they are derived from *Saccharomycetes*, while in another embodiment, they are derived from *Saccharomycotina*, while in another embodiment, they are derived from *Ascomycota*, while in another embodiment, they are derived from fungal species. In another embodiment, promoters homologous to the DAN1 promoter show similar oxygen dependency as the DAN1 promoter. One of skill in the art would be able to determine the oxygen dependency of a promoter using methods that are routine in the art. Determinations of homologous promoters or promoter regions are made routinely by those of skill in the art using tools known in the art such as sequence alignments.

In one embodiment, a homologous promoter to DAN1 is DAN2, DAN3, DAN4, TIR1, TIR2, TIR3, or TIR4. In another embodiment, a homologous promoter to DAN1 is CYC1, CYC7, ANB1, COX5b, ERG11, MOX1, MOX2, MOX4/UPC2, ROX7/MOT3, or ROX1 promoters.

In one embodiment, mutations may be in a portion of a promoter corresponding to anaerobic response elements binding sites, which in one embodiment is AR1 or AR2, while in another embodiment, mutations may be in Mot3 or Rox1 binding sites.

5.2.1.1 Targets of DAN1 Promoter Regulation

In some embodiments, the methods provided herein utilize genetically modified host cells that comprise a heterologous nucleic acid encoding one or more enzymes of an enzymatic pathway for making the heterologous non-catabolic compound. In some embodiments, expression of the one or more enzymes is under direct control of a mutated DAN1 promoter. That is, the one or more heterologous nucleic acid sequences encoding the one or more enzymes of the enzymatic pathway are each operably linked to (i.e., is positioned 3' of) a mutated DAN1 promoter, and the mutant DAN1 promoter drives expression of each of said one or more heterologous nucleic acids under microaerobic conditions.

In other embodiments, expression of the one or more enzymes of an enzymatic pathway is indirectly regulated by the mutated DAN1 promoter. For example, indirect regulation of the one or more enzymes of the pathway can be achieved by operably linking a mutated DAN1 promoter to a single heterologous transcriptional regulator, the expression of which, in turn, directly regulates expression of the one or more enzymes (e.g., all the members) of the pathway. The GAL regulon in yeast provides an exemplary regulatory network of activators, repressors and promoters that can be utilized in combination with a mutated DAN1 promoter described herein. Yeast can utilize galactose as a carbon source via expression of the GAL genes to import galactose and metabolize it inside the cell. The GAL genes include structural genes GAL1, GAL2, GAL7, and GAL10 genes, which respectively encode galactokinase, galactose permease, α-D-galactose-1-phosphate uridyltransferase, and uridine diphosphogalactose-4-epimerase, and regulator genes GAL4, GAL80, and GAL3. The GAL4 gene product is a positive regulator (i.e., activator) and the GAL80 gene product is a negative regulator (i.e., repressor) of the expression of the GAL1, GAL2, GAL7, and GAL10 genes. Gal4p activates transcription by binding upstream activating sequences (UAS), such as those of the GAL structural genes, i.e., within the pGAL1, pGAL7 and pGAL10 promoters. In the absence of galactose, very little expression of the structural proteins (Gal1p, Gal2p, Gal7p, and Gal10p) is typically detected, due to Gal80p interacting with Gal4p and preventing Gal4p transcriptional activity. In the presence of galactose, however, Gal3p interacts with Gal80p, relieving Gal4p repression by Gal80p. This allows expression of genes downstream of Gal4p binding sequences, such as the GAL1, GAL2, GAL7, and GAL10 gene products.

Thus, in some embodiments, one or more GAL4-activated promoters, e.g., pGAL1, pGAL7, and/or pGAL10, are operably linked to, and are used to drive expression of, the one or more enzymes of an enzymatic pathway for making the heterologous non-catabolic compound, and expression of the GAL4 gene product is driven by a mutated DAN1 promoter described herein. Accordingly, expression of the one or more enzymes of the pathway is induced by Gal4p under microaerobic conditions. In some such embodiments, expression of the GAL80 gene is reduced or abolished, using known techniques for gene disruption, such that Gal80p is no longer present to negatively regulate Gal4p activity, independent of the oxygen conditions of the fermentation. In some embodiments, the native pGAL4 promoter is replaced by a heterologous nucleic acid comprising a mutated DAN1 promoter. In some embodiments, the host cell comprises a heterologous nucleic acid comprising a nucleic acid that encodes Gal4p, operably linked to a heterologous nucleic acid comprising a mutated pDAN1 promoter. In one embodiment, a mutated DAN1 promoter is operably linked to a coding sequence for Gal4p, and the coding sequences of the one or more enzymes (e.g., all the members) of the enzymatic pathway for making the heterologous non-catabolic compound are operably linked to GAL4-responsive promoters. In some embodiments, the GAL4-responsive promoter is pGAL1. In some embodiments, the GAL4-responsive promoter is pGAL7. In some embodiments, the GAL4-responsive promoter is pGAL10.

5.2.2 Aerobic and Microaerobic Amounts of Oxygen

In certain embodiments of the methods provided herein, the cells are cultured or maintained during the build stage under conditions that are not limited by oxygen, i.e., aerobic conditions, followed by culturing or maintenance of the cells under conditions that are oxygen limiting, i.e., microaerobic or anaerobic conditions.

Maintaining fully aerobic conditions can be challenging particularly in large scale processes due to limitations of mass transfer and the relatively low solubility of oxygen in aqueous solutions. For example, if air is used to sparge into tanks, the solubility of oxygen in water is 9 milligrams per liter at 20° C. If pure oxygen is used instead of air, then the solubility increases to 43 milligrams per liter. In either case (sparging air or pure oxygen), this amount of oxygen is depleted in seconds by an active and concentrated microbial population unless oxygen is continuously supplied. In comparison, the amounts of other nutrients that are used by the cells during the same period (seconds, e.g., less than a minute) are negligible compared to the bulk concentrations. We have found that the host cells producing heterologous non-catabolic compounds are able to tolerate some period of oxygen limitation is and still make high levels of isoprenoid compounds. This flexibility allows for a more economical process by providing savings in terms of tank design, decreased demand for oxygen gas, lower energy costs for aeration and the like.

Oxygen limitation occurs when the specific growth rate of the host cells is less than the maximum specific growth rate where oxygen is not limiting (e.g., provided in excess). Specific growth rate is the rate of growth of cells per unit of biomass per unit time and has the units of reciprocal time (1/t). The maximum specific growth rate for cells in a culture medium relates to the effect of a substrate concentration on growth rate which in this case is oxygen. Generally, cells will grow slowly at a low level of the substrate, and as the level of the substrate in the medium increases, so does the rate of cell growth. However, the rate of cell growth does not continue to rise indefinitely, and at high levels of substrate, a given increase in the amount of substrate will produce a smaller and smaller increase in the rate of cell growth. Therefore, the growth rate ultimately reaches a limit, which is often referred to as the maximum specific growth rate.

A theoretical treatment of the relationship between growth rates in culture is well known to those skilled in the art, and is referred to as the Monod equation. See, for example, Pirt, Principles of Microbe and Cell Cultivation, Wiley, N Y, 1975, pages 4-10. In this theoretical treatment, the maximum specific rate is an asymptotic limit that is never reached until an infinite level of substrate is reached. In practice, however, the maximum specific growth rate can be considered as being obtained when the conditions under investigation (e.g., a substrate level such as oxygen) support the fastest initial growth rate. For instance, in a fed-batch reactor, the initial condition where all substrates required for growth (e.g. nutrients and oxygen) are supplied in excess and fermentation occurs at the optimal temperature for the host cell is treated as the conditions for the maximum growth rate. See, for example, Lee et al. (1996) Trends Biotechnol. 14: 98-105 and Korz et al. (1995) J Biotechnology 39:59-65. Maximum specific growth rate is also sometimes referred to as unlimited growth.

In one method, oxygen limitation is quantified by oxygen concentration in the medium and is expressed in terms of dissolved oxygen concentration (DOC). The DOC in the culture medium can be less than about 20%, less than about 15%, less than about 10%, and less than about 5%. In other embodiments the DOC is about 0% or below the level of detection. However, because oxygen is consumed by the cells relatively rapidly, a DOC of zero can mean that the cells are being cultured under anaerobic conditions (no oxygen) or that the cells are consuming oxygen as fast as it is being supplied. In another method, the cells' use of oxygen is expressed in terms of oxygen uptake rate (OUR; the cells' rate of oxygen consumption per liter of medium) to differentiate between these two possibilities. Suitable oxygen uptake rates include less than about 50 mmoles, less than about 40 mmoles, less than about 30 mmoles, less than about 20 mmoles per liter of medium, or less than about 10 mmoles per liter of medium. Alternatively, specific oxygen uptake rate (SOUR which is OUR divided by cell density) can be used when normalized values with respect to cell densities is preferred. The amount of microorganism per liter of fermentation, or the density of microorganism, can be measured by measuring the weight of microorganism isolated from a given volume of the fermentation medium. A common measure is the dry weight of cells per liter of fermentation medium. Another method which can be used to monitor the fermentation while it is progressing is by a measurement of the optical density of the medium. A common method is to measure the optical density at a wavelength of 600 nm, referred to the $OD_{600}$, or the OD. The OD can be correlated to a the density of a specific type of organism within a specific medium, but the specific relationship between OD and amount of microorganism per volume will not generally be applicable across all types of organisms in all types of media. A calibration curve can be created by measuring the OD and the dry cell weight over a range of cell densities. In some cases, these correlations can be used in different fermentation of the same or similar microorganisms in the same or similar media. Suitable specific oxygen uptake rates include less than about 30 mmoles, less than about 25 mmoles, less than about 20 mmoles, less than about 15 mmoles, less than about 10 mmoles, or less than about 5 mmoles per gram of dry cell weight per hour.

The culture medium can be maintained to have a dissolved oxygen content during the course of culture to maintain cell growth and to maintain cell metabolism for production of non-catabolic compounds as needed, in accordance with the build stage or production stage. The oxygen concentration of the culture medium can be monitored using known methods, such as through the use of an oxygen electrode. Oxygen can be added to the culture medium using methods known in the art, through agitation and aeration of the medium by stirring, shaking or sparging. Although aeration of the medium has been described herein in relation to the use of air, other sources of oxygen can be used. Particularly useful is the use of an aerating gas that contains a volume fraction of oxygen greater than the volume fraction of oxygen in ambient air. In addition, such aerating gases can include other gases, which do not negatively affect the culture.

In some embodiments, microaerobic conditions are achieved by bubbling the culture with nitrogen, e.g., high purity nitrogen (99.8%). In some embodiments, microaerobic conditions are achieved by culturing the cells in air-tight vessels, for example, screw-capped vials and flasks, and the like. Because residual dissolved oxygen is consumed during cell growth, these conditions sharply lower, but do not completely deplete, oxygen availability during the course of the cell growth. In some embodiments, microaerobic conditions can be achieved by means of mixing air in an appropriate amount with a carrier gas. Alternatively, an appropriately low flow rate of air can be sparged. The oxygen level in the fermentation medium can be monitored using an oxygen electrode or any other suitable device, and the flow rate of the gas mix is adjusted to assure that the level of oxygen in the fermentation fluid is maintained at a constant level. In addition to variations in the inlet gas flow rate or the composition of the inlet gas, microaerobic conditions can also be produced by decreasing the stir rate (thus decreasing the oxygenation of a large culture), or by adding more feedstock to increase the cell density (and hence higher oxygen demand), or combinations thereof.

In some embodiments, dissolved oxygen ($dO_2$) can be controlled by feeding sugar to the host cells to keep the $dO_2$ concentration at undetectable levels through most of the fermentation. In some embodiments, oxygen can be supplied via compressed gas sparging and mechanical agitation of the fermentation broth. In some embodiments, the oxygen is supplied at a rate ranging from approximately 50 to 200 mmol $O_2$/L/h, for example, approximately 50, 60, 70, 80, 90, 100, 110, 120, 130, 140, 150, 160, 170, 180, 190 or 200 mmol $O_2$/L/h. In a particular embodiment, oxygen is supplied at a rate of approximately 110 mmol $O_2$/L/h. In order to utilize all of this available oxygen, sugar is fed fast enough to ensure that enough NADH is produced via its catabolism to convert all of the available $dO_2$ in the media into H2O. To ensure this, sugar can be fed at a slightly faster rate than the stoichiometric demand for $O_2$, such that some ethanol is produced. Periodically, no sugar is fed to induce the culture to reconsume the ethanol that was produced, a process which also requires $O_2$ consumption by the culture. Once the ethanol is exhausted, the $dO_2$ concentration rises rapidly, signaling the culture is depleted of oxidizable carbon. This $dO_2$ spike is measured by a probe and the process resumes feeding sugar, returning the $dO_2$ to undetectable levels.

Assuming a well-mixed environment with no spatial gradients and neglecting the negligible dilution term (since the $O_2$ entering the tank is negligible compared to the $O_2$ entering in the gas phase), the $1^{st}$ order differential equation describing the change in dissolved oxygen in the fermentor is given by:

$$\frac{d(dO_2)}{dt} = k_l a(dO_{2sat} - dO_2) - q_{O2}[X]$$

Where:
$dO_2$ is the dissolved oxygen concentration in the reactor at time t
$k_l$ is the vapor-liquid mass transfer coefficient for $O_2$
a is the ratio of bubble surface area to liquid volume
$dO_2$sat is the equilibrium concentration of $O_2$ in the liquid phase corresponding to the temperature, pressure, and gas phase $O_2$ concentration of the process
$q_{O2}$ is the specific oxygen consumption rate by a gram of biomass (mmol/g dw/h)
[X] is the biomass concentration in the reactor at time t
This equation can be simplified to highlight that there are two components affecting the dissolved oxygen concentration: the oxygen transfer rate (OTR) which is a function of the mass transfer characteristics of the broth (kl), the surface area for transport of gas (a) and the driving force for mass transfer ($dO_2$sat-$dO_2$); and the oxygen uptake rate (OUR) which is a function of the concentration of biomass ([X]) and how fast the biomass is consuming $O_2$ ($q_{O2}$). So now simply:

$$\frac{d(dO_2)}{dt} = OTR - OUR$$

These equations can be used to help understand the profile of $dO_2$ in time.

5.3 Use of an Maltose-Responsive Promoter in Combination with Maltose Manipulation as a Switch Production of Heterologous Compounds In some embodiments, the methods and compositions provided herein utilize maltose-responsive promoters in combination with manipulation of maltose content in the fermentation medium to regulate, either directly or indirectly, the expression of heterologous enzymes capable of effecting non-catabolic compound production in a genetically modified host cell.

In one embodiment, when fermentation of the host cell is carried out in the presence of maltose, e.g., at least 0.1% maltose, non-catabolic compound production is substantially reduced or turned off, and when the amount of maltose in the fermentation culture medium is reduced or eliminated, non-catabolic compound production is turned on or increased. Thus, in some embodiments, the genetically modified cells described herein comprise heterologous biosynthetic pathway genes that are regulated by a maltose-responsive promoter that enables the use of maltose in the fermentation medium as a switch for the production of non-catabolic compounds. Controlling the timing of non-catabolic compound production to occur only when production is desired redirects the carbon flux during the non-production phase into cell maintenance and biomass. This more efficient use of carbon greatly reduces the metabolic burden on the host cells, improves cell growth, increases the stability of the heterologous genes, reduces strain degeneration, and contributes to better overall health and viability of the cells.

In some embodiments, the fermentation method comprises a two-step process that utilizes maltose as a switch to effect the "off" and "on" stages. In the first step (i.e., the "build" stage, step (a)) wherein production of the compound is not desired, the genetically modified host cells are grown in a growth or "build" medium comprising maltose in an amount sufficient to induce the expression of genes under the control of a maltose-responsive promoter, and the induced gene products act to negatively regulate production of the non-catabolic compound. In the second step (i.e., the "production" stage, step (b)), the fermentation is carried out in a culture medium comprising a carbon source wherein maltose is absent or in sufficiently low amounts such that the maltose-responsive promoter is no longer active, and production of the heterologous non-catabolic compound by the host cells is turned on or increased.

In other embodiments, the maltose-responsive promoter can be operably linked to the one or more heterologous nucleic acids encoding the one or more enzymes of the enzymatic pathway, and the presence of an activating amount of maltose in the culture medium increase the expression of the one or more enzymes of the enzymatic pathway. In this fashion, the maltose-responsive promoter can be wired to act as a positive regulator of non-catabolic compound production.

5.3.1 Maltose-Responsive Promoters

In preferred embodiments, useful maltose-responsive promoters useful in the methods and compositions provided herein promote transcription of an operably linked DNA coding sequence in the presence of maltose. In some embodiments, a maltose-responsive promoter useful for regulating the expression of enzymes capable of effecting non-catabolic compounds in the methods and compositions provided herein is any maltose-responsive promoter known in the art. In some embodiments, the maltose-responsive promoter is selected from the group consisting of pMAL1 (SEQ ID NO:12), pMAL2 (SEQ ID NO:13), pMAL11 (SEQ ID NO:14), pMAL12 (SEQ ID NO:15), pMAL31 (SEQ ID NO:16) and pMAL32 (SEQ ID NO:17). In particular embodiments, the maltose-sensitive promoter is pMAL32 (SEQ ID NO:17).

Other useful maltose-responsive promoters useful in the methods and compositions provided herein can be derived from the regulatory network for the maltose fermentation system of *S. cerevisiae*. Maltose fermentation in *Saccharomyces* species requires the presence of at least one of five unlinked MAL loci: MAL1, MAL2, MAL3, MAL4, and MAL6. Each of these loci consists of a complex of genes involved in maltose metabolism; the complex includes maltase, a maltose permease, and an activator of these genes. At the MAL6 locus, the activator is encoded by the MAL63 gene. Mal63p is a DNA-binding transcription activator required for the maltose-dependent induction of the MAL structural genes encoding maltose permease and maltase. A MAL activator intermediate complex is stable in the absence of inducer maltose, but addition of maltose causes the release of inducible MAL activator from the complex in an active form capable of DNA binding and transcription activation. See, e.g., Ran, F. and Michels., C. A., *J. Biol. Chem.* 285(18):13850-13862 (2010). Binding sites of the MAL63 protein in the divergently transcribed MAL61-62 promoter have been characterized as an upstream activating sequence for the MAL genes. See, e.g., Ni, B. and Needleman, R., "Identification of the Upstream Activating Sequence of MAL and the Binding Sites for the MAL63 Activator of *Saccharomyces cerevisiae*," *Molecular and Cellular Biology* 10(7):3797-3800 (1990), the contents of which are incorporated by reference in their entirety.

Other useful maltose-responsive promoters useful in the methods and compositions provided herein can be derived from the regulatory network for the maltose/maltodextrin metabolism system of *E. coli*. The malT nucleic acid encodes MalT, a positive regulator of four maltose-responsive promoters ($P_{PQ}$, $P_{EFG}$, $P_{KBM}$, and $P_S$). The combination of malT and a mal promoter creates a tightly regulated expression system that has been shown to work as a strong promoter induced by the addition of maltose. See, e.g., Schleif, "Two Positively Regulated Systems, ara and mal," pp. 1300-1309 in *Escherichia coli and Salmonella Cellular and Molecular Biology*, Second Edition, Neidhardt et al., eds., ASM Press, Washington, D.C., 1996; and Boos, W. and Shuman, H., "Maltose/Maltodextrin System of *Escherichia coli*: Transport, Metabolism and Regulation," *Microbiology and Molecular Biology Reviews*, 62(1):204-229 (1998)), the contents of which are hereby incorporated by reference in their entireties.

Other useful maltose-responsive promoters useful in the methods and compositions provided herein include those in Berkner et al., "Inducible and constitutive promoters for genetic systems in *Sulfolobus acidocaldarious*, "*Extremophiles* 14:249-259 (2010); and U.S. Pat. No. 5,824,545.

5.3.1.1 Targets of Maltose-Responsive Promoter Regulation

In some embodiments, the methods provided herein utilize genetically modified host cells that comprise a heterologous nucleic acid encoding one or more enzymes of an enzymatic pathway for making the heterologous non-catabolic compound. In some embodiments, expression of the one or more enzymes is under direct control of a maltose-responsive promoter described herein. That is, the one or more heterologous nucleic acid sequences encoding the one or more enzymes of the enzymatic pathway are each operably linked to (i.e., is positioned 3' of) a maltose-responsive, and the maltose-responsive promoter drives expression of each of said one or more heterologous nucleic acids in the presence of maltose.

In other embodiments, expression of the one or more enzymes of an enzymatic pathway is indirectly regulated by the maltose-responsive promoter. For example, indirect regulation of the one or more enzymes of the pathway can be achieved by operably linking a maltose-responsive promoter to a single heterologous transcriptional regulator, the expression of which, in turn, directly regulates expression of the one or more enzymes (e.g., all the members) of the pathway. The GAL regulon in yeast, described in detail above, provides an exemplary regulatory network of activators, repressors and promoters that can be utilized in combination with a maltose-responsive promoter described herein.

In some embodiments, one or more GAL4-activated promoters, e.g., pGAL1, pGAL7, and/or pGAL10, are operably linked to, and are used to drive expression of, the one or more enzymes of an enzymatic pathway for making the heterologous non-catabolic compound. In some embodiments, the host cell further comprises a nucleic acid encoding GAL4. In some embodiments, the GAL4 gene product is constitutively expressed, i.e. is under the control of a constitutive promoter. In some embodiments, the host cell further comprises a nucleic acid encoding GAL80 under the control of a maltose-responsive promoter described herein, and expression of the GAL80 gene product is induced in the presence of maltose. Gal80p, in turn, interacts with Gal4p and prevents Gal4p transcriptional activity. When maltose is removed or sufficiently depleted so that GAL80 expression is no longer induced, Gal4p is relieved of repression by Gal80p, and is free to activate expression of the one or more enzymes of an enzymatic pathway for making the heterologous non-catabolic compound.

In other embodiments, the native pGAL4 promoter is replaced by a heterologous nucleic acid comprising a maltose-responsive promoter. In some embodiments, the host cell comprises a heterologous nucleic acid comprising a nucleic acid that encodes Gal4p, operably linked to a heterologous nucleic acid comprising maltose-responsive promoter. In one embodiment, a maltose-responsive promoter is operably linked to a coding sequence for Gal4p, and the coding sequences of the one or more enzymes (e.g., all the members) of the enzymatic pathway for making the heterologous non-catabolic compound are operably linked to GAL4-responsive promoters, such that expression of the one or more enzymes are induced in the presence of maltose. In some embodiments, the GAL4-responsive promoter is pGAL1. In some embodiments, the GAL4-responsive promoter is pGAL7. In some embodiments, the GAL4-responsive promoter is pGAL10.

5.3.2 Repressing and Non-Repressing Amounts of Maltose

Maltose is a disaccharide sugar formed from 2 glucose molecules, as shown below. It has the chemical formula, $C_{12}H_{22}O_{11}$, and a molecular weight of 343 g/mol.

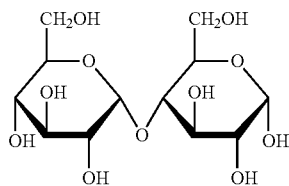

In some embodiments of the methods provided herein, an "inducing" amount of maltose, that is, an amount of maltose sufficient to induce expression of a coding sequence operably linked to a maltose-responsive promoter, and a "non-inducing" amount of maltose, that is, an amount of maltose below which expression of a coding sequence operably linked to a maltose-responsive promoter is not induced, for use in the methods provided herein can be determined for any genetically modified host cell capable of producing a heterologous non-catabolic compound. In some embodiments, a non-inducing amount of maltose is determined by performing a gene expression curve in the presence of increasing amounts of maltose in the culture medium to be used in the fermentation process, i.e., a maltose titration. For example, a population of genetically modified host cells may be divided into a plurality of subpopulations and cultured in parallel, wherein each subpopulation is grown in culture media comprising a different, e.g., increasing amount of maltose (including no maltose), and reporter gene expression or non-catabolic compound production is assayed after a defined period of time.

In some embodiments, where the maltose-responsive promoter is wired to effect an "off" state of non-catabolic compound production in the presence of maltose, the maltose titration comprises at least two concentrations of maltose whereby non-catabolic compound production of the host cells is plateaued at a minimum, that is, where no further decrease in production of the compound is observed with an increase in maltose concentration. In some embodiments, the "repressing" amount of maltose is at least the minimum amount of maltose at which non-catabolic compound production of the host cells is plateaued at its minimum (e.g., at zero). This amount can also be referred to as a "saturating" or "optimal" amount of maltose for repression of non-catabolic compound production for the particular host cell. In some such embodiments, the "repressing" amount of maltose can include any concentration of maltose at which non-catabolic compound production has been decreased relative to an "on" state, even where there is a low level of compound production. In some embodiments, the non-repressing amount of maltose, in this configuration of the switch, is any amount of maltose below the "repressing" amount of maltose. In some embodiments, the non-repressing amount of maltose is at least 2, 3, 4, 5, 6, 7, 8, 9, 10, 20, 30, 40, 50, 60, 70, 80, 90, 100 or greater than 100 times less than the repressing amount of maltose. In a particular embodiment, the non-repressing amount of maltose is less than 0.8% (w/v) of the culture medium. In another particular embodiment, the non-repressing amount of maltose is less than 0% (w/v) of the culture medium.

In a specific embodiment, the repressing amount of maltose is the optimal or saturating amount for a given host cell, as described above, and the non-repressing amount is no maltose. In another specific embodiment, the repressing amount of maltose is at least 0.25%, and the non-repressing amount is no maltose. In another specific embodiment, the repressing amount of maltose is an amount of maltose from 0.25% to 3%, and the non-repressing amount is no maltose. In another specific embodiment, the repressing amount of maltose is at least 3%, and the limiting amount is no maltose.

In some embodiments where the maltose-responsive promoter is wired to effect an "off" state of non-catabolic compound production in the presence of maltose, the repressing amount of maltose in the culture medium is at least 0.1% (weight maltose per volume of culture medium). In some embodiments, the repressing amount of maltose in the culture medium is at least 0.25%. In some embodiments, the repressing amount of maltose in the culture medium is at least 0.5%. In some embodiments, the repressing amount of maltose in the culture medium is at least 0.75%. In some embodiments, the repressing amount of maltose in the culture medium is at least 1.0%. In some embodiments, the repressing amount of maltose in the culture medium is at least 1.25%. In some embodiments, the repressing amount of maltose in the culture medium is at least 1.5%. In some embodiments, the repressing amount of maltose in the culture medium is at least 1.75%. In some embodiments, the repressing amount of maltose in the culture medium is at least 2.0%. In some embodiments, the repressing amount of maltose in the culture medium is at least 2.25%. In some embodiments, the repressing amount of maltose in the culture medium is at least 2.5%. In some embodiments, the repressing amount of maltose in the culture medium is at least 2.75%. In some embodiments, the repressing amount of maltose in the culture medium is at least 3.0%. In some embodiments, the repressing amount of maltose in the culture medium is at least 3.25%. In some embodiments, the repressing amount of maltose in the culture medium is at least 3.5%. In some embodiments, the repressing amount of maltose in the culture medium is at least 3.75%. In some embodiments, the repressing amount of maltose in the culture medium is at least 4.0%. In some embodiments, the repressing amount of maltose in the culture medium is at least 4.25%. In some embodiments, the repressing amount of maltose in the culture medium is at least 4.5%. In some embodiments, the repressing amount of maltose in the culture medium is at least 4.75%. In some embodiments, the repressing amount of maltose in the culture medium is at least 5.0%. In some embodiments, the repressing amount of maltose in the culture medium is between 5% and 50%. In some embodiments, the repressing amount of maltose in the culture medium is about 5%, 10%, 15%, 20%, 25%, 30%, 35%, 40% 45% or about 50%.

In some embodiments, the non-repressing amount of maltose is an amount that is at least 2-fold, 10-fold, 100-fold, 1000-fold, 10,000-fold or 100,000-fold less than a repressing amount of maltose as determined according to the methods described above. In some embodiments, the non-repressing amount of maltose is an amount that is at least 2-fold, 10-fold, 100-fold, 1000-fold, 10,000-fold or 100,000-fold less than the saturating amount of maltose as determined according to the methods described above. In some embodiments, the non-repressing amount of maltose is an amount that is less than 50%, less than 20%, less than 10%, less than 1%, less than 0.5%, less than 0.2%, less than 0.1%, less than 0.01%, or less than 0.001% of a repressing amount of maltose as determined according to the methods described above. In some embodiments, the non-repressing amount of maltose is an amount that is less than 50%, less than 20%, less than 10%, less than 1%, less than 0.1%, less than 0.01%, or less than 0.001% of the saturating amount of maltose as determined according to the methods described above. In a specific embodiment, the non-repressing amount of maltose is 0 mg/L (0%), i.e., no maltose. Thus, in this specific embodiment, the host cells are grown during the production stage in a cell culture medium that comprises no external source of maltose.

In some embodiments, where the maltose-responsive promoter is wired to effect an "on" state of non-catabolic compound production in the presence of maltose, the maltose titration comprises at least two concentrations of maltose whereby non-catabolic compound production of the host cells is plateaued at a maximum, that is, where no further increase in production of the compound is observed with an increase in maltose concentration. In some embodiments, the "non-repressing" amount of maltose is at least the minimum amount of maltose at which non-catabolic compound production of the host cells is plateaued at its maximum. This amount can also be referred to as a "saturating" or "optimal" amount of maltose for induction of non-catabolic compound production for the particular host cell, in this configuration of the switch. In some such embodiments, the "inducing" amount of maltose can include any concentration of maltose at which non-catabolic compound production has been increased relative to an "off" state, even where compound production is suboptimal. In some embodiments, the non-inducing amount of maltose, in this configuration of the switch, is any amount of maltose below the "inducing" amount of maltose. In some embodiments, the non-inducing amount of maltose is at least 2, 3, 4, 5, 6, 7, 8, 9, 10, 20, 30, 40, 50, 60, 70, 80, 90, 100 or greater than 100 times less than the inducing amount of maltose. In a particular embodiment, the non-inducing amount of maltose is less than 0.8% (w/v) of the culture medium. In another particular embodiment, the non-inducing amount of maltose is less than 0% (w/v) of the culture medium.

In a specific embodiment, the inducing amount of maltose is the optimal or saturating amount for a given host cell, as described above, and the non-inducing amount is no maltose. In another specific embodiment, the inducing amount of maltose is at least 0.25%, and the non-inducing amount is no maltose. In another specific embodiment, the inducing amount of maltose is an amount of maltose from 0.25% to 3%, and the non-inducing amount is no maltose. In another specific embodiment, the inducing amount of maltose is at least 3%, and the limiting amount is no maltose.

In some embodiments where the maltose-responsive promoter is wired to effect an "on" state of non-catabolic compound production in the presence of maltose, the inducing amount of maltose in the culture medium is at least 0.1% (weight maltose per volume of culture medium). In some embodiments, the inducing amount of maltose in the culture medium is at least 0.25%. In some embodiments, the inducing amount of maltose in the culture medium is at least 0.5%. In some embodiments, the inducing amount of maltose in the culture medium is at least 0.75%. In some embodiments, the inducing amount of maltose in the culture medium is at least 1.0%. In some embodiments, the inducing amount of maltose in the culture medium is at least 1.25%. In some embodiments, the inducing amount of maltose in the culture medium is at least 1.5%. In some embodiments, the inducing amount of maltose in the culture medium is at least 1.75%. In some embodiments, the inducing amount of maltose in the culture medium is at least 2.0%. In some embodiments, the inducing amount of maltose in the culture medium is at least 2.25%. In some embodiments, the inducing amount of maltose in the culture medium is at least 2.5%. In some embodiments, the inducing amount of maltose in the culture medium is at least 2.75%. In some embodiments, the inducing amount of maltose in the culture medium is at least 3.0%. In some embodiments, the inducing amount of maltose in the culture medium is at least 3.25%. In some embodiments, the inducing amount of maltose in the culture medium is at least 3.5%. In some embodiments, the inducing amount of maltose in the culture medium is at least 3.75%. In some embodiments, the inducing amount of maltose in the culture medium is at least 4.0%. In some embodiments, the inducing amount of maltose in the culture medium is at least 4.25%. In some embodiments, the inducing amount of maltose in the culture medium is at least 4.5%. In some embodiments, the inducing amount of maltose in the culture medium is at least 4.75%. In some embodiments, the inducing amount of maltose in the culture medium is at least 5.0%. In some embodiments, the inducing amount of maltose in the culture medium is between 5% and 50%. In some embodiments, the inducing amount of maltose in the culture medium is about 5%, 10%, 15%, 20%, 25%, 30%, 35%, 40% 45% or about 50%.

In some embodiments, the non-repressing amount of maltose is an amount that is at least 2-fold, 10-fold, 100-fold, 1000-fold, 10,000-fold or 100,000-fold less than a repressing amount of maltose as determined according to the methods described above. In some embodiments, the non-repressing amount of maltose is an amount that is at least 2-fold, 10-fold, 100-fold, 1000-fold, 10,000-fold or 100,000-fold less than the saturating amount of maltose as determined according to the methods described above. In some embodiments, the non-repressing amount of maltose is an amount that is less than 50%, less than 20%, less than 10%, less than 1%, less than 0.5%, less than 0.2%, less than 0.1%, less than 0.01%, or less than 0.001% of a repressing amount of maltose as determined according to the methods described above. In some embodiments, the non-repressing amount of maltose is an amount that is less than 50%, less than 20%, less than 10%, less than 1%, less than 0.1%, less than 0.01%, or less than 0.001% of the saturating amount of maltose as determined according to the methods described above. In a specific embodiment, the non-repressing amount of maltose is 0 mg/L (0%), i.e., no maltose. Thus, in this specific embodiment, the host cells are grown during the production stage in a cell culture medium that comprises no external source of maltose.

5.3.3 Production of Non-Catabolic Products

In some embodiments of the fermentation methods provided herein, utilizing either a microaerobic-responsive promoter in combination with manipulation of oxygen conditions, or a maltose-responsive promoter in combination with manipulation of maltose conditions, the production of the non-catabolic compound during the build stage (step (a) of the methods described above) is less than 50, 40, 30, 20 or 10% of the maximum non-catabolic compound production of the genetically modified host cell, e.g., the amount of non-catabolic compound production when the host cell is cultured during the production stage (step (b) of the methods described above).

The periods of time for during which the build stage and production stage of the fermentation process are carried out can vary, and will depend on factors such as the growth rates of the host cell, the intrinsic rate of growth of the host cell; and other culture conditions such as the pH, temperature, depending on the specific requirements of the host cell, the fermentation, and the process. However, any duration of the build stage is expected to result in some benefit to the final productivity of the fermentation, since some amount of the negative selective pressure associated with non-catabolic compound production is relieved in the "off" state.

In some embodiments, the build stage is carried out for a period of time sufficient to produce an amount of cellular biomass that can support production of the non-catabolic compound during the production stage. In some embodiments, the build stage is carried out for a period of time sufficient for the population present at the time of inoculation to undergo a plurality of doublings until a desired cell density is reached. In some embodiments, the build stage is carried out for a period of time sufficient for the host cell population to reach a cell density ($OD_{600}$) of between 0.01 and 400 in the fermentation vessel or container in which the build stage is being carried out. In some embodiments, the build stage is carried out until an $OD_{600}$ of at least 0.01 is reached. In some embodiments, the build stage is carried out until an $OD_{600}$ of at least 0.1 is reached. In some embodiments, the build stage is carried out until an $OD_{600}$ of at least 1.0 is reached. In some embodiments, the build stage is carried out until an $OD_{600}$ of at least 10 is reached. In some embodiments, the build stage is carried out until an $OD_{600}$ of at least 100 is reached. In some embodiments, the build stage is carried out until an $OD_{600}$ of between 0.01 and 100 is reached. In some embodiments, the build stage is carried out until an $OD_{600}$ of between 0.1 and 10 is reached. In some embodiments, the build stage is carried out until an $OD_{600}$ of between 1 and 100 is reached. In other embodiments, the build stage is carried for a period of at least 12, 24, 36, 48, 60, 72, 84, 96 or more than 96 hours.

In some embodiments, the production stage is carried out for a period of time sufficient to produce a desired amount of the non-catabolic compound. In some embodiments, the production stage is carried out for a period of at least 12, 24, 36, 48, 60, 72, 84, 96 or more than 96 hours. In some embodiments, the production stage is carried out for a period of between 3 and 20 days. In some embodiments, the production stage is carried for a period of 1, 2, 3, 4, 5, 6, 7, 8, 9, 10, 11, 12, 13, 14, 15, 16, 17, 18, 19, 20 or more than 20 days.

In a particular embodiment, the method of producing a non-catabolic compound comprises conducting fermentation of the genetically modified host cell under aerobic conditions sufficient to allow growth and maintenance of the genetically modified host cell; then subsequently providing microaerobic fermentation conditions sufficient to induce production of the non-catabolic compound, and maintaining the microaerobic conditions throughout the fermentation run.

In another embodiment, the method of producing a non-catabolic compound comprises culturing the host cells in separate build and production culture media. For example, the method can comprise culturing the genetically modified host cell in a build stage wherein the cell is cultured under non-producing conditions to produce an inoculum, then transferring the inoculum into a second fermentation medium under conditions suitable to induce compound production, and maintaining steady state conditions in the second fermentation stage to produce a cell culture containing a non-catabolic product.

In some embodiments, the method provided herein is sufficient for producing one or more non-catabolic compounds in an amount greater than about 10 grams per liter of fermentation medium. In some such embodiments, the non-catabolic derived compound is produced in an amount from about 10 to about 50 grams, more than about 15 grams, more than about 20 grams, more than about 25 grams, or more than about 30 grams per liter of cell culture.

In some embodiments, the method provided herein is sufficient for producing one or more non-catabolic compounds in an amount greater than about 50 milligrams per gram of dry cell weight. In some embodiments, the recombinantly produced non-catabolic compound is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the practice of the method provided herein results in increased production of the non-catabolic compound by the population of genetically modified host cells, compared to production resulting from a method not comprising a build stage during which the host cells are cultured under non-producing conditions. In some embodiments, the practice of the method results in the production of one or more non-catabolic compounds in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of non-catabolic compound produced by a method not comprising a build stage during which the host cells are cultured under non-producing conditions, on a per unit volume of cell culture basis.

In some embodiments, the practice of the method results in the production of one or more non-catabolic compounds in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of non-catabolic compound produced by a method not comprising a build stage during which the host cells are cultured under non-producing conditions, on a per unit dry cell weight basis.

In some embodiments, the practice of the method results in the production of one or more non-catabolic compounds in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of non-catabolic compound produced by a method not comprising a build stage during which the host cells are cultured under non-producing conditions, on a per unit volume of cell culture per unit time basis.

In some embodiments, the practice of the method results in the production of one or more non-catabolic compounds in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of non-catabolic compound produced by a method not comprising a build stage during which the host cells are cultured under non-producing conditions, on a per unit dry cell weight per unit time basis.

5.3.4 Culture Media and Conditions

Materials and methods for the maintenance and growth of microbial cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The methods of producing non-catabolic compounds provided herein may be performed in a suitable culture medium in a suitable container, including but not limited to a cell culture plate, a flask, or a fermentor. Further, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing Saccharomyces cerevisiae as the host cell, strains can be grown in a fermentor as described in detail by Kosaric, et al, in Ullmann's Encyclopedia of Industrial Chemistry, Sixth Edition, Volume 12, pages 398-473, Wiley-VCH Verlag GmbH & Co. KDaA, Weinheim, Germany. Further, the methods can be performed at any volume of fermentation, e.g., from lab scale (e.g., 10 ml to 20 L) to pilot scale (e.g., 20 L to 500 L) to industrial scale (e.g., 500 L to ≥500,000 L) fermentations.

In some embodiments, the culture medium for use in the methods of producing non-catabolic compounds as provided herein includes any culture medium in which a genetically modified microorganism capable of producing a non-catabolic compound can subsist, i.e., support and maintain growth and viability. In some embodiments, the culture medium, also promotes the biosynthetic pathway necessary to produce the desired non-catabolic compound.

In some embodiments, the culture medium is an aqueous medium comprising assimilable carbon, nitrogen and phosphate sources. Such a medium can also include appropriate salts, minerals, metals and other nutrients. In some embodiments, the carbon source and each of the essential cell nutrients are added incrementally or continuously to the fermentation media, and each required nutrient is maintained at essentially the minimum level needed for efficient assimilation by growing cells, for example, in accordance with a predetermined cell growth curve based on the metabolic or respiratory function of the cells which convert the carbon source to a biomass. Suitable conditions and suitable media for culturing microorganisms are well known in the art. In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol.

The concentration of a carbon source, such as glucose, in the culture medium should promote cell growth, but not be so high as to repress growth of the microorganism used. Typically, cultures are run with a carbon source, such as glucose, being added at levels to achieve the desired level of growth and biomass, but at undetectable levels (with detection limits being about <0.1 g/l). In other embodiments, the concentration of a carbon source, such as glucose, in the culture medium is greater than about 1 g/L, preferably greater than about 2 g/L, and more preferably greater than about 5 g/L. In addition, the concentration of a carbon source, such as glucose, in the culture medium is typically less than about 100 g/L, preferably less than about 50 g/L, and more preferably less than about 20 g/L. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of the nitrogen sources, in the culture medium is greater than about 0.1 g/L, preferably greater than about 0.25 g/L, and more preferably greater than about 1.0 g/L. Beyond certain concentrations, however, the addition of a nitrogen source to the culture medium is not advantageous for the growth of the microorganisms. As a result, the concentration of the nitrogen sources, in the culture medium is less than about 20 g/L, preferably less than about 10 g/L and more preferably less than about 5 g/L. Further, in some instances it may be desirable to allow the culture medium to become depleted of the nitrogen sources during culture.

The effective culture medium can contain other compounds such as inorganic salts, vitamins, trace metals or growth promoters. Such other compounds can also be present in carbon, nitrogen or mineral sources in the effective medium or can be added specifically to the medium.

The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the culture medium is greater than about 1.0 g/L, preferably greater than about 2.0 g/L and more preferably greater than about 5.0 g/L. Beyond certain concentrations, however, the addition of phosphate to the culture medium is not advantageous for the growth of the microorganisms. Accordingly, the concentration of phosphate in the culture medium is typically less than about 20 g/L, preferably less than about 15 g/L and more preferably less than about 10 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, preferably greater than about 1.0 g/L, and more preferably greater than about 2.0 g/L. Beyond certain concentrations, however, the addition of magnesium to the culture medium is not advantageous for the growth of the microorganisms. Accordingly, the concentration of magnesium in the culture medium is typically less than about 10 g/L, preferably less than about 5 g/L, and more preferably less than about 3 g/L. Further, in some instances it may be desirable to allow the culture medium to become depleted of a magnesium source during culture.

In some embodiments, the culture medium can also include a biologically acceptable chelating agent, such as the dihydrate of trisodium citrate. In such instance, the concentration of a chelating agent in the culture medium is greater than about 0.2 g/L, preferably greater than about 0.5 g/L, and more preferably greater than about 1 g/L. Beyond certain concentrations, however, the addition of a chelating agent to the culture medium is not advantageous for the growth of the microorganisms. Accordingly, the concentration of a chelating agent in the culture medium is typically less than about 10 g/L, preferably less than about 5 g/L, and more preferably less than about 2 g/L.

The culture medium can also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

The culture medium can also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, preferably within the range of from about 20 mg/L to about 1000 mg/L, and more preferably in the range of from about 50 mg/L to about 500 mg/L.

The culture medium can also include sodium chloride. Typically, the concentration of sodium chloride in the culture medium is within the range of from about 0.1 g/L to about 5 g/L, preferably within the range of from about 1 g/L to about 4 g/L, and more preferably in the range of from about 2 g/L to about 4 g/L.

In some embodiments, the culture medium can also include trace metals. Such trace metals can be added to the culture medium as a stock solution that, for convenience, can be prepared separately from the rest of the culture medium. Typically, the amount of such a trace metals solution added to the culture medium is greater than about 1 ml/L, preferably greater than about 5 mL/L, and more preferably greater than about 10 mL/L. Beyond certain concentrations, however, the addition of a trace metals to the culture medium is not advantageous for the growth of the microorganisms. Accordingly, the amount of such a trace metals solution added to the culture medium is typically less than about 100 mL/L, preferably less than about 50 mL/L, and more preferably less than about 30 mL/L. It should be noted that, in addition to adding trace metals in a stock solution, the individual components can be added separately, each within ranges corresponding independently to the amounts of the components dictated by the above ranges of the trace metals solution.

The culture media can include other vitamins, such as biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture during the production stage of the fermentation. In some embodiments, the culture may be supplemented with relatively high concentrations of such components at the outset, for example, of the production stage, so that growth and/or non-catabolic compound production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, a small amount of anti-foaming agent may be added during the culture.

The temperature of the culture medium can be any temperature suitable for growth of the genetically modified cells and/or production of non-catabolic compounds. For example, prior to inoculation of the culture medium with an inoculum, the culture medium can be brought to and maintained at a temperature in the range of from about 20° C. to about 45° C., preferably to a temperature in the range of from about 25° C. to about 40° C., and more preferably in the range of from about 28° C. to about 32° C.

The pH of the culture medium can be controlled by the addition of acid or base to the culture medium. In such cases when ammonia is used to control pH, it also conveniently serves as a nitrogen source in the culture medium. Preferably, the pH is maintained from about 3.0 to about 8.0, more preferably from about 3.5 to about 7.0, and most preferably from about 4.0 to about 6.5.

In some embodiments, the carbon source concentration, such as the maltose or glucose concentration, of the culture medium is monitored during culture. Glucose concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium, and maltose levels may be similarly monitored. As stated previously, the carbon source concentration should be kept below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose is used as a carbon source the glucose is preferably fed to the fermentor and maintained below detection limits. Alternatively, the glucose concentration in the culture medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is acceptable, and may be preferred, to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

5.3.5 Recovery of Non-Catabolic Compounds

Once the non-catabolic is produced by the host cell, it may be recovered or isolated for subsequent use using any suitable separation and purification methods known in the art. In some embodiments, an organic phase comprising the non-catabolic is separated from the fermentation by centrifugation. In other embodiments, an organic phase comprising the non-catabolic compound separates from the fermentation spontaneously. In other embodiments, an organic phase comprising the non-catabolic derived compound is separated from the fermentation by adding a deemulsifier and/or a nucleating agent into the fermentation reaction. Illustrative examples of deemulsifiers include flocculants and coagulants. Illustrative examples of nucleating agents include droplets of the non-catabolic compound itself and organic solvents such as dodecane, isopropyl myristrate, and methyl oleate.

The non-catabolic compound produced in these cells may be present in the culture supernatant and/or associated with the host cells. In embodiments where the non-catabolic compound is associated with the host cell, the recovery of the non-catabolic may comprise a method of permeabilizing or lysing the cells. Alternatively or simultaneously, the non-catabolic in the culture medium can be recovered using a recovery process including, but not limited to, chromatography, extraction, solvent extraction, membrane separation, electrodialysis, reverse osmosis, distillation, chemical derivatization and crystallization.

In some embodiments, the non-catabolic compound is separated from other products that may be present in the organic phase. In some embodiments, separation is achieved using adsorption, distillation, gas-liquid extraction (stripping), liquid-liquid extraction (solvent extraction), ultrafiltration, and standard chromatographic techniques.

In some embodiments, the recovered non-catabolic compound is pure, e.g., at least about 40% pure, at least about 50% pure, at least about 60% pure, at least about 70% pure, at least about 80% pure, at least about 90% pure, at least about 95% pure, at least about 98% pure, or more than 98% pure, where "pure" in the context of a non-catabolic compound refers to a non-catabolic compound that is free from other non-catabolic compounds, contaminants, etc.

5.4 Genetically Modified Microorganisms

Provided herein are genetically modified microorganisms (e.g., a genetically modified *Saccharomyces cerevisiae* cell) that produce heterologous acetyl-CoA derived (non-catabolic) compound. The genetically modified microorganisms produce greater amounts of one or more compounds biosynthesized from acetyl-CoA compared to a parent microorganism lacking the genetic modifications described herein.

Methods for genetically modifying microbes using expression vectors or chromosomal integration constructs, e.g., to effect increased production of one or more non-catabolic compounds in a host cell, are well known in the art. See, for example, Sherman, F., et al., *Methods Yeast Genetics*, Cold Spring Harbor Laboratory, N.Y. (1978); Guthrie, C., et al. (Eds.) *Guide To Yeast Genetics and Molecular Biology* Vol. 194, Academic Press, San Diego (1991); Sambrook et al., 2001, *Molecular Cloning—A Laboratory Manual*, $3^{rd}$ edition, Cold Spring Harbor Laboratory, Cold Spring Harbor, N.Y.; and Ausubel et al., eds., Current Edition, *Current Protocols in Molecular Biology*, Greene Publishing Associates and Wiley Interscience, NY.; the disclosures of which are incorporated herein by reference. In addition, inhibition of gene expression, e.g., which results in increased production of one or more non-catabolic compounds in the cell, may be accomplished by deletion, mutation, and/or gene rearrangement. It can also be carried out with the use of antisense RNA, siRNA, miRNA, ribozymes, triple stranded DNA, and transcription and/or translation inhibitors. In addition, transposons can be employed to disrupt gene expression, for example, by inserting it between the promoter and the coding region, or between two adjacent genes to inactivate one or both genes.

In some embodiments, increased production of non-catabolic compound in the cell is effected by the use of expression vectors to express a particular protein, e.g., a protein involved in a biosynthetic pathway as described above. Generally, expression vectors are recombinant polynucleotide molecules comprising replication signals and expression control sequences, e.g., promoters and terminators, operatively linked to a nucleotide sequence encoding a polypeptide. Expression vectors useful for expressing polypeptide-encoding nucleotide sequences include viral vectors (e.g., retroviruses, adenoviruses and adeno-associated viruses), plasmid vectors, and cosmids. Illustrative examples of expression vectors suitable for use in yeast cells include, but are not limited to CEN/ARS and 2μ plasmids. Illustrative examples of promoters suitable for use in yeast cells include, but are not limited to the promoter of the TEF1 gene of *K. lactis*, the promoter of the PGK1 gene of *Saccharomyces cerevisiae*, the promoter of the TDH3 gene of *Saccharomyces cerevisiae*, repressible promoters, e.g., the promoter of the CTR3 gene of *Saccharomyces cerevisiae*, and inducible promoters, e.g., galactose inducible promoters of *Saccharomyces cerevisiae* (e.g., promoters of the GAL1, GAL7, and GAL10 genes).

Expression vectors and chromosomal integration constructs can be introduced into microbial cells by any method known to one of skill in the art without limitation. See, for example, Hinnen et al., *Proc. Natl. Acad. Sci. USA* 75:1292-3 (1978); Cregg et al., *Mol. Cell. Biol.* 5:3376-3385 (1985); U.S. Pat. No. 5,272,065; Goeddel et al., eds, 1990, Methods in Enzymology, vol. 185, Academic Press, Inc., CA; Krieger, 1990, *Gene Transfer and Expression—A Laboratory Manual*, Stockton Press, NY; Sambrook et al., 1989, *Molecular Cloning—A Laboratory Manual*, Cold Spring Harbor Laboratory, NY; and Ausubel et al., eds., Current Edition, *Current Protocols in Molecular Biology*, Greene Publishing Associates and Wiley Interscience, NY. Exemplary techniques include, but are not limited to, spheroplasting, electroporation, PEG 1000 mediated transformation, and lithium acetate or lithium chloride mediated transformation.

5.4.1 Host Cells

Cells useful in the methods and compositions provided herein include any cell capable of naturally or recombinantly producing a non-catabolic compound, e.g., an isoprenoid, a polyketide, a fatty acid, and the like. In some embodiments, the cell is a prokaryotic cell. In some embodiments, the cell is a bacterial cell. In some embodiments, the cell is an *Escherichia coli* cell. In some embodiments, the cell is a eukaryotic cell. In some embodiments, the cell is a mammalian cell. In some embodiments, the cell is a Chinese hamster ovary (CHO) cell, a COS-7 cell, a mouse fibroblast cell, a mouse embryonal carcinoma cell, or a mouse embryonic stem cell. In some embodiments, the cell is an insect cell. In some embodiments, the cell is a S2 cell, a Schneider cell, a S12 cell, a 5B1-4 cell, a Tn5 cell, or a Sf9 cell. In some embodiments, the cell is a unicellular eukaryotic organism cell.

In some embodiments, the cell is a mycelial bacterial cell. In some embodiments, the mycelial bacterial cell is of the class actinomycetes. In particular embodiments, the mycelial bacterial cell is of the genera *Streptomyces*, for example, *Streptomyces ambofaciens, Streptomyces avermitilis, Streptomyces azureus, Streptomyces cinnamonensis, Streptomyces coelicolor, Streptomyces curacoi, Streptomyces erythraeus, Streptomyces fradiae, Streptomyces galilaeus, Streptomyces glaucescens, Streptomyces hygroscopicus, Streptomyces lividans, Streptomyces parvulus, Streptomyces peucetius, Streptomyces rimosus, Streptomyces roseofulvus, Streptomyces thermotolerans, Streptomyces violaceoruber.*

In another embodiment, the cell is a fungal cell. In a more particular embodiment, the cell is a yeast cell. Yeasts useful in the methods and compositions provided herein include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces,*

*Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis*, and *Zygozyma*, among others.

In particular embodiments, useful yeasts in the methods and compositions provided herein include *Saccharomyces cerevisiae, Pichia pastoris, Schizosaccharomyces pombe, Dekkera bruxellensis, Kluyveromyces lactis* (previously called *Saccharomyces lactis*), *Kluveromyces marxianus, Arxula adeninivorans,* or *Hansenula polymorpha* (now known as *Pichia angusta*). In some embodiments, the microbe is a strain of the genus *Candida*, such as *Candida lipolytica, Candida guilliermondii, Candida krusei, Candida pseudotropicalis,* or *Candida utilis*.

In a particular embodiment, the cell is a *Saccharomyces cerevisiae* cell. In some embodiments, the strain of the *Saccharomyces cerevisiae* cell is selected from the group consisting of Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-i, CB-1, NR-1, BT-1, and AL-1. In some embodiments, the strain of *Saccharomyces cerevisiae* is selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the cell is a haploid microbial cell. In other embodiments, the cell is a diploid microbial cell. In some embodiments, the cell is heterozygous. In other embodiments, the cell is homozygous other than for its mating type allele (i.e., if the cell should sporulate, the resulting four haploid microbial cells would be genetically identical except for their mating type allele, which in two of the haploid cells would be mating type a and in the other two haploid cells would be mating type alpha).

In some embodiments, the cell is a cell that is suitable for industrial fermentation, e.g., bioethanol fermentation. In particular embodiments, the cell is conditioned to subsist under high solvent concentration, high temperature, expanded substrate utilization, nutrient limitation, osmotic stress due, acidity, sulfite and bacterial contamination, or combinations thereof, which are recognized stress conditions of the industrial fermentation environment.

Exemplary non-catabolic compound producing cells, e.g., cells recombinantly producing isoprenoids, polyketides, and fatty acids, and methods for generating such cells, are provided below.

5.5 Production of Isoprenoids

In some embodiments, the non-catabolic compound is an isoprenoid. Isoprenoids are derived from isopentenyl pyrophosphate (IPP), which can be biosynthesized by enzymes of the mevalonate-dependent ("MEV") pathway or the 1-deoxy-D-xylulose 5-diphosphate ("DXP") pathway.

5.5.1 MEV Pathway

In some embodiments of the methods provided herein, the genetically modified microorganism comprises one or more heterologous nucleotide sequences encoding one or more enzymes of the MEV pathway, which effects increased production of one or more isoprenoid compounds as compared to a genetically unmodified parent cell.

In some embodiments, the isoprenoid producing cell comprises a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC_000913 REGION: 2324131.2325315; *Escherichia coli*), (D49362; *Paracoccus denitrificans*), and (L20428; *Saccharomyces cerevisiae*).

In some embodiments, the isoprenoid producing cell comprises a heterologous nucleotide sequence encoding an enzyme that can condense acetoacetyl-CoA with another molecule of acetyl-CoA to form 3-hydroxy-3-methylglutaryl-CoA (HMG-CoA), e.g., a HMG-CoA synthase. Illustrative examples of nucleotide sequences encoding such an enzyme include, but are not limited to: (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

In some embodiments, the isoprenoid producing cell comprises a heterologous nucleotide sequence encoding an enzyme that can convert HMG-CoA into mevalonate, e.g., a HMG-CoA reductase. Illustrative examples of nucleotide sequences encoding such an enzyme include, but are not limited to: (NM_206548; *Drosophila melanogaster*), (NC_002758, Locus tag SAV2545, GeneID 1122570; *Staphylococcus aureus*), (NM_204485; *Gallus gallus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734.118898; *Saccharomyces cerevisiae*).

In some embodiments, the isoprenoid producing cell comprises a heterologous nucleotide sequence encoding an enzyme that can convert mevalonate into mevalonate 5-phosphate, e.g., a mevalonate kinase. Illustrative examples of nucleotide sequences encoding such an enzyme include, but are not limited to: (L77688; *Arabidopsis thaliana*), and (X55875; *Saccharomyces cerevisiae*).

In some embodiments, the isoprenoid producing cell comprises a heterologous nucleotide sequence encoding an enzyme that can convert mevalonate 5-phosphate into mevalonate 5-pyrophosphate, e.g., a phosphomevalonate kinase. Illustrative examples of nucleotide sequences encoding such an enzyme include, but are not limited to: (AF429385; *Hevea brasiliensis*), (NM_006556; *Homo sapiens*), and (NC_001145. complement 712315.713670; *Saccharomyces cerevisiae*).

In some embodiments, the isoprenoid producing cell comprises a heterologous nucleotide sequence encoding an enzyme that can convert mevalonate 5-pyrophosphate into IPP, e.g., a mevalonate pyrophosphate decarboxylase. Illustrative examples of nucleotide sequences encoding such an enzyme include, but are not limited to: (X97557; *Saccha-* romyces cerevisiae), (AF290095; *Enterococcus faecium*), and (U49260; *Homo sapiens*).

In some embodiments, the isoprenoid producing cell comprises one or more heterologous nucleotide sequences encoding more than one enzyme of the MEV pathway. In some embodiments, the isoprenoid producing cell comprises one or more heterologous nucleotide sequences encoding two enzymes of the MEV pathway. In some embodiments, the isoprenoid producing cell comprises one or more heterologous nucleotide sequences encoding an enzyme that can convert HMG-CoA into mevalonate and an enzyme that can convert mevalonate into mevalonate 5-phosphate. In some embodiments, the isoprenoid producing cell comprises one or more heterologous nucleotide sequences encoding three enzymes of the MEV pathway. In some embodiments, the isoprenoid producing cell comprises one or more heterologous nucleotide sequences encoding four enzymes of the MEV pathway. In some embodiments, the isoprenoid producing cell comprises one or more heterologous nucleotide sequences encoding five enzymes of the MEV pathway. In some embodiments, the isoprenoid producing cell comprises one or more heterologous nucleotide sequences encoding six enzymes of the MEV pathway.

In some embodiments, the isoprenoid producing cell further comprises a heterologous nucleotide sequence encoding an enzyme that can convert IPP generated via the MEV pathway into its isomer, dimethylallyl pyrophosphate ("DMAPP"). DMAPP can be condensed and modified through the action of various additional enzymes to form simple and more complex isoprenoids (FIG. 2).

5.5.2 DXP Pathway

In some embodiments of the methods provided herein, the isoprenoid producing cell comprises one or more heterologous nucleotide sequences encoding one or more enzymes of the DXP pathway, which effects increased production of one or more isoprenoid compounds as compared to a genetically unmodified parent cell.

In some embodiments, the isoprenoid producing cell comprises a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC_000913 REGION: 2324131.2325315; *Escherichia coli*), (D49362; *Paracoccus denitrificans*), and (L20428; *Saccharomyces cerevisiae*).

In some embodiments, the isoprenoid producing cell comprises a heterologous nucleotide sequence encoding an enzyme, e.g., 1-deoxy-D-xylulose-5-phosphate synthase, which can condense pyruvate with D-glyceraldehyde 3-phosphate to make 1-deoxy-D-xylulose-5-phosphate. Illustrative examples of nucleotide sequences encoding such an enzyme include but are not limited to: (AF035440; *Escherichia coli*), (NC_002947, locus tag PP0527; *Pseudomonas putida* KT2440), (CP000026, locus tag SPA2301; *Salmonella enterica Paratyphi*, see ATCC 9150), (NC_007493, locus tag RSP_0254; *Rhodobacter sphaeroides* 2.4.1), (NC_005296, locus tag RPA0952; *Rhodopseudomonas palustris* CGA009), (NC_004556, locus tag PD1293; *Xylella fastidiosa Temecula1*), and (NC_003076, locus tag AT5G11380; *Arabidopsis thaliana*).

In some embodiments, the isoprenoid producing cell comprises a heterologous nucleotide sequence encoding an enzyme, e.g., 1-deoxy-D-xylulose-5-phosphate reductoisomerase, which can convert 1-deoxy-D-xylulose-5-phosphate to 2C-methyl-D-erythritol-4-phosphate. Illustrative examples of nucleotide sequences include but are not limited to: (AB013300; *Escherichia coli*), (AF148852; *Arabidopsis thaliana*), (NC_002947, locus tag PP1597; *Pseudomonas putida* KT2440), (AL939124, locus tag SCO5694; *Streptomyces coelicolor* A3(2)), (NC_007493, locus tag RSP_2709; *Rhodobacter sphaeroides* 2.4.1), and (NC_007492, locus tag Pfl_1107; *Pseudomonas fluorescens* PfO-1).

In some embodiments, the isoprenoid producing cell comprises a heterologous nucleotide sequence encoding an enzyme, e.g., 4-diphosphocytidyl-2C-methyl-D-erythritol synthase, which can convert 2C-methyl-D-erythritol-4-phosphate to 4-diphosphocytidyl-2C-methyl-D-erythritol. Illustrative examples of nucleotide sequences include but are not limited to: (AF230736; *Escherichia coli*), (NC_007493, locus tag RSP_2835; *Rhodobacter sphaeroides* 2.4.1), (NC_003071, locus tag AT2G02500; *Arabidopsis thaliana*), and (NC_002947, locus tag PP1614; *Pseudomonas putida* KT2440).

In some embodiments, the isoprenoid producing cell comprises a heterologous nucleotide sequence encoding an enzyme, e.g., 4-diphosphocytidyl-2C-methyl-D-erythritol kinase, which can convert 4-diphosphocytidyl-2C-methyl-D-erythritol to 4-diphosphocytidyl-2C-methyl-D-erythritol-2-phosphate. Illustrative examples of nucleotide sequences include but are not limited to: (AF216300; *Escherichia coli*) and (NC_007493, locus tag RSP_1779; *Rhodobacter sphaeroides* 2.4.1).

In some embodiments, the isoprenoid producing cell comprises a heterologous nucleotide sequence encoding an enzyme, 2C-methyl-D-erythritol 2,4-cyclodiphosphate synthase, which can convert 4-diphosphocytidyl-2C-methyl-D-erythritol-2-phosphate to 2C-methyl-D-erythritol 2,4-cyclodiphosphate. Illustrative examples of nucleotide sequences include but are not limited to: (AF230738; *Escherichia coli*), (NC_007493, locus tag RSP_6071; *Rhodobacter sphaeroides* 2.4.1), and (NC_002947, locus tag PP1618; *Pseudomonas putida* KT2440).

In some embodiments, the isoprenoid producing cell comprises a heterologous nucleotide sequence encoding an enzyme, e.g., 1-hydroxy-2-methyl-2-(E)-butenyl-4-diphosphate synthase, which can convert 2C-methyl-D-erythritol 2,4-cyclodiphosphate to 1-hydroxy-2-methyl-2-(E)-butenyl-4-diphosphate. Illustrative examples of nucleotide sequences include but are not limited to: (AY033515; *Escherichia coli*), (NC_002947, locus tag PP0853; *Pseudomonas putida* KT2440), and (NC_007493, locus tag RSP_2982; *Rhodobacter sphaeroides* 2.4.1).

In some embodiments, the isoprenoid producing cell comprises a heterologous nucleotide sequence encoding an enzyme, e.g., isopentyl/dimethylallyl diphosphate synthase, which can convert 1-hydroxy-2-methyl-2-(E)-butenyl-4-diphosphate into either IPP or its isomer, DMAPP. Illustrative examples of nucleotide sequences include but are not limited to: (AY062212; *Escherichia coli*) and (NC_002947, locus tag PP0606; *Pseudomonas putida* KT2440).

In some embodiments, the isoprenoid producing cell comprises one or more heterologous nucleotide sequences encoding more than one enzyme of the DXP pathway. In some embodiments, the isoprenoid producing cell comprises one or more heterologous nucleotide sequences encoding two enzymes of the DXP pathway. In some embodiments, the isoprenoid producing cell comprises one or more heterologous nucleotide sequences encoding three enzymes of the DXP pathway. In some embodiments, the isoprenoid producing cell comprises one or more heterologous nucleotide sequences encoding four enzymes of the DXP pathway. In some embodiments, the isoprenoid producing cell comprises one or more heterologous nucleotide sequences encoding five enzymes of the DXP pathway. In some embodiments, the isoprenoid producing cell comprises one or more heterologous nucleotide sequences encoding six enzymes of the DXP pathway. In some embodiments, the isoprenoid producing cell comprises one or more heterologous nucleotide sequences encoding five enzymes of the DXP pathway. In some embodiments, the isoprenoid producing cell comprises one or more heterologous nucleotide sequences encoding seven enzymes of the DXP pathway.

In some embodiments, "cross talk" (or interference) between the host cell's own metabolic processes and those processes involved with the production of IPP are minimized or eliminated entirely. For example, cross talk is minimized or eliminated entirely when the host microorganism relies exclusively on the DXP pathway for synthesizing IPP, and a MEV pathway is introduced to provide additional IPP. Such a host organism would not be equipped to alter the expression of the MEV pathway enzymes or process the intermediates associated with the MEV pathway. Organisms that rely exclusively or predominately on the DXP pathway include, for example, Escherichia coli.

In some embodiments, the host cell produces IPP via the MEV pathway, either exclusively or in combination with the DXP pathway. In other embodiments, a host's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

In some embodiments, the isoprenoid produced by the cell is a $C_5$ isoprenoid. These compounds are derived from one isoprene unit and are also called hemiterpenes. An illustrative example of a hemiterpene is isoprene. In other embodiments, the isoprenoid is a $C_{10}$ isoprenoid. These compounds are derived from two isoprene units and are also called monoterpenes. Illustrative examples of monoterpenes are limonene, citranellol, geraniol, menthol, perillyl alcohol, linalool, thujone, and myrcene. In other embodiments, the isoprenoid is a $C_{15}$ isoprenoid. These compounds are derived from three isoprene units and are also called sesquiterpenes. Illustrative examples of sesquiterpenes are periplanone B, gingkolide B, amorphadiene, artemisinin, artemisinic acid, valencene, nootkatone, epi-cedrol, epi-aristolochene, farnesol, gossypol, sanonin, periplanone, forskolin, and patchoulol (which is also known as patchouli alcohol). In other embodiments, the isoprenoid is a $C_{20}$ isoprenoid. These compounds are derived from four isoprene units and also called diterpenes. Illustrative examples of diterpenes are casbene, eleutherobin, paclitaxel, prostratin, pseudopterosin, and taxadiene. In yet other examples, the isoprenoid is a $C_{20+}$ isoprenoid. These compounds are derived from more than four isoprene units and include: triterpenes ($C_{30}$ isoprenoid compounds derived from 6 isoprene units) such as arbrusideE, bruceantin, testosterone, progesterone, cortisone, digitoxin, and squalene; tetraterpenes ($C_{40}$ isoprenoid compounds derived from 8 isoprenoids) such as β-carotene; and polyterpenes ($C_{40+}$ isoprenoid compounds derived from more than 8 isoprene units) such as polyisoprene. In some embodiments, the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene and valencene. Isoprenoid compounds also include, but are not limited to, carotenoids (such as lycopene, α- and β-carotene, α- and β-cryptoxanthin, bixin, zeaxanthin, astaxanthin, and lutein), steroid compounds, and compounds that are composed of isoprenoids modified by other chemical groups, such as mixed terpene-alkaloids, and coenzyme Q-10.

In some embodiments, the isoprenoid producing cell further comprises a heterologous nucleotide sequence encoding an enzyme that can convert IPP generated via the MEV pathway into DMAPP, e.g., an IPP isomerase. Illustrative examples of nucleotide sequences encoding such an enzyme include, but are not limited to: (NC_000913, 3031087.3031635; Escherichia coli), and (AF082326; Haematococcus pluvialis).

In some embodiments, the isoprenoid producing cell further comprises a heterologous nucleotide sequence encoding a polyprenyl synthase that can condense IPP and/or DMAPP molecules to form polyprenyl compounds containing more than five carbons.

In some embodiments, the isoprenoid producing cell comprises a heterologous nucleotide sequence encoding an enzyme that can condense one molecule of IPP with one molecule of DMAPP to form one molecule of geranyl pyrophosphate ("GPP"), e.g., a GPP synthase.

Illustrative examples of nucleotide sequences encoding such an enzyme include, but are not limited to: (AF513111; Abies grandis), (AF513112; Abies grandis), (AF513113; Abies grandis), (AY534686; Antirrhinum majus), (AY534687; Antirrhinum majus), (Y17376; Arabidopsis thaliana), (AE016877, Locus AP11092; Bacillus cereus; ATCC 14579), (AJ243739; Citrus sinensis), (AY534745; Clarkia breweri), (AY953508; Ips pini), (DQ286930; Lycopersicon esculentum), (AF182828; Mentha xpiperita), (AF182827; Mentha xpiperita), (MPI249453; Menthaxpiperita), (PZE431697, Locus CAD24425; Paracoccus zeaxanthinifaciens), (AY866498; Picrorhiza kurrooa), (AY351862; Vitis vinifera), and (AF203881, Locus AAF12843; Zymomonas mobilis).

In some embodiments, the isoprenoid producing cell comprises a heterologous nucleotide sequence encoding an enzyme that can condense two molecules of IPP with one molecule of DMAPP, or add a molecule of IPP to a molecule of GPP, to form a molecule of farnesyl pyrophosphate ("FPP"), e.g., a FPP synthase. Illustrative examples of nucleotide sequences that encode such an enzyme include, but are not limited to: (ATU80605; Arabidopsis thaliana), (ATHFPS2R; Arabidopsis thaliana), (AAU36376; Artemisia annua), (AF461050; Bos taurus), (D00694; Escherichia coli K-12), (AE009951, Locus AAL95523; Fusobacterium nucleatum subsp. nucleatum ATCC 25586), (GFFPPSGEN; Gibberella fujikuroi), (CP000009, Locus AAW60034; Gluconobacter oxydans 621H), (AF019892; Helianthus annuus), (HUMFAPS; Homo sapiens), (KLPFPSQCR; Kluyveromyces lactis), (LAU15777; Lupinus albus), (LAU20771; Lupinus albus), (AF309508; Mus musculus), (NCFPPSGEN; Neurospora crassa), (PAFPS1; Parthenium argentatum), (PAFPS2; Parthenium argentatum), (RATFAPS; Rattus norvegicus), (YSCFPP; Saccharomyces cerevisiae), (D89104; Schizosaccharomyces pombe), (CP000003, Locus AAT87386; Streptococcus pyogenes), (CP000017, Locus AAZ51849; Streptococcus pyogenes), (NC_008022, Locus YP_598856; Streptococcus pyogenes MGAS 10270), (NC_008023, Locus YP_600845; Streptococcus pyogenes MGAS2096), (NC_008024, Locus YP_602832; Streptococcus pyogenes MGAS 10750), (MZEFPS; Zea mays), (AE000657, Locus AAC06913; Aquifex aeolicus VF5), (NM_202836; Arabidopsis thaliana), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans serovar Copenhageni str. Fiocruz* L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus pneumoniae* R6), and (NC_004556, Locus NP 779706; *Xylella fastidiosa* Temecula1).

In some embodiments, the isoprenoid producing cell further comprises a heterologous nucleotide sequence encoding an enzyme that can combine IPP and DMAPP or IPP and FPP to form geranylgeranyl pyrophosphate ("GGPP"). Illustrative examples of nucleotide sequences that encode such an enzyme include, but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP_00743052; *Bacillus thuringiensis serovar israelensis*, ATCC 35646 sq1563), (CRGGPPS; *Catharanthus roseus*), (NZ_AABF02000074, Locus ZP_00144509; *Fusobacterium nucleatum* subsp. *vincentii*, ATCC 49256), (GFGGPPSGN; *Gibberella fujikuroi*), (AY371321; *Ginkgo biloba*), (AB055496; *Hevea brasiliensis*), (AB017971; *Homo sapiens*), (MCI276129; *Mucor circinelloides F. lusitanicus*), (AB016044; *Mus musculus*), (AABX01000298, Locus NCU01427; *Neurospora crassa*), (NCU20940; *Neurospora crassa*), (NZ_AAKL01000008, Locus ZP_00943566; *Ralstonia solanacearum* UW551), (AB 118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC_007759, Locus YP_461832; *Syntrophus acidotrophicus* SB), (NC_006840, Locus YP_204095; *Vibrio fischeri* ES 114), (NM_112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF 195122, Locus AAF24294; *Rhodobacter sphaeroides*), and (NC_004350, Locus NP_721015; *Streptococcus mutans* UA159).

In some embodiments, the isoprenoid producing cell further comprises a heterologous nucleotide sequence encoding an enzyme that can modify a polyprenyl to form a hemiterpene, a monoterpene, a sesquiterpene, a diterpene, a triterpene, a tetraterpene, a polyterpene, a steroid compound, a carotenoid, or a modified isoprenoid compound.

In some embodiments, the heterologous nucleotide encodes a carene synthase. Illustrative examples of suitable nucleotide sequences include, but are not limited to: (AF461460, REGION 43.1926; *Picea abies*) and (AF527416, REGION: 78.1871; *Salvia stenophylla*).

In some embodiments, the heterologous nucleotide encodes a geraniol synthase. Illustrative examples of suitable nucleotide sequences include, but are not limited to: (AJ457070; *Cinnamomum tenuipilum*), (AY362553; *Ocimum basilicum*), (DQ234300; *Perilla frutescens* strain 1864), (DQ234299; *Perilla citriodora* strain 1861), (DQ234298; *Perilla citriodora* strain 4935), and (DQ088667; *Perilla citriodora*).

In some embodiments, the heterologous nucleotide encodes a linalool synthase. Illustrative examples of a suitable nucleotide sequence include, but are not limited to: (AF497485; *Arabidopsis thaliana*), (AC002294, Locus AAB71482; *Arabidopsis thaliana*), (AY059757; *Arabidopsis thaliana*), (NM_104793; *Arabidopsis thaliana*), (AF154124; *Artemisia annua*), (AF067603; *Clarkia breweri*), (AF067602; *Clarkia concinna*), (AF067601; *Clarkia breweri*), (U58314; *Clarkia breweri*), (AY840091; *Lycopersicon esculentum*), (DQ263741; *Lavandula angustifolia*), (AY083653; *Mentha citrate*), (AY693647; *Ocimum basilicum*), (XM_463918; *Oryza sativa*), (AP004078, Locus BAD07605; *Oryza sativa*), (XM_463918, Locus XP_463918; *Oryza sativa*), (AY917193; *Perilla citriodora*), (AF271259; *Perilla frutescens*), (AY473623; *Picea abies*), (DQ195274; *Picea sitchensis*), and (AF444798; *Perilla frutescens* var. crispa cultivar No. 79).

In some embodiments, the heterologous nucleotide encodes a limonene synthase. Illustrative examples of suitable nucleotide sequences include, but are not limited to: (+)-limonene synthases (AF514287, REGION: 47.1867; *Citrus limon*) and (AY055214, REGION: 48.1889; *Agastache rugosa*) and (−)-limonene synthases (DQ195275, REGION: 1.1905; *Picea sitchensis*), (AF006193, REGION: 73.1986; *Abies grandis*), and (MHC4SLSP, REGION: 29.1828; *Mentha spicata*).

In some embodiments, the heterologous nucleotide encodes a myrcene synthase. Illustrative examples of suitable nucleotide sequences include, but are not limited to: (U87908; *Abies grandis*), (AY195609; *Antirrhinum majus*), (AY195608; *Antirrhinum majus*), (NM_127982; *Arabidopsis thaliana* TPS10), (NM_113485; *Arabidopsis thaliana* ATTPS-CIN), (NM_113483; *Arabidopsis thaliana* ATTPS-CIN), (AF271259; *Perilla frutescens*), (AY473626; *Picea abies*), (AF369919; *Picea abies*), and (AJ304839; *Quercus ilex*).

In some embodiments, the heterologous nucleotide encodes an ocimene synthase. Illustrative examples of suitable nucleotide sequences include, but are not limited to: (AY195607; *Antirrhinum majus*), (AY195609; *Antirrhinum majus*), (AY195608; *Antirrhinum majus*), (AK221024; *Arabidopsis thaliana*), (NM_113485; *Arabidopsis thaliana* ATTPS-CIN), (NM_113483; *Arabidopsis thaliana* ATTPS-CIN), (NM_117775; *Arabidopsis thaliana* ATTPS03), (NM_001036574; *Arabidopsis thaliana* ATTPS03), (NM_127982; *Arabidopsis thaliana* TPS10), (AB110642; *Citrus unshiu* CitMTSL4), and (AY575970; *Lotus corniculatus* var. *japonicus*).

In some embodiments, the heterologous nucleotide encodes an α-pinene synthase. Illustrative examples of suitable nucleotide sequences include, but are not limited to: (+) α-pinene synthase (AF543530, REGION: 1.1887; *Pinus taeda*), (−)α-pinene synthase (AF543527, REGION: 32.1921; *Pinus taeda*), and (+)/(−)α-pinene synthase (AGU87909, REGION: 6111892; *Abies grandis*).

In some embodiments, the heterologous nucleotide encodes a β-pinene synthase. Illustrative examples of suitable nucleotide sequences include, but are not limited to: (−) β-pinene synthases (AF276072, REGION: 1.1749; *Artemisia annua*) and (AF514288, REGION: 26.1834; *Citrus limon*).

In some embodiments, the heterologous nucleotide encodes a sabinene synthase. An illustrative example of a suitable nucleotide sequence includes but is not limited to AF051901, REGION: 26.1798 from *Salvia officinalis*.

In some embodiments, the heterologous nucleotide encodes a γ-terpinene synthase. Illustrative examples of suitable nucleotide sequences include, but are not limited to:

(AF514286, REGION: 30.1832 from *Citrus limon*) and (AB110640, REGION 1.1803 from *Citrus unshiu*).

In some embodiments, the heterologous nucleotide encodes a terpinolene synthase. Illustrative examples of a suitable nucleotide sequence include but are not limited to: (AY693650 from *Oscimum basilicum*) and (AY906866, REGION: 10.1887 from *Pseudotsuga menziesii*).

In some embodiments, the heterologous nucleotide encodes an amorphadiene synthase. An illustrative example of a suitable nucleotide sequence is SEQ ID NO. 37 of U.S. Patent Publication No. 2004/0005678.

In some embodiments, the heterologous nucleotide encodes a α-farnesene synthase. Illustrative examples of suitable nucleotide sequences include, but are not limited to DQ309034 from *Pyrus communis cultivar d'Anjou* (pear; gene name AFS1) and AY182241 from *Malus domestica* (apple; gene AFS 1). Pechouus et al., *Planta* 219(1):84-94 (2004).

In some embodiments, the heterologous nucleotide encodes a β-farnesene synthase. Illustrative examples of suitable nucleotide sequences include, but are not limited to GenBank accession number AF024615 from *Mentha×piperita* (peppermint; gene Tspa11), and AY835398 from *Artemisia annua*. Picaud et al., *Phytochemistry* 66(9): 961-967 (2005).

In some embodiments, the heterologous nucleotide encodes a farnesol synthase. Illustrative examples of suitable nucleotide sequences include, but are not limited to GenBank accession number AF529266 from *Zea mays* and YDR481C from *Saccharomyces cerevisiae* (gene Pho8). Song, L., *Applied Biochemistry and Biotechnology* 128:149-158 (2006).

In some embodiments, the heterologous nucleotide encodes a nerolidol synthase. An illustrative example of a suitable nucleotide sequence includes, but is not limited to AF529266 from *Zea mays* (maize; gene tps1).

In some embodiments, the heterologous nucleotide encodes a patchouliol synthase. Illustrative examples of suitable nucleotide sequences include, but are not limited to AY508730 REGION: 1.1659 from *Pogostemon cablin*.

In some embodiments, the heterologous nucleotide encodes a nootkatone synthase. Illustrative examples of a suitable nucleotide sequence include, but are not limited to AF441124 REGION: 1.1647 from *Citrus sinensis* and AY917195 REGION: 1.1653 from *Perilla frutescens*.

In some embodiments, the heterologous nucleotide encodes an abietadiene synthase. Illustrative examples of suitable nucleotide sequences include, but are not limited to: (U50768; *Abies grandis*) and (AY473621; *Picea abies*).

5.6 Production of Polyketides

In some embodiments, the non-catabolic compound is a polyketide. Polyketides are synthesized by sequential reactions catalysed by a collection of enzyme activities called polyketide synthases (PKSs), which are large multi-enzyme protein complexes that contain a coordinated group of active sites. Polyketide biosynthesis proceeds stepwise starting from simple 2-, 3-, 4-carbon building blocks such as acetyl-CoA, propionyl CoA, butyryl-CoA and their activated derivatives, malonyl-, methylmalonyl- and ethylmalonyl-CoA, primarily through decarboxylative condensation of malonyl-CoA-derived units via Claisen condensation reactions. The PKS genes are usually organized in one operon in bacteria and in gene clusters in eukaryotes. Three types of polyketide synthases have been characterized: Type I polyketide synthases are large, highly modular proteins subdivided into two classes: 1) iterative PKSs, which reuse domains in a cyclic fashion and 2) modular PKSs, which contain a sequence of separate modules and do not repeat domains. Type II polyketide synthases are aggregates of monofunctional proteins, and Type III polyketide synthases do not use acyl carrier protein domains.

Unlike fatty acid biosynthesis, in which each successive chain elongation step is followed by a fixed sequence of ketoreduction, dehydration and enoyl, reduction as described below, the individual chain elongation intermediates of polyketide biosynthesis undergo all, some, or no functional group modifications, resulting in a large number of chemically diverse products. Additional degrees of complexity arise from the use of different starter units and chain elongation units as well as the generation of new stereoisomers.

The order of complete polyketide-synthesis as directed by a polyketide synthase follows (in the order N-terminus to C-terminus): starting or loading the initial carbon building blocks onto an acyl carrier protein, elongation modules which catalyze the extension of the growing macrolide chain and termination modules that catalyze the release of the synthesized macrolide.

Component domains or separate enzyme functionalities active in this biosynthesis include acyl-transferases for the loading of starter, extender and intermediate acyl units; acyl carrier proteins which hold the growing macrolide as a thiol ester; β-keto-acyl synthases which catalyze chain extension; β-keto reductases responsible for the first reduction to an alochol functionality; dehydratases which eliminate water to give an unsaturated thioester; enoyl reductases which catalyse the final reduction to full saturation; and thiolesterases which catalyze macrolide release and cyclization.

In some embodiments, the genetically modified microorganism useful for the methods disclosed herein comprises a heterologous nucleotide sequence encoding an enzyme that can condense at least one of acetyl-CoA and malonyl-CoA with an acyl carrier protein, e.g. an acyl-transferase. In some embodiments, the genetically modified microorganism disclosed herein comprises a heterologous nucleotide sequence encoding an enzyme that can condense a first reactant selected from the group consisting of acetyl-CoA and malonyl-CoA with a second reactant selected from the group consisting of malonyl-CoA or methylmalonyl-CoA to form a polyketide product, e.g. a β-keto-acyl synthase.

In some embodiments, the polyketide producing cell comprises a heterologous nucleotide sequence encoding an enzyme that can reduce a β-keto chemical group on a polyketide compound to a β-hydroxy group, e.g. a β-keto reductase.

In some embodiments, the genetically modified microorganism disclosed herein comprises a heterologous nucleotide sequence encoding an enzyme that can dehydrate an alkane chemical group in a polyketide compound to produce an α-β-unsaturated alkene, e.g. a dehydratase.

In some embodiments, the polyketide producing cell comprises a heterologous nucleotide sequence encoding an enzyme that can reduce an α-β-double-bond in a polyketide compound to a saturated alkane, e.g. an enoyl-reductase.

In some embodiments, the polyketide producing cell comprises a heterologous nucleotide sequence encoding an enzyme that can hydrolyze a polyketide compound from an acyl carrier protein, e.g. a thioesterase.

In some embodiments, the polyketide producing cell comprises one or more heterologous nucleotide sequences encoding an enzyme comprising a KS catalytic region. In some embodiments, the polyketide producing cell comprises one or more heterologous nucleotide sequences encoding an enzyme comprising an AT catalytic region. In some embodiments, the polyketide producing cell comprises more than one heterologous nucleotide sequence encoding an enzyme comprising an AT catalytic region. In some embodiments, the polyketide producing cell comprises one or more heterologous nucleotide sequences encoding an enzyme comprising a CLF catalytic region. In some embodiments, the polyketide producing cell comprises one or more heterologous nucleotide sequences encoding an enzyme comprising an ACP activity. In some embodiments, the polyketide producing cell comprises more than one heterologous nucleotide sequence encoding an enzyme comprising an ACP activity.

In a particular embodiment, the polyketide producing cell comprises a minimal aromatic PKS system, e.g., heterologous nucleotide sequences encoding an enzyme comprising a KS catalytic region, an enzyme comprising an AT catalytic region, an enzyme comprising a CLF catalytic region, and an enzyme comprising an ACP activity, respectively. In a particular embodiment, the polyketide producing cell comprises a minimal modular PKS system, e.g., heterologous nucleotide sequences encoding an enzyme comprising a KS catalytic region, an enzyme comprising an AT catalytic region, and an enzyme comprising an ACP activity, respectively. In yet another particular embodiment, the polyketide producing cell comprises a modular aromatic PKS system for de novo polyketide synthesis, e.g., heterologous nucleotide sequences encoding an enzyme comprising a KS catalytic region, one or more enzymes comprising an AT catalytic region, and one or more enzymes comprising an ACP activity, respectively.

In some embodiments, the polyketide producing cell comprises a minimal PKS system, e.g., a minimal aromatic PKS system or minimal modular PKS system, further comprises additional catalytic activities which can contribute to production of the end-product polyketide. In some embodiments, the polyketide producing cell comprises one or more heterologous nucleotide sequences encoding an enzyme comprising a cyclase (CYC) catalytic region, which facilitates the cyclization of the nascent polyketide backbone. In some embodiments, the polyketide producing cell comprises one or more heterologous nucleotide sequences encoding an enzyme comprising a ketoreductase (KR) catalytic region. In some embodiments, the polyketide producing cell comprises one or more heterologous nucleotide sequences encoding an enzyme comprising an aromatase (ARO) catalytic region. In some embodiments, the polyketide producing cell comprises one or more heterologous nucleotide sequences encoding an enzyme comprising an enoylreductase (ER) catalytic region. In some embodiments, the polyketide producing cell comprises one or more heterologous nucleotide sequences encoding an enzyme comprising a thioesterase (TE) catalytic region. In some embodiments, the polyketide producing cell further comprises one or more heterologous nucleotide sequences encoding an enzyme comprising a holo ACP synthase activity, which effects pantetheinylation of the ACP.

In some embodiments, the polyketide producing cell further comprises one or more heterologous nucleotide sequences conferring a postsynthesis polyketide modifying activity. In some embodiments, the polyketide producing cell further comprises one or more heterologous nucleotide sequences encoding an enzyme comprising a glycosylase activity, which effects postsynthesis modifications of polyketides, for example, where polyketides having antibiotic activity are desired. In some embodiments, the polyketide producing cell further comprises one or more heterologous nucleotide sequences encoding an enzyme comprising a hydroxylase activity. In some embodiments, the polyketide producing cell further comprises one or more heterologous nucleotide sequences encoding an enzyme comprising an epoxidase activity. In some embodiments, the polyketide producing cell further comprises one or more heterologous nucleotide sequences encoding an enzyme comprising a methylase activity.

In some embodiments, the polyketide producing cell further comprises one or more heterologous nucleotide sequences encoding a biosynthetic enzyme including, but not limited to, at least one polyketide synthesis pathway enzyme, and enzymes that can modify an acetyl-CoA compound to form a polyketide product such as a macrolide, an antibiotic, an antifungal, a cytostatic compound, an anticholesterolemic compound, an antiparasitic compound, a coccidiostatic compound, an animal growth promoter or an insecticide. In some embodiments, the non-catabolic compound is a polyene. In some embodiments, the non-catabolic compound is a cyclic lactone. In some embodiments, the non-catabolic compound comprises a 14, 15, or 16-membered lactone ring. In some embodiments, the non-catabolic compound is a polyketide selected from the group consisting of a polyketide macrolide, antibiotic, antifungal, cytostatic, anticholesterolemic, antiparasitic, a coccidiostatic, animal growth promoter and insecticide.

In some embodiments, the polyketide producing cell comprises heterologous nucleotide sequences, for example sequences encoding PKS enzymes and polyketide modification enzymes, capable of producing a polyketide selected from, but not limited to, the following polyketides: Avermectin (see, e.g., U.S. Pat. Nos. 5,252,474; 4,703,009; EP Pub. No. 118,367; MacNeil et al., 1993, "Industrial Microorganisms: Basic and Applied Molecular Genetics"; Baltz, Hegeman, & Skatrud, eds. (ASM), pp. 245-256, "A Comparison of the Genes Encoding the Polyketide Synthases for Avermectin, Erythromycin, and Nemadectin"; MacNeil et al., 1992, *Gene* 115: 119-125; and Ikeda and Omura, 1997, *Chem. Res.* 97: 2599-2609); Candicidin (FR008) (see, e.g., Hu et al., 1994, *Mol. Microbiol.* 14: 163-172); Carbomycin, Curamycin (see, e.g., Bergh et al., *Biotechnol Appl Biochem.* 1992 February; 15(1):80-9); Daunorubicin (see, e.g., *J Bacteriol.* 1994 October; 176(20):6270-80); Epothilone (see, e.g., PCT Pub. No. 99/66028; and PCT Pub. No. 00/031247); Erythromycin (see, e.g., PCT Pub. No. 93/13663; U.S. Pat. Nos. 6,004,787; 5,824,513; Donadio et al., 1991, *Science* 252:675-9; and Cortes et al., Nov. 8, 1990, *Nature* 348:176-8); FK-506 (see, e.g., Motamedi et al., 1998; *Eur. J Biochem.* 256: 528-534; and Motamedi et al., 1997, *Eur. J Biochem.* 244: 74-80); FK-520 (see, e.g., PCT Pub. No. 00/020601; and Nielsen et al., 1991, *Biochem.* 30:5789-96); Griseusin (see, e.g., Yu et al., *J Bacteriol.* 1994 May; 176(9):2627-34); Lovastatin (see, e.g., U.S. Pat. No. 5,744,350); Frenolycin (see, e.g., Khosla et al., *Bacteriol.* 1993 April; 175(8):2197-204; and Bibb et al., *Gene* 1994 May 3; 142(1):31-9); Granaticin (see, e.g., Sherman et al., EMBO J. 1989 September; 8(9):2717-25; and Bechtold et al., *Mol Gen Genet.* 1995 Sep. 20; 248(5):610-20); Medermycin (see, e.g., Ichinose et al., *Microbiology* 2003 July; 149(Pt 7):1633-45); Monensin (see, e.g., Arrowsmith et al., *Mol Gen Genet.* 1992 August; 234(2):254-64); Nonactin (see, e.g., *FEMS Microbiol Lett.* 2000 Feb. 1; 183(1):171-5); Nanaomycin (see, e.g., Kitao et al., *J Antibiot* (Tokyo). 1980 July; 33(7):711-6); Nemadectin (see, e.g., MacNeil et al., 1993, supra); Niddamycin (see, e.g., PCT Pub. No. 98/51695; and Kakavas et al., 1997, *J. Bacteriol.* 179:

7515-7522); Oleandomycin (see e.g., Swan et al., 1994, *Mol. Gen. Genet.* 242: 358-362; PCT Pub. No. 00/026349; Olano et al., 1998, *Mol. Gen. Genet.* 259(3): 299-308; and PCT Pat. App. Pub. No. WO 99/05283); Oxytetracycline (see, e.g., Kim et al., *Gene.* 1994 Apr. 8; 141(1):141-2); Picromycin (see, e.g., PCT Pub. No. 99/61599; PCT Pub. No. 00/00620; Xue et al., 1998, *Chemistry & Biology* 5(11): 661-667; Xue et al., October 1998, *Proc. Natl. Acad. Sci. USA* 95: 12111 12116); Platenolide (see, e.g., EP Pub. No. 791,656; and U.S. Pat. No. 5,945,320); Rapamycin (see, e.g., Schwecke et al., August 1995, *Proc. Natl. Acad. Sci. USA* 92:7839-7843; and Aparicio et al., 1996, Gene 169: 9-16); Rifamycin (see, e.g., PCT Pub. No. WO 98/07868; and August et al., Feb. 13, 1998, *Chemistry & Biology*, 5(2): 69-79); Sorangium (see, e.g., U.S. Pat. No. 6,090,601); Soraphen (see, e.g., U.S. Pat. No. 5,716,849; Schupp et al., 1995, *J. Bacteriology* 177: 3673-3679); Spinocyn (see, e.g., PCT Pub. No. 99/46387); Spiramycin (see, e.g., U.S. Pat. No. 5,098,837); Tetracenomycin (see, e.g., Summers et al., *J Bacteriol.* 1992 March; 174(6):1810-20; and Shen et al., *J Bacteriol.* 1992 June; 174(11):3818-21); Tetracycline (see, e.g., *J Am Chem Soc.* 2009 Dec. 9; 131(48):17677-89); Tylosin (see, e.g., U.S. Pat. Nos. 5,876,991; 5,672,497; 5,149,638; EP Pub. No. 791,655; EP Pub. No. 238,323; Kuhstoss et al., 1996, Gene 183:231-6; and Merson-Davies and Cundliffe, 1994, *Mol. Microbiol.* 13: 349-355); and 6-methylsalicyclic acid (see, e.g., Richardson et al., *Metab Eng.* 1999 April; 1(2):180-7; and Shao et al., *Biochem Biophys Res Commun.* 2006 Jun. 23; 345(1):133-9).

5.7 Production of Fatty Acids

In some embodiments, the non-catabolic compound is a fatty acid. Fatty acids are synthesized by a series of decarboxylative Claisen condensation reactions from acetyl-CoA and malonyl-CoA catalyzed by fatty acid synthases. Similar to polyketide synthases, fatty acid synthases are not a single enzyme but an enzymatic system composed of 272 kDa multifunctional polypeptide in which substrates are handed from one functional domain to the next. Two principal classes of fatty acid synthases have been characterized: Type I fatty acid synthases are single, multifunctional polypeptides common to mammals and fungi (although the structural arrangement of fungal and mammalian synthases differ) and the CMN group of bacteria (corynebacteria, mycobacteria, and *nocardia*). Type II synthases, found in archaeabacteria and eubacteria, are a series of discrete, monofunctional enzymes that participate in the synthesis of fatty acids. The mechanisms fatty acid elongation and reduction is the same in the two classes of synthases, as the enzyme domains responsible for these catalytic events are largely homologous amongst the two classes.

Following each round of elongation of the fatty acid chain in the decarboxylative Claisen condensation reactions, the β-keto group is reduced to a fully saturated carbon chain by the sequential action of a ketoreductase, a dehydratase, and an enol reductase. The growing fatty acid chain moves between these active sites attached to an acyl carrier protein and is ultimately released by the action of a thioesterase upon reaching a carbon chain length of 16 (palmitidic acid).

In some embodiments, the genetically modified microorganism useful for the methods disclosed herein comprises a heterologous nucleotide sequence encoding a biosynthetic enzyme including, but not limited to, at least one fatty acid synthesis pathway enzyme, and enzymes that can modify an acetyl-CoA compound to form a fatty acid product such as a palmitate, palmitoyl CoA, palmitoleic acid, sapienic acid, oleic acid, linoleic acid, α-linolenic acid, arachidonic acid, eicosapentaenoic acid, erucic acid, and docosahexaenoic acid. In some embodiments, the non-catabolic compound is a fatty acid selected from the group consisting of palmitate, palmitoyl CoA, palmitoleic acid, sapienic acid, oleic acid, linoleic acid, α-linolenic acid, arachidonic acid, eicosapentaenoic acid, erucic acid, and docosahexaenoic acid.

In some embodiments, the fatty acid producing cell comprises a heterologous nucleotide sequence encoding an enzyme that can covalently link at least one of acetyl-CoA and malonyl-CoA with an acyl carrier protein, e.g. an acyl-transferase.

In some embodiments, the genetically modified microorganism disclosed herein comprises a heterologous nucleotide sequence encoding an enzyme that can condense acetyl chemical moiety and a malonyl chemical moiety, each bound to an acyl carrier protein (ACP), to form acetoacetyl-ACP, e.g. a β-Ketoacyl-ACP synthase.

In some embodiments, the fatty acid producing cell comprises a heterologous nucleotide sequence encoding an enzyme that can reduce the double bond in acetoacetyl-ACP with NADPH to form a hydroxyl group in D-3-hydroxybutyryl hydroxylase-ACP, e.g. a β-Ketoacyl-ACP reductase.

In some embodiments, the fatty acid producing cell comprises a heterologous nucleotide sequence encoding an enzyme that can dehydrate D-3-Hydroxybutyryl hydroxylase-ACP to create a double bond between the beta- and gamma-carbons forming crotonyl-ACP, e.g. a β-hydroxyacyl-ACP dehydrase.

In some embodiments, the fatty acid producing cell comprises a heterologous nucleotide sequence encoding an enzyme that can reduce crotonyl ACP with NADPH to form butyryl-ACP, e.g. an enoyl ACP reductase.

In some embodiments, the fatty acid producing cell comprises a heterologous nucleotide sequence encoding an enzyme that can hydrolyze a C16 acyl compound from an acyl carrier protein to form palmitate, e.g. a thioesterase.

In some embodiments, the fatty acid producing cell comprises one or more heterologous nucleotide sequences encoding acetyl-CoA synthase and/or malonyl-CoA synthase, to effect increased production of one or more fatty acids as compared to a genetically unmodified parent cell.

For example, to increase acetyl-CoA production, one or more of the following genes can be expressed in the cell: pdh, panK, aceEF (encoding the E1p dehydrogenase component and the E2p dihydrolipoamide acyltransferase component of the pyruvate and 2-oxoglutarate dehydrogenase complexes), fabH, fabD, fabG, acpP, and fabF. Illustrative examples of nucleotide sequences encoding such enzymes include, but are not limited to: pdh (BAB34380, AAC73227, AAC73226), panK (also known as coaA, AAC76952), aceEF (AAC73227, AAC73226),fabH (AAC74175), fabD (AAC74176), fabG (AAC74177), acpP (AAC74178), fabF (AAC74179).

In some embodiments, increased fatty acid levels can be effected in the cell by attenuating or knocking out genes encoding proteins involved in fatty acid degradation. For example, the expression levels of fadE, gpsA, idhA, pflb, adhE, pta, poxB, ackA, and/or ackB can be attenuated or knocked-out in an engineered host cell using techniques known in the art. Illustrative examples of nucleotide sequences encoding such proteins include, but are not limited to: fadE (AAC73325), gspA (AAC76632), ldhA (AAC74462), pflb (AAC73989), adhE (AAC74323), pta (AAC75357), poxB (AAC73958), ackA (AAC75356), and ackB (BAB81430). The resulting host cells will have increased acetyl-CoA production levels when grown in an appropriate environment.

In some embodiments, the fatty acid producing cell comprises a heterologous nucleotide sequence encoding an enzyme that can convert acetyl-CoA into malonyl-CoA, e.g., the multisubunit AccABCD protein. An illustrative example of a suitable nucleotide sequence encoding AccABCD includes but is not limited to accession number AAC73296, EC 6.4.1.2.

In some embodiments, the fatty acid producing cell comprises a heterologous nucleotide sequence encoding a lipase. Illustrative examples of suitable nucleotide sequences encoding a lipase include, but are not limited to accession numbers CAA89087 and CAA98876.

In some embodiments, increased fatty acid levels can be effected in the cell by inhibiting PlsB, which can lead to an increase in the levels of long chain acyl-ACP, which will inhibit early steps in the fatty acid biosynthesis pathway (e.g., accABCD, fabH, and fabI). The expression level of PlsB can be attenuated or knocked-out in an engineered host cell using techniques known in the art. An illustrative example of a suitable nucleotide sequence encoding PlsB includes but is not limited to accession number AAC77011. In particular embodiments, the plsB D31 IE mutation can be used to increase the amount of available acyl-CoA in the cell.

In some embodiments, increased production of monounsaturated fatty acids can be effected in the cell by overexpressing an sfa gene, which would result in suppression of fabA. An illustrative example of a suitable nucleotide sequence encoding sfa includes but is not limited to accession number AAN79592.

In some embodiments, increased fatty acid levels can be effected in the cell by modulating the expression of an enzyme which controls the chain length of a fatty acid substrate, e.g., a thioesterase. In some embodiments, the fatty acid producing cell has been modified to overexpress a tes or fat gene. Illustrative examples of suitable tes nucleotide sequences include but are not limited to accession numbers: (tesA: AAC73596, from *E. coli*, capable of producing $C_{18:1}$ fatty acids) and (tesB: AAC73555 from *E. coli*). Illustrative examples of suitable fat nucleotide sequences include but are not limited to: (fatB: Q41635 and AAA34215, from *Umbellularia california*, capable of producing $C_{12:0}$ fatty acids), (fatB2: Q39513 and AAC49269, from *Cuphea hookeriana*, capable of producing $C_{8:0}$—$C_{10:0}$ fatty acids), (fatB3: AAC49269 and AAC72881, from *Cuphea hookeriana*, capable of producing $C_{14:0}$—$C_{16:0}$ fatty acids), (fatB: Q39473 and AAC49151, from *Cinnamonum camphorum*, capable of producing $C_{14:0}$ fatty acids), (fatB [M141T]: CAA85388, from *Arabidopsis thaliana*, capable of producing $C_{16:1}$ fatty acids), (fatA: NP 189147 and NP 193041, from *Arabidopsis thaliana*, capable of producing $C_{18:1}$ fatty acids), (fatA: CAC39106, from *Bradvrhiizobium japonicum*, capable of preferentially producing $C_{18:1}$ fatty acids), (fatA: AAC72883, from *Cuphea hookeriana*, capable of producing $C_{18:1}$ fatty acids), and (fatA1, AAL79361 from *Helianthus annus*).

In some embodiments, increased levels of $C_{10}$ fatty acids can be effected in the cell by attenuating the expression or activity of thioesterase $C_{18}$ using techniques known in the art. Illustrative examples of suitable nucleotide sequences encoding thioesterase $C_{18}$ include, but are not limited to accession numbers AAC73596 and P0ADA1. In other embodiments, increased levels of $C_{10}$ fatty acids can be effected in the cell by increasing the expression or activity of thioesterase $C_{10}$ using techniques known in the art. An illustrative example of a suitable nucleotide sequence encoding thioesterase $C_{10}$ includes, but is not limited to accession number Q39513.

In some embodiments, increased levels of $C_{14}$ fatty acids can be effected in the cell by attenuating the expression or activity of endogenous thioesterases that produce non-$C_{14}$ fatty acids, using techniques known in the art. In other embodiments, increased levels of $C_{14}$ fatty acids can be effected in the cell by increasing the expression or activity of thioesterases that use the substrate $C_{14}$-ACP, using techniques known in the art. An illustrative example of a suitable nucleotide sequence encoding such a thioesterase includes, but is not limited to accession number Q39473.

In some embodiments, increased levels of $C_{12}$ fatty acids can be effected in the cell by attenuating the expression or activity of endogenous thioesterases that produce non-$C_{12}$ fatty acids, using techniques known in the art. In other embodiments, increased levels of $C_{12}$ fatty acids can be effected in the cell by increasing the expression or activity of thioesterases that use the substrate $C_{12}$-ACP, using techniques known in the art. An illustrative example of a suitable nucleotide sequence encoding such a thioesterase includes, but is not limited to accession number Q41635.

6. EXAMPLES

6.1 Example 1

This example describes an exemplary method for determining the cell density ($OD_{600}$) of a yeast cell culture.

An 8 µL sample of a cell culture was combined with 92 µL of Triton OD Diluent (20 g/L Triton X-114, 200 mL/L PEG 200, 200 mL/L 100% ethanol, rest water) in a clear 96-well plate, the solution was agitated at 1,000 RPM for 6 minutes, and the $OD_{600}$ was determined by measuring absorbance at 600 nm on an M5 spectrophotometer (Molecular Devices, Sunnyvale, Calif.).

6.2 Example 2

This example describes an exemplary Nile Red based method useful for determining the farnesene titer of yeast cell cultures.

A 98 µL sample of a cell culture was transferred into a 96-well black polystyrene flat bottom assay plate, and 2 µL of Nile Red (Invitrogen, Carlsbad, Calif.) dissolved at 100 µg/mL in DMSO was added to each well. Fluorescence levels were immediately measured on an M5 spectrophotometer with excitation at 500 nm and emission at 550 nm.

6.3 Example 3

This example describes an exemplary gas chromaogrpahy (GC) based method useful for determining the farnesene titer of yeast cell cultures.

Sample was extracted with methanol-heptane (1:1 v/v), and the mixture was centrifuged to remove cellular material. An aliquot of the methanol-heptane extract was diluted into n-heptane with 0.001% t-caryohyllene (which served as a retention time marker to monitor successful injection and elution during the specified GC oven profile) and then injected onto a methyl silicone stationary phase using a pulsed split injection. Famesene was separated by boiling point using GC with flame ionization detection (FID).

6.4 Example 4

This example demonstrates the phenomenon of strain degeneration which occurs when non-catabolic compound production is "on" during both the build and production stages of a fermentation process.

A 1 ml vial of frozen cell suspension of a yeast strain comprising heterologous enzymes including the MEV pathway enzymes (FIG. 1): IPP isomerase, FPP synthase, and farnesene synthase, and capable of producing an exemplary non-catabolic compound (farnesene), was thawed, transferred into a 250-ml baffled flask containing 50 ml of BSM 2.0 containing 2% sucrose and 10 mg/L calcium D-pantothenate, and grown in a shaker at 34° C., 200 RPM for 24 hours. The entire culture was then transferred into a 2.8 L Fembach flask containing 850 ml of BSM 2.0 containing 2.0% sucrose and 10 mg/L calcium D-pantothenate, and grown in a shaker at 34° C., 250 RPM for 24 hours. The entire culture was then transferred into a 2 L fermentor. The nutrient feed to the fermentor was an undefined Brazilian cane syrup media comprising 10 mg/L calcium D-pantothenate, delivered with initial pulses equivalent to a 14 g/L/h sugar. The feed rate was then self-adjusted based on the fermentor demand for carbon, as indicated by rises in dissolved oxygen. The fermentation was run micro-aerobically at a constant temperature of 34° C., a constant pH of 4.5 (controlled by sodium hydroxide additions), and an initial oxygen transfer rate of 200 mmol $O_2$/L/h until the dissolved oxygen reached 0%, and then reduced to 100 mmol $O_2$/L/h for the remainder of the fermentation. Every three days, the volume of the tank was reduced to about 0.9 L to prevent overflow. Trace metals and vitamins missing in the cane syrup feed were replenished at that time. The amount of farnesene produced and the total sugar consumed by the cells was monitored daily and the ratio of these two values (i.e., the product yield off of sugar) was determined for each 72 hour period and plotted as shown in FIG. 3. The product yield of the culture declined from its peak at 6 days to <65% of that peak by 21 days.

6.5 Example 5

This example provides results demonstrating that host cells capable of producing the isoprenoid farnesene, and comprising the MEV pathway under positive regulation by a microaerobic responsive promoter ("low $O_2$ switch"), produce very low amounts of farnesene in the high $O_2$ condition (shake plate), and in the low $O_2$ condition (shake flask with low RPM), production is substantially increased to levels matching the production of a non-switchable parent strain in which the MEV pathway is constitutively expressed. The results are depicted in FIG. 6.

Farnesene Producing Yeast Strains:

A "non-switchable" farnesene production strain derived from a wild-type *Saccharomyces cerevisiae* strain (CEN.PK2) and expressing the genes of the mevalonate pathway (FIG. 1) under the control of GAL promoters was used as a constitutive farnesene-producing control. The non-switchable strain comprised the following chromasomally integrated mevalonate pathway genes from *S. cerevisiae* under the control of GAL promoters: acetyl-CoA thiolase, HMG-CoA synthase, HMG-CoA reductase, mevalonate kinase, phosphomevalonate kinase, and mevalonate pyrophosphate decarboxylase; and six copies of farnesene synthase mutants from *Artemisinin annua*. The non-switchable strain has gal80 gene deleted and an additional copy of GAL4 under GAL4oc promoter, wherein the coding sequence of the GAL4 gene of *Saccharomyces cerevisiae* is under regulatory control of an "operative constitutive" version of its native promoter (PGAL4oc; see, e.g., Griggs & Johnston (1991) PNAS 88(19):8597-8601).

Farnesene production in the "non-switchable" strain was then made "switchable," that is, repressible under aerobic conditions. The low $O_2$ switch switchable strain was built on top of the constitutive strain by replacing the promoters of the multiple copies of GAL4 with the DAN1 #1 promoter (SEQ ID NO: 1). The first copy of pDAN1 #1 driving GAL4 was introduced by replacing pGAL4oc with pDAN1 #1. Then the native GAL4 promoter was replaced with pDAN1 #1. This strain is referred to as the "Low $O_2$ switchable strain #1" in FIG. 6. From this strain, third and fourth copies of pDAN1 #1 driving GAL4 were integrated at the GAS2 locus at the same time. This second switchable strain with four copies of GAL4 under the control of DAN1 #1 promoter is referred to as "Low $O_2$ switchable strain #2" in FIG. 7.

Regulation of Non-Catabolic Compound Production by Varying Oxygen Conditions:

Both the non-switchable farnesene producing control strain and the Low $O_2$ switchable strain #1 were cultured under aerobic and microaerobic conditions, respectively, to assess farnesene production under fermentation conditions intended to serve as "off" and "on" states.

For the "off" or "high $O_2$ condition," colonies of both strains were picked into 360 uL BSM 2.0, 2% sucrose in a 96 well plate. Plates were agitated at high RPM in an ATR shaker for 3 days. From this preculture plate, 6 uL of culture was transferred to a production 96 well plate containing 360 uL BSM 2.0, 4% sucrose. Plates were agitated at high RPM in an ATR shaker for 2 days. Farnesene concentration was determined by GC-FID.

For the "on" or "low $O_2$ condition", 125 ml flasks were filled with 50 ml of BSM 2.0, 4% media and inoculated at 0.1 OD of each strain. Fifty ml is an unusually large volume of media for a 125 ml flask size, and this helped reduce the oxygen transfer rate (OTR) into the flask to ensure the culture became microaerobic. Dissolved oxygen was measured via a probe, which confirmed that both strains reached undetectable dissolved oxygen levels within 24 h. Farnesene concentration was determined by GC-FID after 120 h. At 120 h, the dissolved oxygen for both cultures was approximately the value expected for equilibrium with the gas phase, implying carbon exhaustion.

As shown in FIG. 6, the Low $O_2$ switchable strain #1 produced very little farnesene under high $O_2$ conditions, compared to the constitutive non-switchable strain which produced high levels of farnesene. In the low $O_2$ condition, induction of farnesene production was high in the Low $O_2$ switchable strain #1, and exceeded the farnesene production by the constitutive non-switchable strain. These results demonstrate that oxygen manipulation can be used to effect tight "off" and "on" states for a low $O_2$ switchable, farnesene producing strain.

6.6 Example 6

This example provides results demonstrating that host cells capable of producing the isoprenoid farnesene, and comprising the MEV pathway under positive regulation by a low $O_2$ switch, display improved stability of production of farnesene in a long fermentation run when the build stage of the fermentation is performed under aerobic conditions (thereby effecting an "off" state), compared to production from a constitutively producing strain that produced farnesene throughout the build stage. The results are depicted in FIG. 7.

For both the non-switchable constitutive farnesene producing strain and the Low $O_2$ switchable strain #2, a 1 ml vial of frozen cell suspension was thawed, transferred into a 250-ml baffled flask containing 50 ml of BSM 3.0 containing 1.6% sucrose 0.4% glucose as a carbon source, and grown in a shaker at 34° C., 250 RPM for 24 hours. Two ml from that flask was then transferred into 50 ml of BSM 3.0 containing 1.6% sucrose 0.4% glucose as a carbon source, and grown in a shaker at 34° C., 250 RPM for 24 hours. Twenty five ml was then transferred into an inoculation bottle with 225 ml of tank media and transferred to a 0.5 L fermentor. The nutrient feed to the fermentor was a 650 g/L sucrose solution, delivered with initial pulses equivalent to a 10 g/L/h sugar. The feed rate is then self-adjusted based on the fermentor demand for carbon, as indicated by rises in dissolved oxygen. The fermentation was run micro-aerobically at a constant temperature of 34° C., a constant pH of 4.5 (controlled by sodium hydroxide additions), and a maximal oxygen transfer rate of 110 mmol $O_2$/L/h once the dissolved oxygen reaches 0%. Every day, the volume of the tank was reduced to about 0.29 L to prevent overflow. Trace metals and vitamins were replenished at that time. The total amount of farnesene produced and the total sugar consumed by the cells was updated daily, and the ratio of these two values (i.e., the cumulative product yield off of sugar) was determined for the interval from time=0 to time=t and plotted as shown in FIG. 7. The cumulative product yield of the non-switchable parent strain declined continuously from its peak at 160 h to about ~83% of the peak yield of the switchable child strain at 300 h. By contrast, the low $O_2$ switchable strain #2 maintained a cumulative yield that was >95% of its peak from 110 h to 300 h. Thus, these results demonstrate that a low $O_2$ switch that turns off farnesene production under aerobic conditions during the build stage of a two-stage fermentation process results in improved production stability of farnesene production during the production stage.

6.7 Example 7

This example provides results demonstrating that host cells capable of producing the isoprenoid farnesene, and comprising the MEV pathway under negative regulation by a maltose-responsive promoter ("maltose switch"), produce very low amounts of farnesene in the presence of maltose (1.3%), and in the absence of maltose, production is substantially increased to levels nearing the production of a non-switchable parent strain in which the MEV pathway is constitutively expressed. The results are depicted in FIG. 8.

Farnesene Producing Yeast Strains:

A "non-switchable" farnesene production strain derived from a wild-type *Saccharomyces cerevisiae* strain (CEN.PK2) and expressing the genes of the mevalonate pathway (FIG. 1) under the control of GAL promoters was used as a constitutive farnesene-producing control. The non-switchable strain comprised the following chromasomally integrated mevalonate pathway genes from *S. cerevisiae* under the control of GAL promoters: acetyl-CoA thiolase, HMG-CoA synthase, HMG-CoA reductase, mevalonate kinase, phosphomevalonate kinase, and mevalonate pyrophosphate decarboxylase; and six copies of farnesene synthase mutants from *Artemisinin annua*. The non-switchable strain has gal80 gene deleted and an additional copy of GAL4 under GAL4oc promoter, wherein the coding sequence of the GAL4 gene of *Saccharomyces cerevisiae* is under regulatory control of an "operative constitutive" version of its native promoter (PGAL4oc; see, e.g., Griggs & Johnston (1991) PNAS 88(19):8597-8601).

Farnesene production in the "non-switchable" strain was then made "switchable," that is, repressible in the presence of maltose. The maltose switchable strain was built on top of the constitutive strain by chromasomally integrating a copy of GAL80 under the control of the maltose-responsive promoter pMAL32 (SEQ ID NO:17).

Regulation of Non-Catabolic Compound Production by Varying Maltose in the Culture Medium:

Both the non-switchable farnesene producing control strain and the maltose switchable strain were cultured in culture medium including or excluding maltose, respectively, to assess farnesene production under fermentation conditions intended to serve as "off" and "on" states.

For preculture conditions, both the non-switchable farnesene producing control strain and the maltose switchable strain were cultured were gown in sterile 96-well plates (1.1 ml working volume; Axygen) containing 360 ul of Bird Seed Media (BSM, originally described by van Hoek et al., (2000). Single colonies were picked into each well and incubated for approximately 72 hours at 33.5° C., 80% humidity and 1000 rpm (Infors Multitron; ATR Biotec). For farnesene production experiments, the aforementioned saturated cultures were diluted 1/25 into sterile 1.1 ml plates containing 145 µl of BSM and 5 µl of mineral oil. The carbon source was either 4% sucrose, or a mixture of 2.7% sucrose and 1.3% maltose. After 72 hours of culture, farnesene extraction was performed by adding 600 µl of isopropyl alcohol (IPA) to each well. After a 30-minute incubation, 8 µl was transferred to a clear bottom assay plate containing 192 µl IPA. Farnesene concentration was measured by UV absorbance at 222 nm on a SpectraMax plate reader.

As shown in FIG. 8, the maltose switchable strain produced very little farnesene in the presence of maltose, compared to the constitutive non-switchable strain which produced high levels of farnesene. In the absence of maltose, induction of farnesene production was high in the maltose-switchable strain, and neared the farnesene production by the constitutive non-switchable strain. These results demonstrate that maltose manipulation can be used to effect tight "off" and "on" states for a maltose switchable, farnesene producing strain.

6.8 Example 8

This example provides results demonstrating that host cells capable of producing the isoprenoid farnesene, and comprising the MEV pathway either under (i) positive regulation by a microaerobic responsive promoter ("low $O_2$ switch"); or negative regulation by a maltose-responsive promoter ("maltose switch"), have improved growth rates during the "off" state of compound production compared to a parent strain constitutively producing farnesene. The results are depicted in FIG. 9.

For growth rate experiments, saturated cultures of the Low $O_2$ switchable strain #1, the maltose switchable strain, and the non-switchable constitutive farnesene producer were diluted 1/25 into sterile 1.1 ml plates containing 360 µl of fresh defined media containing 3% (w/v) sucrose, or a mixture of 2% sucrose and 1% maltose. Growth rate was calculated by measuring OD600 (SpectraMax M5 plate reader; Molecular Devices) over a period of 8 hours immediately following the transfer to fresh media (2.5, 3.5, 6 and 8 hr). To eliminate any contribution of farnesene emulsion to the OD signal, cultures were diluted in a solution of 20% (v/v) PEG 20, 20% (v/v) Ethanol, 2% (v/v) Triton X-114. Growth rates were determined by applying a linear regression to LN (OD) vs time.

As shown in FIG. 9, the maltose switchable strain showed improved growth in the "off" state (i.e., in the presence of maltose) compared to its "on" state, and significantly improved growth over the non-switchable constitutive farnesene producing strain (143% vs. 100% relative growth rates). Similarly, the Low $O_2$ switchable strain #1 showed significantly improved growth in the "off" state (i.e., under aerobic conditions) compared to the non-switchable constitutive farnesene producing strain (167% vs. 100% relative growth rates).

6.9 Example 9

This example provides results demonstrating that host cells capable of producing the isoprenoid farnesene, and comprising the MEV pathway under negative regulation by a maltose switch, display improved stability of production of farnesene in a long fermentation run when the build stage of the fermentation is performed in the presence of maltose (thereby effecting an "off" state), compared to production from a constitutively producing strain that produced farnesene throughout the build stage. The results are depicted in FIG. 10.

Both the non-switchable farnesene producing control strain and the maltose switchable strain were initially struck out on a solid agar medium containing 2% dextrose and 1% maltose and grown at 30° C. until colonies were visible. Seed vials were prepared by inoculating a single colony into a 15 ml tube containing 3 ml of BSM 2% sucrose 1% maltose. After approximately 48 hours, all 3 ml was transferred into 500 mL disposable shake flask containing 125 mL of 2% sucrose and 1% maltose BSM (seed vial medium). Cells were grown at 30° C. in a shaker at 200 rpm until an OD600 between 4 and 7 was reached. Once the desired OD has been reached, 36 ml of a sterile 50% glycerol stock was added to 84 ml of culture, the suspension was aliquoted into seed vials, and the seed vials were slowly frozen to −80° C. at a rate of approximately 1° C./min. Biomass build prior to the fermentation was accomplished by thawing one or more seed vials into a 250 mL shake flask containing 50 mL of 2% sucrose and 1% maltose BSM (biomass build medium), and by growing the culture for 24 hours at 34° C. and 200 RPM. A portion of this culture was then transferred a 500 ml flask containing 100 ml of the same medium to reach a starting OD600 of 0.1, and grown for an additional 24 hours. 25 ml of this culture was then used to inoculate a 0.5 L fermentor containing 225 ml of BSM media lacking any sugar. Cane syrup (without any maltose) was fed on demand and the fermentation was run for 13 days following a feeding protocol that maximized farnesene yield.

The total amount of farnesene produced and the total sugar consumed by the cells was updated daily, and the ratio of these two values was determined for the interval from time=0 to time=t and plotted as normalized fermentor interval yield, as shown in FIG. 10. The normalized interval yield of the non-switchable parent strain declined continuously from its peak at 120 h to well below ~20% of the peak yield of the switchable child strain at 300 h. By contrast, the maltose switchable strain maintained a normalized interval yield that was ~50% of its peak from 72 h to 120 h. Thus, these results demonstrate that a maltose switch that turns off farnesene production in the presence of maltose during the build stage of a two-stage fermentation process results in improved production stability of farnesene production during the production stage.

6.10 Example 10

This example provides results demonstrating, for several maltose-sensitive promoters described herein, the sensitivity to varying amounts of maltose and to mixed feeds in the culture medium, and well as to the switchability to the "on" state in the absence of maltose, following repression by maltose in the "off" state. The results are depicted in FIGS. 11-14.

For each of the maltose-responsive promoters pMAL11 (SEQ ID NO: 14), pMAL12 (SEQ ID NO:15), pMAL31 (SEQ ID NO:16), and pMAL32 (SEQ ID NO:17)), two different reporter strains derived from a wild-type *Saccharomyces cerevisiae* strain (CEN.PK2) were generated by integrating the following reporter constructs at the ATG20 locus: (i) pMAL>GFP, a GFP coding sequence operably linked to the maltose-sensitive promoter, and (ii) pMAL>GAL80; pGAL1>GFP, a construct comprising a GFP expression cassette operably linked to the GAL1 promoter; and a GAL80 coding sequence operably linked to the maltose-sensitive promoter.

For pMAL>GFP and switch strains with pGAL1>GFP, precultures were diluted 50-fold into fresh media containing the indicated mixtures of glucose with maltose or sucrose with maltose. After an additional 24 hour incubation, cultures were diluted into a PBS solution for a final cell density ranging from 300-1000 cells/uL and sorted on the Guava. Cells were first sorted by forward and side scatter, intact yeast cells were differentiated and gated away from much smaller debris and fene particles. Fluorescent green cells were identified using the output from an isogenic non-GFP expressing control strain as the non-fluorescent background signal. Histograms were constructed using the Flowjo software.

As shown in FIGS. 11-14 (A), each of pMAL11, pMAL12, pMAL31 and pMAL32 were robustly activated by maltose as low as 0.5%, even when mixed with glucose or sucrose. Additionally, as shown in FIGS. 11-14 (B), each of pMAL11, pMAL12, pMAL31 and pMAL32 were able to maintain strong off-states, when wired as a "maltose-on" switch (left panels), or strong on-states, when wired as a "maltose-off" switch (right panels) when the host strains were subsequently cultured in media not comprising maltose (4% sucrose).

All publications, patents and patent applications cited in this specification are herein incorporated by reference as if each individual publication or patent application were specifically and individually indicated to be incorporated by reference. Various modifications and variations of the present disclosure will be apparent to those skilled in the art without departing from the scope and spirit of the disclosure. Although the disclosure has been described in some detail by way of illustration and example for purposes of clarity of understanding, it will be readily apparent to those of ordinary skill in the art in light of the teachings provided herein that certain changes and modifications may be made thereto without departing from the spirit or scope of the appended claims, and that the claims should not be unduly limited to such specific embodiments. Indeed, various modifications of the described modes for carrying out the disclosure, which are understood by those skilled in the art, are intended to be within the scope of the claims.

What is claimed is:

1. A genetically modified yeast host cell comprising:
   (i) one or more heterologous nucleic acids encoding one or more enzymes of an enzymatic pathway for making the heterologous non-catabolic compound, wherein expression of the one or more enzymes is regulated by the activity of a maltose-responsive promoter; and
   (ii) Gal4p;
   wherein the maltose-responsive promoter is operably linked to a heterologous nucleic acid encoding a transcriptional regulator that negatively regulates Gal4p transcriptional activity;
   wherein the one or more enzymes of the enzymatic pathway are each operably linked to a Gal4p-responsive promoter.

2. The genetically modified yeast host cell of claim 1, wherein expression of the one or more enzymes of an enzymatic pathway is decreased in the presence of maltose.

3. The genetically modified yeast host cell of claim 1, wherein the transcriptional regulator is Gal80p, and wherein expression of Gal80p is increased in the presence of maltose.

4. The genetically modified yeast host cell of claim 1, wherein the Gal4p-responsive promoter is selected from the group consisting of pGAL1, pGAL7 and pGAL10.

5. The genetically modified yeast host cell of claim 1, wherein one or more heterologous nucleic acids encodes one or more enzymes of the mevalonate (MEV) pathway.

6. The genetically modified yeast host cell of claim 1, wherein the maltose-responsive promoter comprises a sequence selected from the group consisting of pMAL1 (SEQ ID NO:12), pMAL2 (SEQ ID NO:13), pMAL11 (SEQ ID NO:14), pMAL12 (SEQ ID NO:15), pMAL31 (SEQ ID NO:16) and pMAL32 (SEQ ID NO:17).

7. The genetically modified yeast host cell of claim 6, wherein the maltose-responsive promoter sequence comprises pMAL32 (SEQ ID NO:17).

8. The genetically modified yeast host cell of claim 1, wherein the culture medium comprises at least 0.1% (w/v) maltose.

9. The genetically modified yeast host cell of claim 1, wherein the culture medium comprises 0.25% to 3% (w/v) maltose.

10. The genetically modified yeast host cell of claim 1, wherein the culture medium comprises no more than 0.08% maltose.

11. A fermentation composition comprising the genetically modified yeast host cell of claim 1.

* * * * *